(12) United States Patent
Naeymi-Rad et al.

(10) Patent No.: US 8,612,448 B2
(45) Date of Patent: Dec. 17, 2013

(54) LONGITUDINAL ELECTRONIC RECORD SYSTEM AND METHOD WITH PROBLEM DETERMINATION AND PLAN ORDERING

(75) Inventors: Frank Naeymi-Rad, Libertyville, IL (US); Regis J P Charlot, Lake Bluff, IL (US); Alina E. Oganesova, Chicago, IL (US); David O. Haines, Arlington Heights, IL (US); Aziz M. Bodal, Arlington Heights, IL (US); Andre L. Young, Jr., Kenosha, WI (US); Masayo Kobashi, Long Grove, IL (US); Stephanie J. Schaefer, Gurnee, IL (US); Andrew Stuart Kanter, Northbrook, IL (US); Kim Charles Meyers, Evanston, IL (US); Jose Antonio Maldonado, Jr., Chicago, IL (US)

(73) Assignee: Intelligent Medical Objects, Inc., Northbrook, IL (US)

( * ) Notice: Subject to any disclaimer, the term of this patent is extended or adjusted under 35 U.S.C. 154(b) by 0 days.

(21) Appl. No.: 13/531,183

(22) Filed: Jun. 22, 2012

(65) Prior Publication Data
US 2012/0265788 A1    Oct. 18, 2012

Related U.S. Application Data

(62) Division of application No. 11/858,241, filed on Sep. 20, 2007.

(51) Int. Cl.
*G06F 17/30* (2006.01)
*G06F 7/00* (2006.01)

(52) U.S. Cl.
USPC .......................................... 707/738; 707/740

(58) Field of Classification Search
USPC .................................................. 707/738, 740
See application file for complete search history.

(56) References Cited

U.S. PATENT DOCUMENTS

| | | | |
|---|---|---|---|
| 5,748,872 A | 5/1998 | Norman | |
| 5,819,257 A | 10/1998 | Monge et al. | |
| 5,903,889 A | 5/1999 | de la Huerga et al. | |
| 5,931,900 A | 8/1999 | Notani et al. | |
| 6,006,233 A | 12/1999 | Schultz | |
| 6,029,162 A | 2/2000 | Schultz | |
| 6,078,924 A | 6/2000 | Ainsbury et al. | |
| 6,105,035 A | 8/2000 | Monge et al. | |
| 6,115,715 A | 9/2000 | Traversat et al. | |

(Continued)

OTHER PUBLICATIONS

Ellison, Introduction to SQL, booklet, 1989, Oracle Corporation, USA.

*Primary Examiner* — Mariela Reyes
(74) *Attorney, Agent, or Firm* — Beem Patent Law Firm

(57) ABSTRACT

A system and method for keeping, organizing and managing electronic records, comprising generating a first instance of data objects comprising data elements during a first encounter, the elements comprising a first instance identifier and temporal identifiers; linking a data object to a summarization reference with a pointer; creating an additional instance of data objects also comprising data elements comprising an additional instance identifier and temporal identifiers during a later encounter; and providing continuity for the first instance data objects over time. Continuity may be provided by tracking a relationship between the first instance data object and an additional instance data object and repointing the pointer to point between the summarization reference and the additional instance data object. The additional instance data object may be a revision of the first instance data object, and tracking may occur by back-linking the revision to the first instance data object.

19 Claims, 46 Drawing Sheets

(56) References Cited

U.S. PATENT DOCUMENTS

| | | |
|---|---|---|
| 6,122,636 A | 9/2000 | Malloy et al. |
| 6,167,406 A | 12/2000 | Hoskins et al. |
| 6,192,371 B1 | 2/2001 | Schultz |
| 6,246,794 B1 | 6/2001 | Kagehiro et al. |
| 6,345,268 B1 | 2/2002 | de la Huerga |
| 6,345,278 B1 | 2/2002 | Hitchcock et al. |
| 6,405,211 B1 | 6/2002 | Sokol et al. |
| 6,523,009 B1 | 2/2003 | Wilkins |
| 6,643,652 B2 | 11/2003 | Helgeson et al. |
| 6,662,188 B1 | 12/2003 | Rasmussen et al. |
| 6,708,186 B1 | 3/2004 | Claborn et al. |
| 6,721,747 B2 | 4/2004 | Lipkin |
| 6,901,398 B1 | 5/2005 | Horvitz et al. |
| 6,987,221 B2 | 1/2006 | Platt |
| 2001/0051880 A1 | 12/2001 | Schurenberg |
| 2002/0007284 A1 | 1/2002 | Schurenberg |
| 2002/0010679 A1 | 1/2002 | Felsher |
| 2002/0169788 A1 | 11/2002 | Lee et al. |
| 2003/0036683 A1 * | 2/2003 | Kehr et al. ............ 600/300 |
| 2003/0115084 A1 | 6/2003 | Gage |
| 2005/0108052 A1 | 5/2005 | Omaboe |
| 2007/0271313 A1 | 11/2007 | Mizuno et al. |
| 2008/0172737 A1 | 7/2008 | Shen et al. |
| 2008/0221920 A1 | 9/2008 | Courtney |
| 2008/0262868 A1 | 10/2008 | Malolepszy |
| 2008/0312959 A1 * | 12/2008 | Rose et al. ............ 705/2 |

* cited by examiner

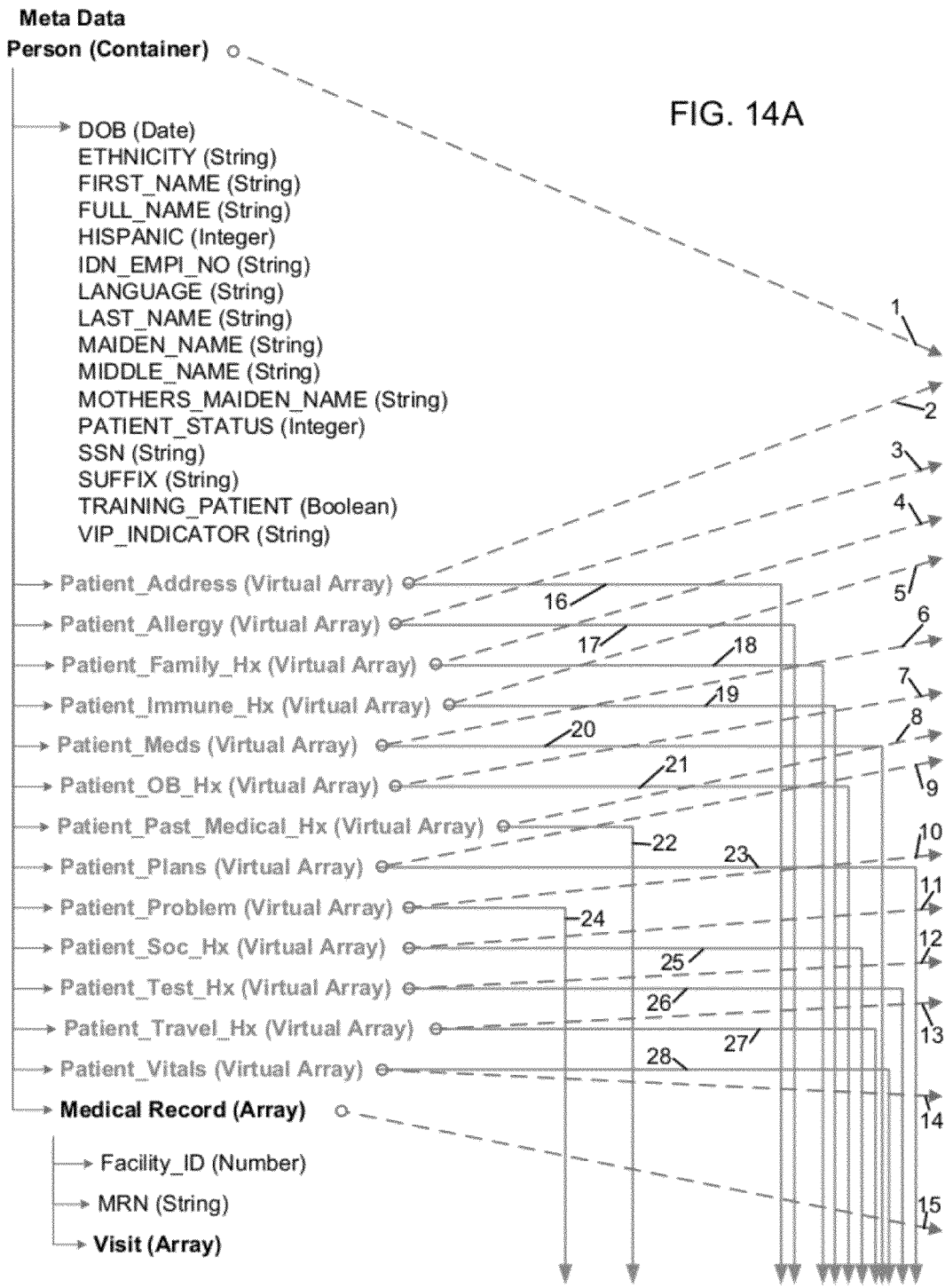

```
CREATE TABLE ALLERGY$
(
    ALLERGY$_CODE                   NUMBER NOT NULL,
    VISITS_CODE                     NUMBER NOT NULL,
    ALLERGY$_TEXT                   VARCHAR2(4000),
    ALLERGY$_PREV                   NUMBER,
    ALLERGY_ADDED_DATE              DATE,
    ALLERGY_CODE                    VARCHAR2(50),
    ALLERGY_COMMENT                 VARCHAR2(4000),
    ALLERGY_DEFAULT_SCRIPT          VARCHAR2(100),
    ALLERGY_DESCRIPTION             VARCHAR2(250),
    ALLERGY_DISPLAY_PLIST           NUMBER(1),
    ALLERGY_DONOT_RECHALLENGE       NUMBER(1),
    ALLERGY_END_DATE                DATE,
    ALLERGY_LAST_MODIFIED_DA        DATE,
    ALLERGY_MATNO                   VARCHAR2(50),
    ALLERGY_ONSET_DATE              DATE,
    ALLERGY_REPORT_SHOW             NUMBER(1),
    ALLERGY_SOURCE                  VARCHAR2(50),
    ALLERGY_STATUS                  VARCHAR2(50),
    ALLERGY_USER_ID_ADDED           NUMBER,
    ALLERGY_USER_ID_LAST_MOD        NUMBER,
    TAG_ORDER                       NUMBER,
    TAG_CREATEDATE                  DATE DEFAULT sysdate NOT NULL,
    TAG_SYSTEMDATE                  DATE DEFAULT sysdate NOT NULL,
    TAG_SYSTEMUSER                  NUMBER NOT NULL
)
```

FIG. 14S

```
PROBLEM_HX_ACTIVITY          NUMBER,
PROBLEM_LAST_MODIFIED_DATE   DATE,
PROBLEM_NOTE                 CLOB,
PROBLEM_OLD_REVISION         NUMBER(1),
PROBLEM_ONSET_DATE           DATE,
PROBLEM_ONSET_DATE_PARTIAL   VARCHAR2(20),
PROBLEM_ORIENTATION_TEXT     CLOB,
PROBLEM_PLANS_TEXT           CLOB,
PROBLEM_REPORT_SHOW          NUMBER(1),
PROBLEM_SEVERITY_FLAG        NUMBER,
PROBLEM_SHOW_IN_HISTORY      NUMBER(1),
PROBLEM_SHOW_IN_PROBLEMS     NUMBER(1),
PROBLEM_SOURCE               VARCHAR2(50),
PROBLEM_STATUS               VARCHAR2(50),
PROBLEM_STATUS1_SUBJECTIVE   VARCHAR2(50),
PROBLEM_STATUS2              VARCHAR2(50),
PROBLEM_STATUS2_COPY         VARCHAR2(4000),
PROBLEM_STATUS2_FLAG         NUMBER,
PROBLEM_STATUS2_SUBJECTIVE   VARCHAR2(50),
PROBLEM_USER_ID_ADDED        NUMBER,
PROBLEM_USER_ID_LAST_MODIF   NUMBER,
TAG_ORDER                    NUMBER,
TAG_CREATEDATE               DATE DEFAULT sysdate NOT NULL,
TAG_SYSTEMDATE               DATE DEFAULT sysdate NOT NULL,
TAG_SYSTEMUSER               NUMBER NOT NULL
)
```

```
PLAN_LOCATION                  VARCHAR2(250),
PLAN_NEEDS_FOLLOWUP            NUMBER(1),
PLAN_NOTE                      VARCHAR2(4000),
PLAN_OLD_REVISION              NUMBER(1),
PLAN_ONSET_DATE                DATE,
PLAN_ONSET_DATE_PARTIAL        VARCHAR2(20),
PLAN_ORDERID                   NUMBER,
PLAN_ORDER_FORM                NUMBER(1),
PLAN_PATIENT_INSTRUCTION       NUMBER(1),
PLAN_PATIENT_LETTER            NUMBER(1),
PLAN_PATIENT_LETTER_COMMENT    VARCHAR2(4000),
PLAN_PROCEDURE_DESCRIPTION     VARCHAR2(4000),
PLAN_RENAMEDAS                 VARCHAR2(50),
PLAN_REPORT_SHOW               NUMBER(1),
PLAN_SCHEDULED                 DATE,
PLAN_SHOW_IN_PROBLEM_DETAIL    NUMBER(1),
PLAN_SHOW_TESTHISTORY          NUMBER(1),
PLAN_SIG                       VARCHAR2(4000),
PLAN_SMART_LIST                NUMBER(1),
PLAN_SOURCE                    VARCHAR2(50),
PLAN_STATUS                    VARCHAR2(50),
PLAN_STATUS_PRIORITY           VARCHAR2(50),
PLAN_TASK                      NUMBER(1),
PLAN_TASK_CODE                 NUMBER,
PLAN_TIMING                    VARCHAR2(50),
PLAN_TITLE                     VARCHAR2(4000),
PLAN_TYPE                      VARCHAR2(50),
PLAN_USER_ID_ADDED             NUMBER,
PLAN_USER_ID_LAST_MODIFIED     NUMBER,
TAG_ORDER                      NUMBER,
TAG_CREATEDATE                 DATE DEFAULT sysdate  NOT NULL,
TAG_SYSTEMDATE                 DATE DEFAULT sysdate  NOT NULL,
TAG_SYSTEMUSER                 NUMBER NOT NULL
)
```

```
CREATE TABLE MEDICATIONS$
(
  MEDICATIONS$_CODE                NUMBER NOT NULL,
  VISITS_CODE                      NUMBER NOT NULL,
  MEDICATIONS$_TEXT                VARCHAR2(4000),
  MEDICATIONS$_PREV                NUMBER,
  FULL_SIG                         VARCHAR2(4000),
  MED_ACTIVITY                     VARCHAR2(50),
  MED_ADJUD_ALLERGY_TYPE           VARCHAR2(100),
  MED_ADJUD_ALLERGY_YESNO          VARCHAR2(50),
  MED_ADJUD_COMPLIANT_REASON       VARCHAR2(250),
  MED_ADJUD_COMPLIANT_YESNO        VARCHAR2(50),
  MED_ADJUD_EFFECTIVE_COMMENT      VARCHAR2(100),
  MED_ADJUD_EFFECTIVE_YESNO        VARCHAR2(50),
  MED_ADJUD_SIDEEFFECT_ADD_ALLER   NUMBER(1),
  MED_ADJUD_SIDEEFFECT_TYPE        VARCHAR2(250),
  MED_ADJUD_SIDEEFFECT_YESNO       VARCHAR2(50),
  MED_ADJUD_TEXT                   VARCHAR2(4000),
  MED_AKA                          VARCHAR2(500),
  MED_CODE                         VARCHAR2(100),
  MED_COMMENT                      CLOB,
  MED_CONTINUOUS                   NUMBER(1),
  MED_DATE_ADDED                   DATE,
  MED_DATE_LAST_MODIFIED           DATE,
  MED_DATE_RESTARTED               DATE,
  MED_DC_REASON                    VARCHAR2(50),
  MED_DOSE                         VARCHAR2(250),
  MED_DURATION                     NUMBER,
  MED_DURATION_STRING              VARCHAR2(4000),
  MED_DURATION_UNIT                VARCHAR2(50),
  MED_END_DATE                     DATE,
  MED_FORM                         VARCHAR2(50),
  MED_FREQ                         VARCHAR2(50),
  MED_GPI                          VARCHAR2(50),
  MED_HELD_REASON                  VARCHAR2(4000),
  MED_INCLUDE_AKA                  NUMBER(1),
  MED_INSTRUCTION                  VARCHAR2(4000),
  MED_INTAKE                       VARCHAR2(500),
  MED_INTAKE_UNITS                 VARCHAR2(100),
```

FIG. 14DD

```
MED_INTAKE_UNITS              VARCHAR2(100),
MED_LAST_REFILL_DATE          DATE,
MED_LEGEND                    VARCHAR2(4000),
MED_MATNO                     VARCHAR2(50),
MED_MODIFICATION              VARCHAR2(4000),
MED_NAME                      VARCHAR2(250),
MED_NEEDS_FOLLOWUP            NUMBER(1),
MED_NEWMEDICATION             NUMBER(1),
MED_OLD_REVISION              NUMBER(1),
MED_PACKAGING                 VARCHAR2(4000),
MED_PATIENT_INSTRUCTIONS      VARCHAR2(4000),
MED_PRINTSCRIPT               NUMBER(1),
MED_PRINT_PI                  NUMBER(1),
MED_PRN                       NUMBER(1),
MED_PRN_REASON                VARCHAR2(250),
MED_QUANTITY                  VARCHAR2(50),
MED_QUANTITY_UNIT             VARCHAR2(4000),
MED_REASON                    VARCHAR2(4000),
MED_REFILLS                   VARCHAR2(50),
MED_REFILL_QUANTITY           VARCHAR2(50),
MED_REPORT_SHOW               NUMBER(1),
MED_ROUTE                     VARCHAR2(50),
MED_SAMPLES_GIVEN             NUMBER(1),
MED_SCRIPT                    VARCHAR2(4000),
MED_SIDEEFFECT                VARCHAR2(50),
MED_SIGCOMMENT                VARCHAR2(500),
MED_SMART_LIST                NUMBER(1),
MED_SOURCE                    VARCHAR2(50),
MED_START_DATE                DATE,
MED_STATUS                    VARCHAR2(50),
MED_SUBSTITUTE                NUMBER(1),
MED_USER_ID_ADDED             NUMBER,
MED_USER_ID_LAST_MODIFIED     NUMBER,
MED_WARNING                   VARCHAR2(4000),
MED_WARNING_BOLD              NUMBER(1),
TAG_ORDER                     NUMBER,
TAG_CREATEDATE                DATE DEFAULT sysdate  NOT NULL,
TAG_SYSTEMDATE                DATE DEFAULT sysdate  NOT NULL,
TAG_SYSTEMUSER                NUMBER NOT NULL
)
```

55

LONGITUDINAL ELECTRONIC RECORD SYSTEM AND METHOD WITH PROBLEM DETERMINATION AND PLAN ORDERING

This application is a division of U.S. patent application Ser. No. 11/858,241, filed Sep. 20, 2007.

BACKGROUND OF THE INVENTION

1. Field of the Invention

The present invention is directed to a system and method for electronic record-keeping, organizing, and managing.

2. Description of the Related Art

Standards for healthcare patient record structures are failing to deliver on the promise for which they were first introduced and delivered. Record structure standards were created to allow exchange of information, but did not address the real need of the actual care of patients or the proper storage of patient information over time. Messaging standards have allowed the transfer of non-machine readable information, and terminology and information model standards have allowed for semantic interoperability.

Standards considered include:

CCR: The Continuity of Care Record is a patient health summary standard. It is a way to create flexible documents that contain the most relevant and timely core health information about a patient, and to send these electronically from one caregiver to another. It contains various sections such as patient demographics, insurance information, diagnosis and problem list, medications, allergies and care plan. It is a "snapshot" of a patient's health data at a point in time, and as such, does not address important issues related to the longitudinal patient medical record.

HL7 RIM: The Health Level 7 Reference Information Model. At the core of the HL7 version 3 standards development methodology is the Reference Information Model (RIM), which is a static object-oriented model in UML notation. The RIM serves as the source from which all specialized HL7 version 3 information models are derived and from which all HL7 data ultimately receives its meaning. This is to establish semantic interoperability across a vast and growing number of subject domains (e.g., laboratory, clinical health record data, problem- and goal-oriented care, public health, clinical research, etc.), which are loosely but critically related. The RIM was first conceived as a data model, where all data elements known from HL7 version 2 and some large electronic health record data models were put on a single information roadmap. This model has been under development since 1996, and has not yet received consensus from participating members—most HL7 data interchange uses version 2.3.1. The model is primarily geared toward support for administrative and financial patient data exchange and observation data exchange, but does not address longitudinal electronic patient medical record structures.

HL7 CDA: The HL7 Clinical Document Architecture (CDA) is a document markup standard that specifies the structure and semantics of "clinical documents" for the purpose of exchange. Similarly to CCR, this represents a "snapshot" of a patient's health data at a certain point in time, and does not address an overall design of longitudinal electronic patient medical record structure.

Care Record Summary (CRS): A special use case of the HL7 CDA used as a care record summary.

What is needed is a record format that addresses the issues presented above.

BRIEF SUMMARY OF THE INVENTION

A system and method for capturing the complete depth of information contained within data, in particular, how data elements exist and interact with each other over time. The system and method may be scalable, have congruency with published standards for medical data interoperability, answer day-to-day patient management workflow and be compliant with the Health Insurance Portability and Accountability Act (HIPAA).

In one embodiment, the present invention may be a method for keeping, organizing and managing electronic records, comprising: generating a first instance of data objects having data elements during a first encounter, the data elements further comprising a first instance identifier and temporal identifiers; linking a data object in the first instance to a summarization reference with a pointer; creating an additional instance of data objects having data elements during a later encounter, the additional data elements further comprising an additional instance identifier and temporal identifiers; and providing continuity for the first instance data objects over time. Continuity may be accomplished by tracking a relationship between the first instance data object a data object of the additional instance, as well as repointing the pointer to point between the summarization reference and the additional instance data object. Moreover, the additional instance data object may be a revision of the first instance data object. In addition, tracking may be achieved by back-linking the revision to the first instance data object. The method may also include diagnosing a problem and formulating a plan based on information contained in the first instance of data objects; and treating or managing the problem and reviewing the plan based on information contained in the additional instance of data objects. Moreover, the method may comprise relating at least one first instance data object with at least one additional data object in said instance of data objects.

In another embodiment, the method may comprise collecting visit level information for administrative use, the visit level information comprising at least one of the following: demographic information, subjective information, objective information, assessment information and plan information; collecting and maintaining a list of items relating to an individual; assuming management of follow up items; creating a revision history of the list of items over time; implementing a privacy protocol; providing a task-based workflow; supporting secure data exchange; and supporting resource-based tasking. In this embodiment, the implementation of the privacy protocol may be accomplished by: providing an audit of database activity; providing robust security; providing role-based record access; and encrypting sensitive data.

In still another embodiment, the method present invention may be a method for longitudinal electronic record-keeping having the steps of: storing discrete data elements relating to an individual; creating a new record for a visit, wherein the new record is a wrapper for the discrete data elements captured during the visit; collecting a group of records for the individual, having additional discrete data elements and at least one identifier reference; determining a problem based on the additional discrete data elements in the group of records and the visit; ordering a plan motivated by the problem; repeating the creating, determining and ordering steps for a subsequent visit to document additional problems and plans; following up on the problems and plans during the subsequent visit; generating historical linkages of the problems and plans; and maintaining a current list of problems and plans that are relevant to the individual. During or following the subsequent visit, the discrete data elements captured during an earlier visit may be elevated to a problem or plan. The method may also include closing each record at the end of each visit and preventing entry of further discrete data elements to each record after the record is closed. In addition, a task may be created at the completion of each visit and the method may be based on a task-driven workflow that may require producing a task calendar of events, functional data review and task production. Moreover, a new or existing task list may be used to trigger a new task or a reminder. The method may also allow a user to transport data elements from one system to another generally without incurring data loss.

In addition to the method, the present invention also comprises a system for carrying out the method. In one embodiment, the system may have a user interface module or layer; a business logic module or layer; at least one data access layer; a data storage system layer; data storage functions; and a communication layer to external systems. The system may also have a visualization layer supported by one or more of the other layers. These layers may be used to minimize the dependencies between data elements. Using the inventive system, data may be translated into tables, indexes, primary key constraints, foreign key constraints or triggers for storage.

In another embodiment, the system may further have controlled vocabulary modules, such as codified, controlled medical vocabularies. These controlled vocabulary modules, along with other system elements may reduce or alleviate a need for data cleansing.

DETAILED DESCRIPTION OF THE INVENTION

Figure 1:
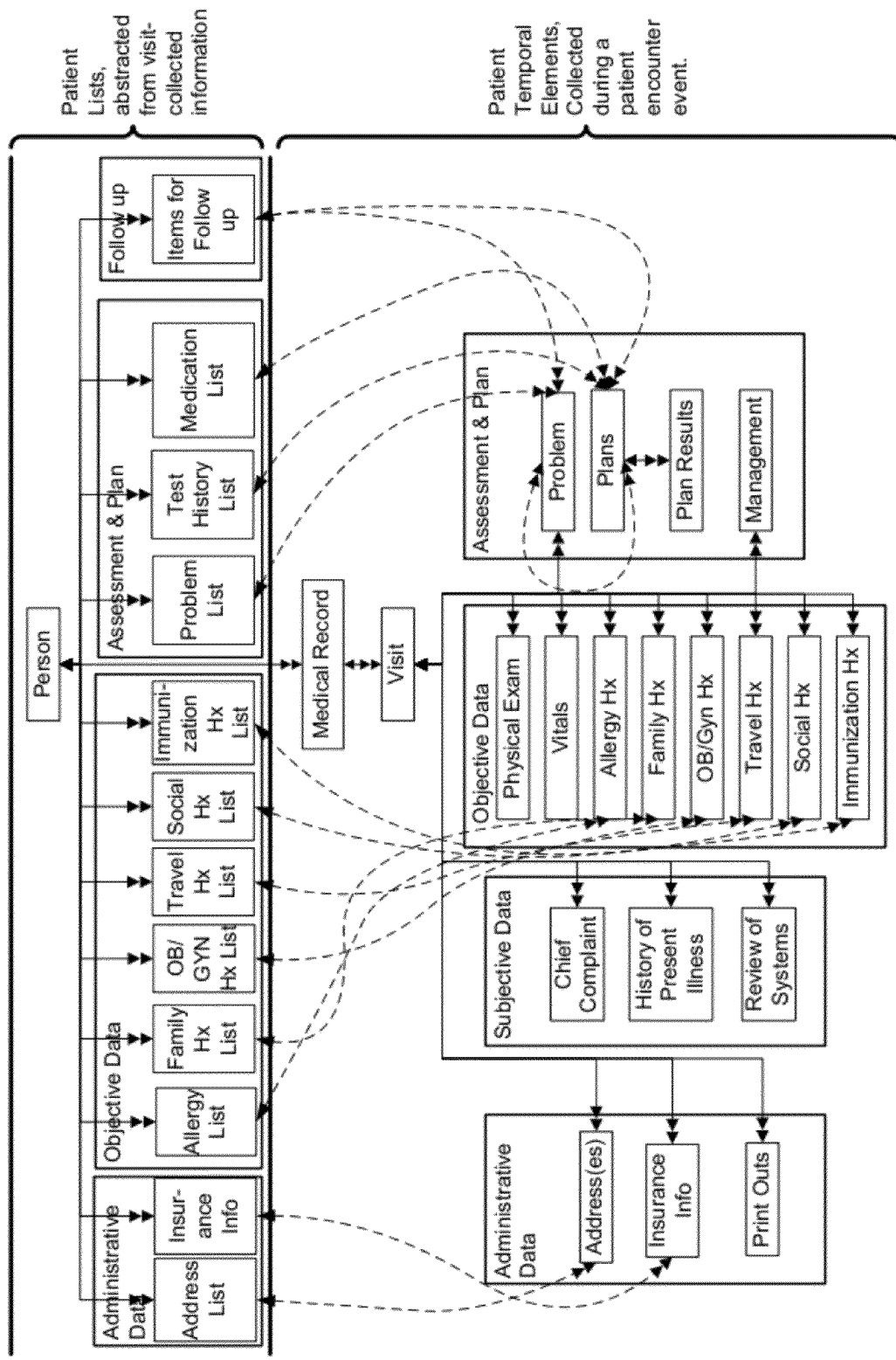
FIG. 1 is a schematic of one embodiment of a longitudinal electronic medical record.

A system and method for longitudinal electronic record-keeping, organizing, and managing. Although the system and method have applicability to a broad range of disciplines in which data or conditions are recorded and evaluated over time, they will be described herein with specific suitability to the medical field. In this context, method and system are shown in the preferred embodiment of a longitudinal electronic medical record (LEMR).

I. Requirements for a Longitudinal Electronic Medical Record

The written medical history of a patient is a longitudinal record of what has happened to the patient since birth. It may chronicle diseases, major and minor illnesses, as well as growth milestones. By documenting everything that has happened to the patient prior to the current visit, it often give clues to current disease states and helps guide the clinician in either the diagnosis of new problems or the treatment and/or management of older ones. A LEMR aims to achieve that goal. It is a record of patient health information generated by one or more encounters in any care delivery setting, by one or more care providers. Included in this information may be patient demographics, chief complaints, physical exams, review of systems, progress notes, problems, medications, plans, vital signs, history information (including past medical, surgical, medication, test, social, travel, immunization, obstetric, growth chart and developmental history), laboratory data, SOAP notes, radiology reports, genetic information, scanned documents, referral documents, as well as other information commonly known in the art.

The LEMR should automate and streamline the clinician's workflow. It may have the ability to generate a complete record of a clinical patient encounter, as well as to support other care-related activities directly or indirectly including evidence-based decision support, quality management, and outcomes reporting.

An important concept behind the LEMR is to show data element continuity and the relationships between elements generated in multiple instances, in other words, show a patient data point over time, and also show this data point in relation to other data points. Furthermore, an element should be considered polymorphic. For example, while element X may first be identified as a chief complaint, element X may be later elevated to a patient problem and then later be considered past medical history. An element first identified as a plan may be updated or modified. An element initially declared as a medication may be retired, thus becoming medication history. Moreover, it may also eventually be identified as allergy. In this manner, the LEMR element is important in itself, but the lifecycle of the element is equally important.

As a result, a LEMR becomes a web of relationships, with a prevalent axis of time. The LEMR may capture information patient visit by patient visit, note during which visit the information is captured, and relate all such information to previous and future patient visits. In one variation, a "visit" may be equivalent to a patient encounter, or a patient episode of care, etc. In addition to this relative capacity, the LEMR may also be able to summarize the patient's current health status in a single view such as a patient face sheet.

Elements within a LEMR may be discrete and codified. For example, a SOAP note as a text memo may not be a principal constituent of an LEMR, but many elements participating in capturing patient SOAP note information may be LEMR primary elements. The SOAP or progress note built from these elements is simply a data collection byproduct.

In one embodiment, a LEMR is supported by some form of office workflow. For example, without additional "cues," a LEMR may not specify the next patient encounter. However, the LEMR design may include the ability to setup and collect information pointers directed at other activities within the LEMR. Such information pointers, also referred to as "tasks," may either be created before completing the patient encounter or by examining the state of a LEMR using Arden-syntax rules. This information pointer list may become the basis for care providers to effectively and accurately provide care to a patient.

Moreover, the LEMR is a data collection device that may provide the following functions:

Collect visit level information for administrative use such as demographic information, as well as clinical data such as subjective, objective, assessment and plan information.

Assume the management of follow up items. Any patient visit after the first patient visit should be geared toward following up on formulated or ordered plans from the previous visit.

Collect and maintain a list of patient items such as: problem list, medication list, plan list, etc.

Maintain item versioning: create over time a revision history of clinical items.

Implement a privacy protocol, such as HIPAA, which may include:

Providing an audit of all database activity, for insertions, updates and deletions. In other words, maintain "who did what and when."

Providing robust security. One layer (ADM, the bottom layer) may be central and may provide data and enforce security. All subsequent layers may be access layers, such as intelligent data access, business rule layer, presentation layer, interface layer(s), etc. In this configuration, the idea may be to divide and conquer, i.e. each layer may have specific responsibilities, not interfering with other layers, but combining to enhance security.

Providing role-based record access. The lowest layer (ADM) may define storage, security and data access roles. Roles may be defined to group together privileges: for example, being an administrator, or being a form application user, or being a report writer for all associated rights. Users may then be created and associated with roles. Applications may react on user login to enable a feature subject to authorization in accordance with a user's role, or possibly deny access to resources.

Forcing encryption on patient-sensitive data, both within the backend database and via any interface-type transmissions.

Moreover, the LEMR may provide a task-based workflow. Tasks are patient care workflow checkpoints. Completing a task may trigger the creation of further tasks and tasks may also be created by evaluating the current state of the patient using Arden Syntax-like rules, for example.

Support Secure Data Exchange.

Provide support for resource-based scheduling for appointments, tests, and other resource-based tasking.

2. Blueprint for a Standard Model

Turning to FIG. 1, a schematic of one embodiment of a LEMR is shown. LEMR of FIG. 1 may be organized around the principles of patient, medical record, visit and follow-up, as described below:

Patient

The most basic unit of the LEMR may be the patient. A patient has discrete data elements such as: last name, first name, date of birth, social security number, language, maiden name, ethnicity, middle name, patient status, and suffix. These are elements that are unlikely to change over time, or which changes are not tracked, and which may be used for identification. In this embodiment, patient-specific elements that do change are tracked under the VISIT section, as explained below.

Medical Record

A patient is likely to have one or more medical records, scattered throughout different inpatient and outpatient settings. The medical record element is the collection of records for the patient. Each medical record may have discrete elements such as a Medical Record Number (MRN) and a facility identifier reference.

Visit

The visit is the level that captures data from a patient clinical encounter. Each new clinical encounter warrants a new visit record. A visit captures information that is either new or changed at the time of the encounter. Each visit record has discrete data elements and may include: account number, admission/encounter date and type, gender, marital status, patient type, religion, visit type, and other elements that likely change over time. As such, they may be given a time stamp or other form of temporal identifier to describe when they are entered. In addition, the visit may also be a wrapper for many visit-oriented data elements, such as: administrative, subjective, objective, and assessment and plan data.

Administrative data may be data elements associated with visit-related patient demographic information and visit-administration information. Among the information that may comprise administrative data are:

Patient address list: a list of patient addresses at the time of the visit. An address may comprise street, city, state, zip code, telephone, email, and address type.

Patient insurance information: the patient primary and secondary insurance details. This information plays an important role for data interchange when placing orders with laboratory systems.

Print outs: these are the documents as text streams that have been created and printed during a patient encounter or other interactions with the patient. Printout storage may comprise the document itself and a document type.

Subjective data may be data collected in generally non-codified form from the patient, as expressed by the patient. Among the information that may comprise subjective data are:

Chief Complaint: a short textual description of the reason for the encounter.

History of present illness: story-like record of the patient's history of this current complaint.

Review of systems: a structured laundry list of pertinent positives and negatives (signs, symptoms and history items).

Objective data may be data collected in codified form by examining the patient, or through other forms of data collection or chart review. Among the information that may comprise objective data are:

Physical Exam: the description of the patient's physical appearance and response to various stimuli, which is part of the clinician's examination.

Vital Signs: may include data elements such as Blood Pressure, Pulse, Respirations, Weight, Height, and Oxygen Saturation.

Allergy History: may include both medication and non-medications that have caused adverse reactions to the patient and the form of the reaction.

Family History: may include pertinent medical and genetic history of family members as well as the current state of their health. This can include lists by family member, by disease, or as graphs.

OB/GYN History: may include obstetrical and gynecological history for women.

Travel History: may include descriptions of places traveled to and other potential exposures that can predispose the patient to disease or other conditions.

Social History: may include data about social exposures such as tobacco, alcohol and drug use, as well as other elements such as education, occupation and living arrangements.

Immunization History: may include data about preventative immunizations.

Assessment & Plan data may be additional data captured within the visit level and may comprise problems & assessment and plans related to those problems:

Problems, problem determination, and problem assessment or management are additional aspects of the LEMR. In one embodiment, the system may manage problem lifecycle, which captures a timeline of problem management, including all problem revisions, and plan relationships, which capture the reasoning or rationale for ordering a plan. One or many problems may have motivated ordering a particular plan, while a single problem may motivate ordering several plans, thus establishing a many-to-many relationship between problems and plans.

Problem elements may comprise: source and code (of the controlled medical vocabulary), title, description, comment, onset and end date, activity, status, and severity.

There may be many different types of plans, including: orders (laboratory or procedure orders), referrals, medications, discharge instructions (for example patient education materials), and other courses of action known in the art. In addition, plans may have one or multiple relationships to problems. The link between the plan and the patient's problem or reason for the plan may be significant in performing decision support computations (e.g. medical necessity checking), and to point out health, workflow, and resource allocation issues that may occur at a later point in time.

Plan elements comprise: source and code (of the controlled medical vocabulary), title, description, comment, onset and end date, and status.

Medications plan elements may be substantially more complex and include: medication name, dosage, unit, route, form, intake and intake unit, frequency, quantity, refill information, whether a patient education pamphlet was given out, prescription details to the patient, and comments.

In the case where plans are laboratory or procedure orders, the plan result child element may be the location for capturing the results of the lab or procedure, in detail.

A plan or order may be documented either as a performable order (for example, 'Venipuncture', 'Dye Injection'), or an order result (actual value for a laboratory result, a radiology finding, or a finding interpretation), or a document order (for example surgical history items), or a charge order (for example a billing code associated with a visit event).

A plan may be supported by a task, or a set of tasks. More specifically, tasks may be dependent or independent of each other. Dependent tasks may be considered hierarchical: a task is satisfied (completed, or closed) when all child tasks are satisfied.

Follow Up List

The concept of follow up is important to a longitudinal electronic record. Elements of follow up may be found in Dr. Kim Charles Meyers' concept of problem resolution workflow, which is embodied in copending U.S. patent application Ser. No. 11/436,010 "Problem Solving Process Based Computing," filed on May 17, 2006, claiming the benefit of U.S. Provisional Application 60/681,937, filed May 17, 2005 and which contents are incorporated herein by reference.

The intent of the patient medical record is to provide a framework for patient problem resolution, and a patient encounter should start with discussing items from the previous visits (problem status, plan orders & results, medication prescriptions). As a corollary, the follow up list is the list of items that should be followed up on sometime in the future, and, like the visit, may include items such as problems and plans.

Supporting Longitudinal care

The LEMR model focuses on assessment and plan as central elements within the longitudinal care delivery process and provides tracking of these actions by problems. Assessment and plan may be attached to single or multiple problems. The model allows any item from the patient's data to be elevated to the problem list. This LEMR model also allows for software applications to harmonize the presentation layers around the problem and results that need to be monitored in longitudinal care delivery.

3. Problem Management Workflow

Figure 2:
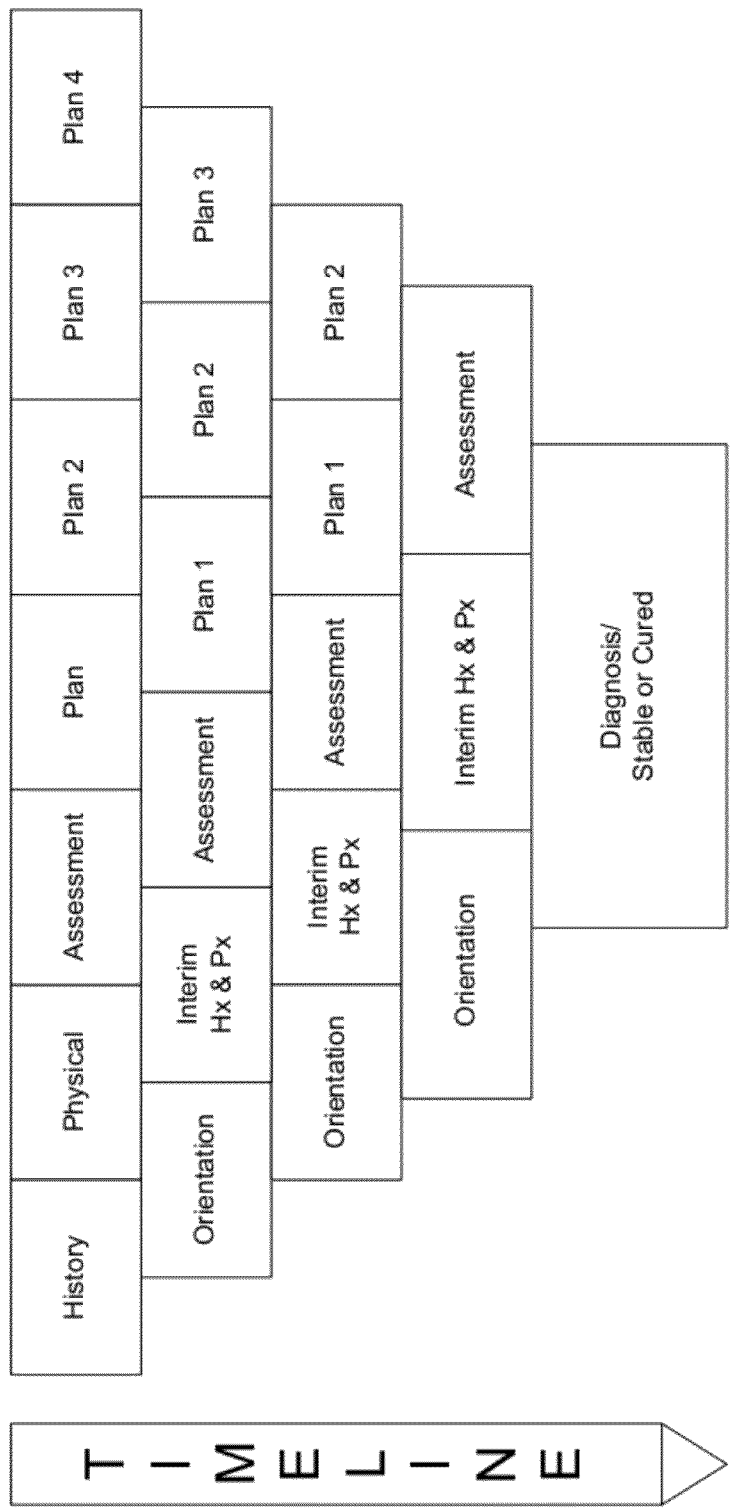
FIG. 2 is a diagram of a problem management workflow taken over several visits.

Turning to FIG. 2, a problem management workflow is shown. As can be seen in FIG. 2, the initial visit may comprise Subjective (History), Objective (Physical Exam) and Assessment and Plans sections. In a preferred embodiment, the next visit is started with a patient orientation which may includes items from all four categories, and an assessment of the success or failure of the plans from the prior visit. Further visits may repeat this process with the intended basic goal of addressing patient problems by managing, and eventually resolving the problems.

Electronic Medical/Health Record vendors frequently either neglect to recognize or are incapable of handling the follow-up visit. The delivery of a comprehensive orientation model requires a commitment to retrieve and debrief prior visit plans. As a technical point, most standard relational database models are not well suited to deliver this simple problem solving theme.

4. Patient Current Lists

To this point, the LEMR has been presented as a patient-specific collection of medical record visits over time. However, it may also be quickly able to display the current state of the patient. For example, patient problems within visits may be collected and historical linkages of problem revisions over time may be maintained, but the list of patient problems that are current and relevant to the patient care status must also be maintained. This reasoning is applied to the following lists:

Address List.

Patient current addresses may be updated if necessary at the start of each patient encounter in order to keep a list of active patient addresses such as home, office, etc.

Insurance Information List.

Similarly to the patient address list, an LEMR should keep an up-to-date list of patient insurance(s). This list is important to the billing aspect of a patient medical record, and is also key to submitting laboratory orders using HL-7.

Allergy List.

The list of current patient allergies.

History Lists: Family History List, OB/GYN List, Travel History List, Social History List, Immunization History List, Test History List.

The list of patient historical items, by history sections.

Problem List.

The list of relevant patient problems. This list may be rather involved. For example some of the previously captured patient visit problems may be listed, and within the listed problems, problems may be listed by status (active, inactive, retired, and superseded, etc.). Moreover, one problem may have led to the creation of a later problem, or treatment for one problem may impact the status of another problem.

Test History List.

The list of plans ordered for the patient. This list may grow to be quite large over time, as it is the reference of plans—and results—over the entire history of the patient's care. Some tests may be deemed less important and archived or their display suppressed; others may be prioritized and displayed prominently.

Medication List.

Medications may be either acute or chronic. Some are recorded only once, while others are refilled many times. It is important to store the medication with a state as a function of status (active, stopped, continued, etc) and medication start/end date.

5. Portable Patient File Concept

In one embodiment, an important additional requirement of an LEMR model is the ability to transport patient data from one system to another, generally without incurring data loss. This concept may be supported by Portable Patient Files, as a mechanism to define the XML format as the pattern depicted in FIG. 1, which may then be used for file instantiation during patient database export or import. Format of the Portable Patient File may be expressed as an XML file, and the format of the XML file may be driven by the definition of the Meta Data in an adaptive data environment, as discussed in the Storage Mechanisms section below. The content of a Portable Patient File may comprise all information attached to a patient.

6. Patient Oriented Tasking

FIG. 1 may allude to patient workflow as it mainly represents a methodology for organizing patient information. A patient care treatment protocol may be represented as a patient data life cycle over time; triggering events for patient care independent of the inpatient or outpatient setting, which may be supported with a task-driven work flow. This task-driven workflow may be based first on producing a task calendar of patient care events, and second, on regularly proceeding to patient data functional review, supported by Arden syntax-like capability to produce care protocol driven tasks. From a care provider standpoint, good patient care often requires reminders, from an existing task list on all patients, or via computational means that may trigger a task or reminder given a particular set of circumstances.

Patient Task

One or more patient tasks may be created at the end of a patient encounter, for example:

Next care encounter with patient;
Plan order result review and phone call to patient;
Next physical exam;
Next laboratory test; etc.
Computational Means for Task Creations A downside to creating tasks at the end of a patient encounter may be that conditions change. For example, a laboratory result may: trigger calling the patient sooner, ordering follow up laboratory orders, or simply reassessing the patient state given the new evidence.

The logic for such computation may be rather straightforward: if [condition] then [task action [given no overlap]]. This is well achieved using an Arden Syntax-powered task engine. For example, one could conceive the following computations:

Has the patient had a cholesterol check within the past year?

If the patient has diabetes mellitus and either hypertension (or two blood pressures higher than 140/90), is the patient on an Angiotensin Converting Enzyme Inhibitor (ACE-I)?

Patient Scheduling

Patient scheduling comprises finding a time slot where the patient care encounter will occur with the care provider. In simplistic situations, for an outpatient family practice with matched sets of physicians, nurses and examinations rooms, a large sheet of paper may work. For more complex cases, with shared resources, ranging from shared examinations rooms to multi-facility, multi-model, multi-procedure office settings supporting complex scheduling, a professional patient scheduling system may be necessary. In other words, patient scheduling may be resource-based scheduling for appointments, tests, and other resource-based tasking.

There are multiple ways in which patient scheduling may occur. Wave scheduling may be highly favorable to the care provider, but is rather disrespectful to patients. In wave scheduling, many patients are all told to come at a given time. Once there, they are seen on a "first-come, first-served" basis. Loading the patients at the front end of the day may optimize the efficiency of a staff by guaranteeing there is never a lull in patient flow. However, while this may be good for productivity, it is unpopular with patients, some of whom may have to wait several hours to be seen, despite having arrived on time for their appointments.

Time-slot scheduling, as opposed to wave scheduling is actually a resource based scheduling algorithm. All resources—physicians, nurses, staff type, patient, examination room, equipment unit and type, modality, facility, etc—have constraints, availability, and dependencies, which ultimately drive patient scheduling. For example, nuclear imaging may require an injection, followed by a first image taken at a precise time, followed by a second image at a precise interval of time. Such multi-modal procedure may involve different equipment (maybe mobile), different staff or staff type, and room reservations.

After computations, an agreed-upon scheduled time may morph into one or more patient tasks, assigned to one or several care providers.

7. Document View Model: Example of Face Sheet View

Patient medical record software is complex software. Creating and maintaining such software may be achieved using software layers in order to minimize dependencies. Following a Document View model, the patient face sheet is a visualization layer that taps into and is supported by services provided by one or more lower level layers. In other words, a common set of layers may support one or more view layers, for example for different care provider roles across the enterprise.

Figure 3:
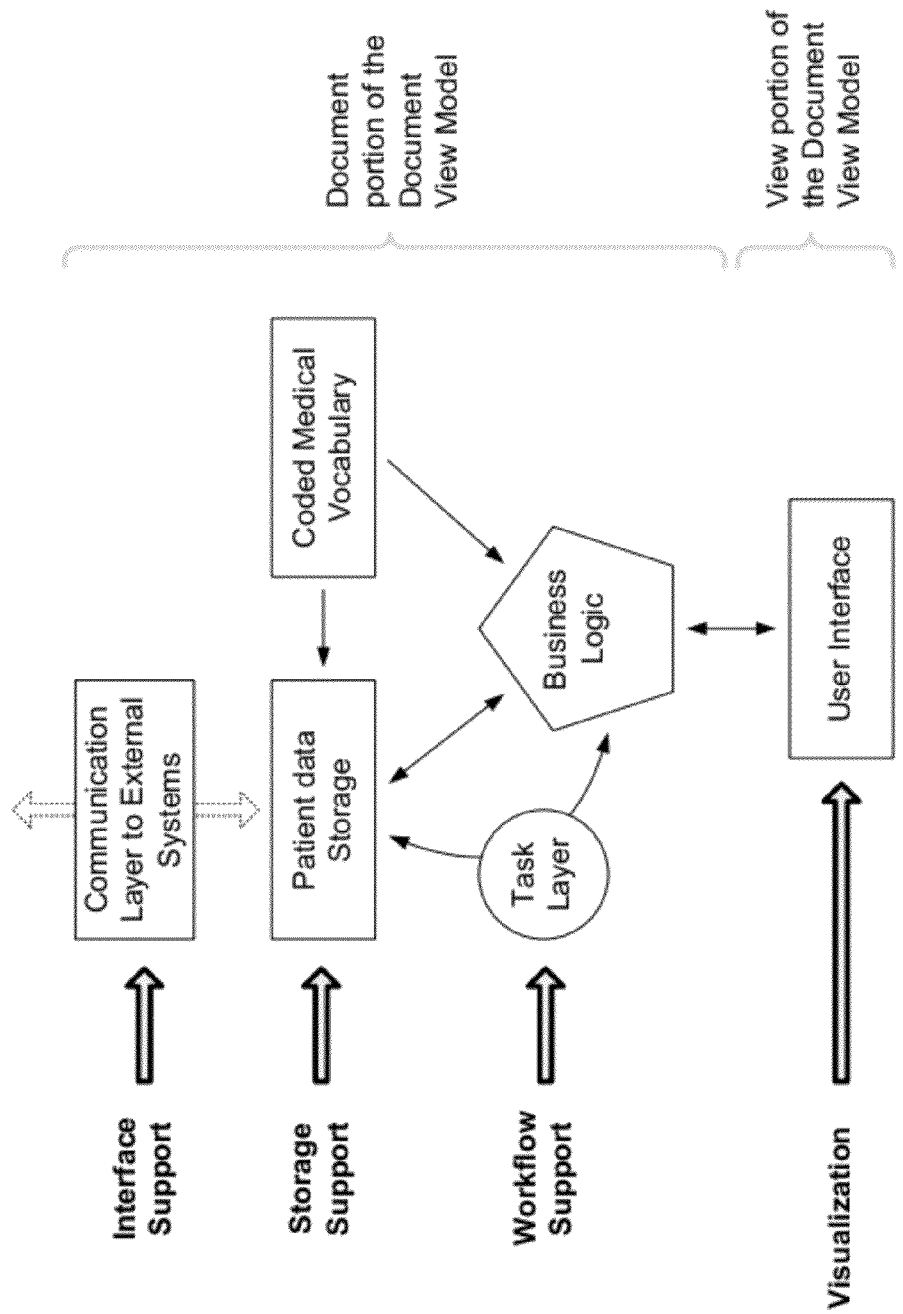
FIG. 3 is an example of a document view of the software layers of the inventive system and method.

FIG. 3 shows an example of document view software layering. User Interface and Business Logic layers may work in concert to consume services provided by the Patient Data Storage layer, Task layer and Coded Medical Vocabulary service layer.

Figure 4:
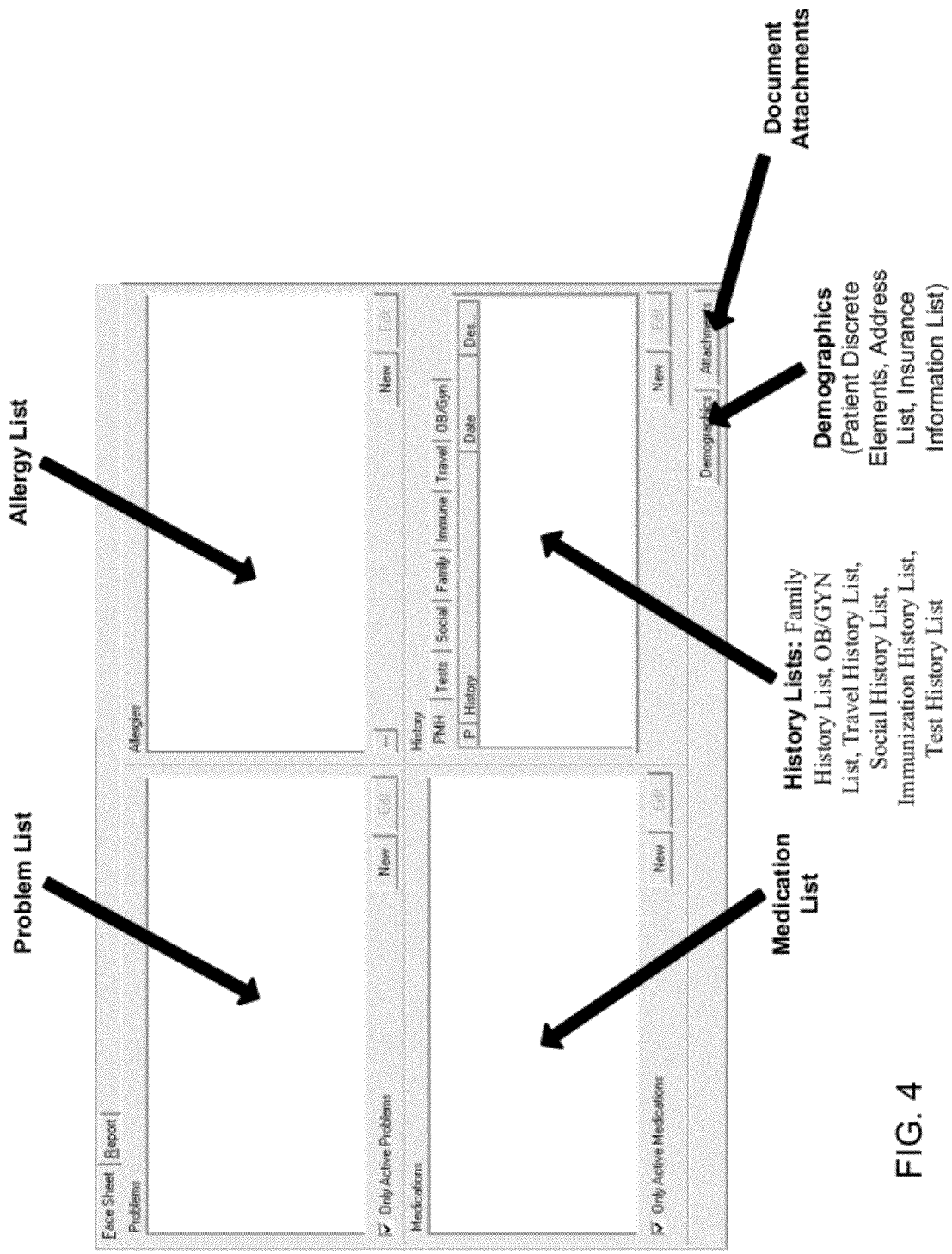
FIG. 4 is a functional face sheet exhibiting patient lists as described in FIG. 1.

Turning to FIG. 4, a function face sheet exhibiting patient lists as described in FIG. 1 is shown. This face sheet focuses on patient care issues and may present the following advantages:

Patient problems, Allergies, and Medications are clearly displayed for a quick review.

All patient history lists are one click away, by selecting the corresponding tab sheet within the history quadrant.

Editing and reviewing demographics information is one step away.

All quadrant items can be created and edited using 'local' New and Edit buttons.

Any alert-triggering items will be highlighted (including at a minimum decision-support rules, and possibly including any other business rules).

The face sheet may show a user what is current for a given patient. However, it may also be capable of showing a patient's historical information. Moreover, the face sheet may be used with a standard vocabulary, which may allow for easier interoperability among various providers, e.g. The software behind the face sheet may also recognize several common phrases ("chest pains", e.g.) and know what code to give them or how to code them.

8. Role of Controlled Medical Vocabularies

Successful implementation of a comprehensive LEMR may lay in the implementation of a controlled medical vocabulary. It may be important to capture the meaning of the problem and its classification within medical concepts. It also may be important that this meaning is preserved and used to repeat a successful care plan. In other words, controlled medical vocabularies may be at the core of an appropriately designed and implemented patient medical record: all parts—problem, medication, plan, history item, even subjective findings—may be tagged with a source vocabulary, and a code internal to that source vocabulary. If this controlled medical vocabulary is an interface terminology mapped to reference and administrative terminologies, the benefits available afterward may include:

Providing billing code(s) for the financial systems downstream.

Populating decision support systems with patient information, such as medication indications, medication contraindications, allergy checking and drug-to-drug, drug-to-disease interactions.

Performing real-time queries against trusted clinical reference materials, directly from patient health records.

Manipulating and reviewing information for quality analysis, outcomes, research, and strategic planning, and Translating provider-entered problems into administrative codes, coder-specific language, and patient-friendly terms automatically.

II. Longitudinal Electronic Medical Record Architecture

Figure 5:
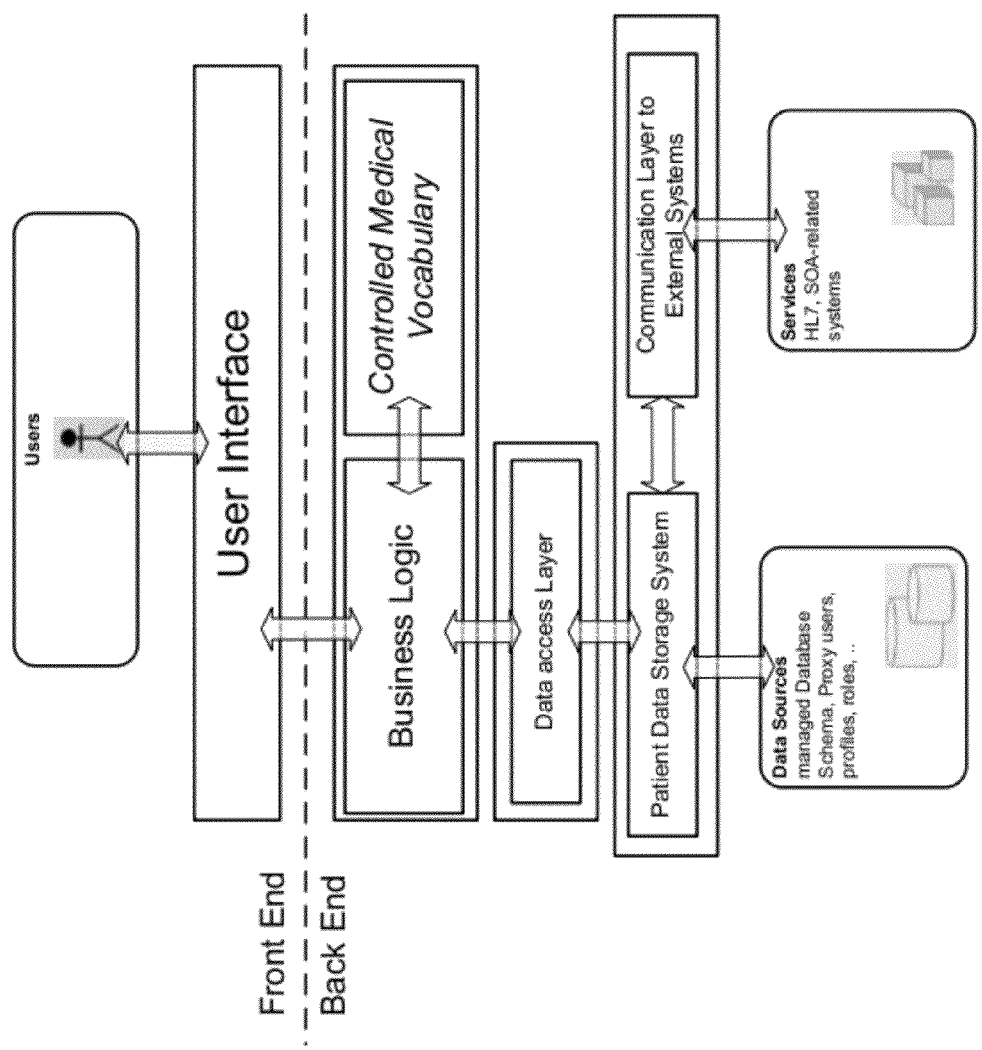
FIG. 5 is an example of an electronic medical record component view of the inventive system and method.

FIG. 5 depicts a common electronic medical record architecture of the inventive method and system, supporting the basic precepts for a fully functional physician electronic medical record. From a high level standpoint, the architecture may comprise a 'User Interface', patient data storage services, business logic, possibly Controlled Medical Vocabulary services, and interfaces.

The foundation of a sound electronic medical record application may reside around back end services; the type of subsystems that may not be easily visible to end users. End users are mostly exposed to the user interface—a thin or thick client, and back-end services, while generally omnipresent, may be presented only sporadically to the user. FIG. 5 shows EMR Generic System components and their relationships in context of each others.

As can be seen in FIG. 5, these components may comprise:

User Interface Module/Layer.

This module may represent how a role-based system allows users to interact with data, work flow and tasks, following defined business logic. In other words, this is the set of screens that is available to users to see and interact with.

Business Logic Module/Layer.

The business logic modules are the layers of software that isolate the user interface presentation logic from data access & storage implementation instructions. This layer defines "how the application works." This layer is where the true logic of the application is encapsulated.

Data Access Layer.

The data access layer is a mechanical layer. It may be best implemented when automatically derived from the patient data storage system. It usually reflects a "CRUD"—create, read, update, delete—approach at the very basic level, and may incorporate caching algorithms.

Patient Data Storage System Module/Layer.

This may be considered the central element of the EMR. The module may assume the functions of creation and maintenance of data access, security enforcement and audit of data interactions.

The patient data storage system module/layer may be the lowest layer. It may be the layer that controls storage, security—for data access control—and data access roles. It may be a one-point of access, such that generally all subsequent layers may be required to authenticate against this layer to gain privilege(s) to resources. In this way, security may be maintained generally independently of system architecture. In addition, this module/layer may also be the layer where access audit is performed. These features and functions may be consistent with HIPAA, where the main goal may not be to prevent access, but rather to guarantee data access by role, after authentication, and keep an access audit log.

Controlled Medical Vocabulary (CMV) Modules.

Refer to the "Role of Controlled Medical Vocabularies" section, discussed above, for more information.

Data Storage Functions.

Refer to the "Storage Mechanisms" section, discussed below, for more information.

Communication Layer to External Systems.

LEMRs may be ineffective without interfaces to external systems. Such systems may include order messaging/results (laboratories, pharmacies, radiology, etc), patient admission/discharge/transfer (ADT), and patient financial applications as the most frequently interfaced applications.

The inventive system and method may use these modules or layers and functions to translate data into tables, indexes, primary and foreign key constraints or triggers for storage of the data.

Figure 6:
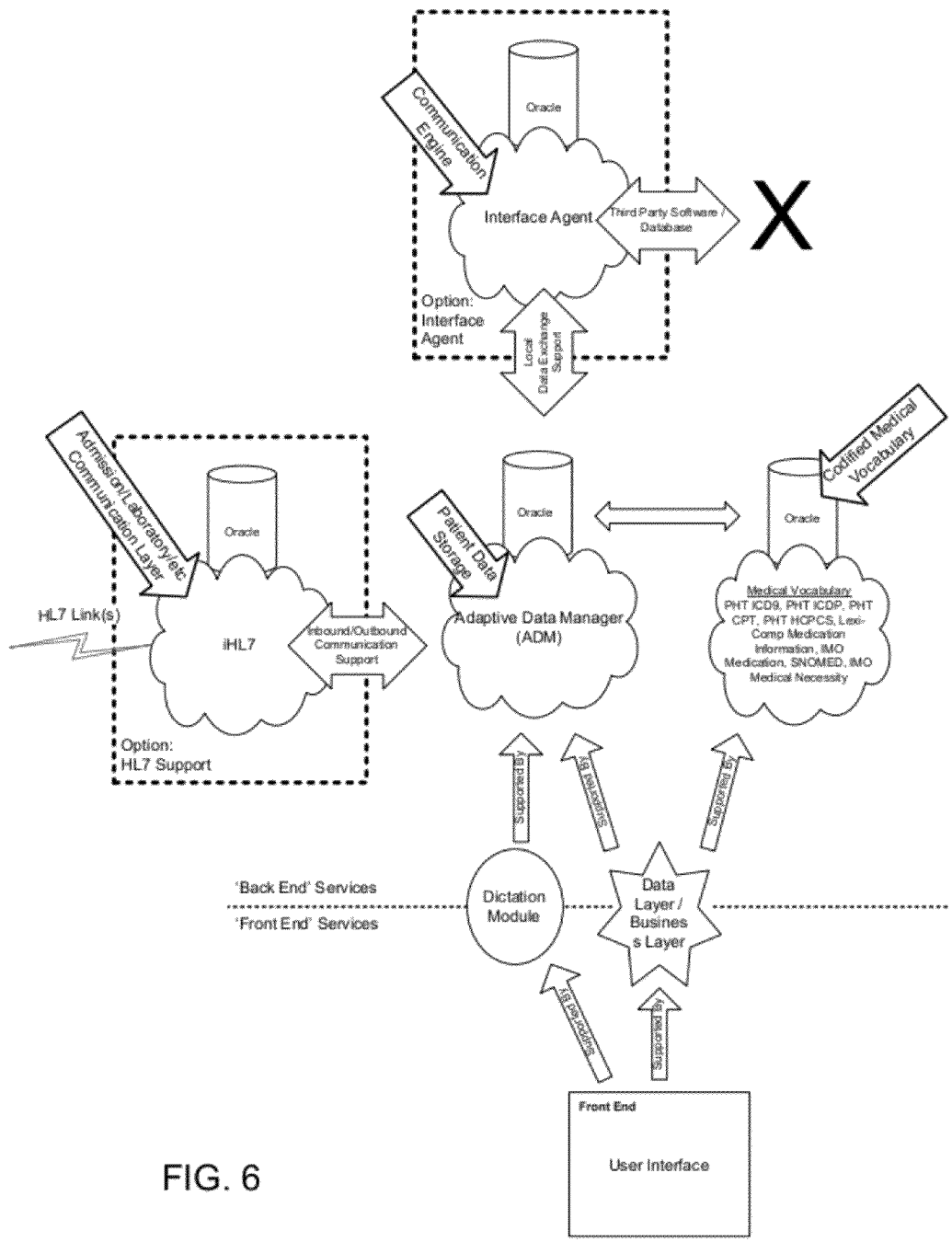
FIG. 6 is a software engineering view of one embodiment of the architecture of the inventive electronic medical record system and method.

FIG. 6 shows one embodiment of EMR System components, from a software engineering standpoint. This figure emphasizes the following additional system functions, although additional functions may be available:

Interface modules, supported by iHL7 for HL7-driven transactions and by Interface Agent (IA), for web services-driven transactions.

Business layer and data access layers. Such layers may be achieved using web services, COM+ objects, Java beans. The emphasis is on what will be most effective in the target environment.

User interface. Presentation technologies may comprise thin or thick client architectures, even though AJAX toolset recent advances tend to blur the line between thick and thin presentation technologies.

Dictation Module. The Dictation service is a service which transforms a sound wave file into text. Additionally, the text may be first tagged with Controlled Medical Vocabulary (CMV) terms, and secondly, CMV terms may be assigned to the appropriate section of the medical record encounter.

1. Storage Mechanisms

It is commonly estimated that over 80% of the software engineering time spent building an EMR is spent building a storage device, data access layer, and security layer. One example of a data management solution to this issue is Intelligent Medical Objects' (IMO) Adaptive Data Manager™ (ADM) as represented in the commonly-owned, co-pending U.S. patent application Ser. No. 11/065,600, filed Feb. 24, 2005, which is a continuation-in-part of U.S. patent application Ser. No. 09/997,723, filed Nov. 30, 2001 and issued as U.S. Pat. No. 6,904,432 on Jun. 7, 2005, the contents of both which are incorporated herein by reference. It is both a back-end information storage infrastructure, and a flexible development environment aimed at managing complex data storage. ADM is aimed at managing complexity: the data model is expressed in terms that any data analyst can understand, while database complexities are handled reliably and consistently by ADM. ADM is:

Based on a Meta data manager concept: the organization of the data itself (the Meta data) is described to ADM (prior to any collection of data). The Meta data Manager encloses definitions of Meta data elements as well as the relationships among these meta data elements.

An open-architecture system: it is implemented using Oracle standard features, and security is handled using proxy users, roles and profiles.

An implementation of HIPAA, without additional overhead. Security and role-driven functions are prevalent throughout ADM. User action Audit is pervasive and omnipresent.

A notable point of this design is information storage location. Information may be semantically expressed as:

Discrete elements, or values, such as the value for the patient last name.

Containers as groups of values, which functionally belong to the same information concept, such as a patient having many values for patient last name, first name, date of birth, social security number, etc.

Containers may be specialized as Container arrays: a patient may have one or several visits, whereas visit containers are array indexed.

The relationships between containers and arrays.

Containers and arrays revision information.

Task information, exclusively supporting workflow, whereas containers and arrays do not store workflow state.

Summarization of the record, which may be referred to as patients lists. These lists, such as patient problem list and patient medication list, gather items from disparate patient care events and are referred to as virtual arrays. In effect, by adding virtual lists, the information science model is elevated from a tree structure to a graph structure.

Creating, modifying or deleting a container, container array item or discrete element will generate an audit trail with author, date and previous value.

Practically, ADM was designed to handle complexity and ease of development from a developer standpoint. ADM resolved, and other data management solutions may resolve, the following issues:

Directed Graph Database Storage.

ADM is based on directed graphs, instantiated in a relational database. Accessing and modifying data in a directed graph is a NP-Complete problem. Therefore, when loading data from a directed graph, it may be necessary to ask how much data should be loaded, and when should the loading of data stop? This simple assertion has tremendous impact on performance.

Concurrency Management.

Compounding the issues presented with directed graph database storage, letting two or more users edit the same area of information may raise issues of data accuracy, data reload, and impact on performance. NP-Complete algorithmic issues related to database storage of data modeled as a directed graph may have the greatest impact on concurrency management, the most important question being "where should we stop reloading data that might have been changed?"

2. Additional Design Considerations

Containers and Container arrays encapsulate groups or discrete elements, child containers and container arrays. In effect, a tree of relationships with nodes as Containers and Container arrays, leaves as discrete elements, and edges as parent-child relationships between Containers, Container arrays and discrete elements is defined. Modifying any Containers, Container arrays and discrete elements may generate audit trails; therefore, it may be part of the design effort to intelligently organize Containers, Container arrays and discrete elements according to the functions of such elements. For example, we may assume that last name, first name, and SSN may be discrete elements belonging to the person container, while experience has shown that a person's gender is optimally designed as a child of the visit array container.

3. Reporting and Data Extraction

ADM assists with data harvesting: ADM allows creation of Meta views, as superset constructs that rely on the Meta data. For example, a simple electronic medical record for collecting immunization information for pediatric patients may be defined. This electronic medical record is in itself non-trivial, as notions of patient demographics, longitudinal data captured as patient visits, simple face sheet information such as current medications, current allergies, and past immunizations are represented there and defined in the database as different database objects. Following this example, a Meta view allows grouping in one database object—for reporting purposes—different elements, such as patient demographics, date of last admission, immunizations, staff, etc.

In other words, the back end repository for a well-designed longitudinal patient medical record is a gold mine for outcome reporting, via data mart or data warehouse projects. To this end, an LEMR may reduce or alleviate the need for data cleansing, as most of the effort of normalization may be made when creating the record itself, and most data elements may be codified elements—as opposed to text elements. It is worth noting that an LEMR may also carry many text-based elements, but it is a good practice to limit the number of such elements, for greater data harvesting quality at a later date.

4. Face Sheet Practical Implementation

IMO implemented a longitudinal patient medical record, named iEMR, for Dr. Kim Charles Meyers, supporting precepts advocated by Dr. Meyers, and supported by ADM and VisualADM. All aspects of electronic medical record system and method may be supported by ADM. In particular, most behaviors are dictated by the structure of the Meta data. In addition, ADM is also the storage for the application itself.

Figure 7:
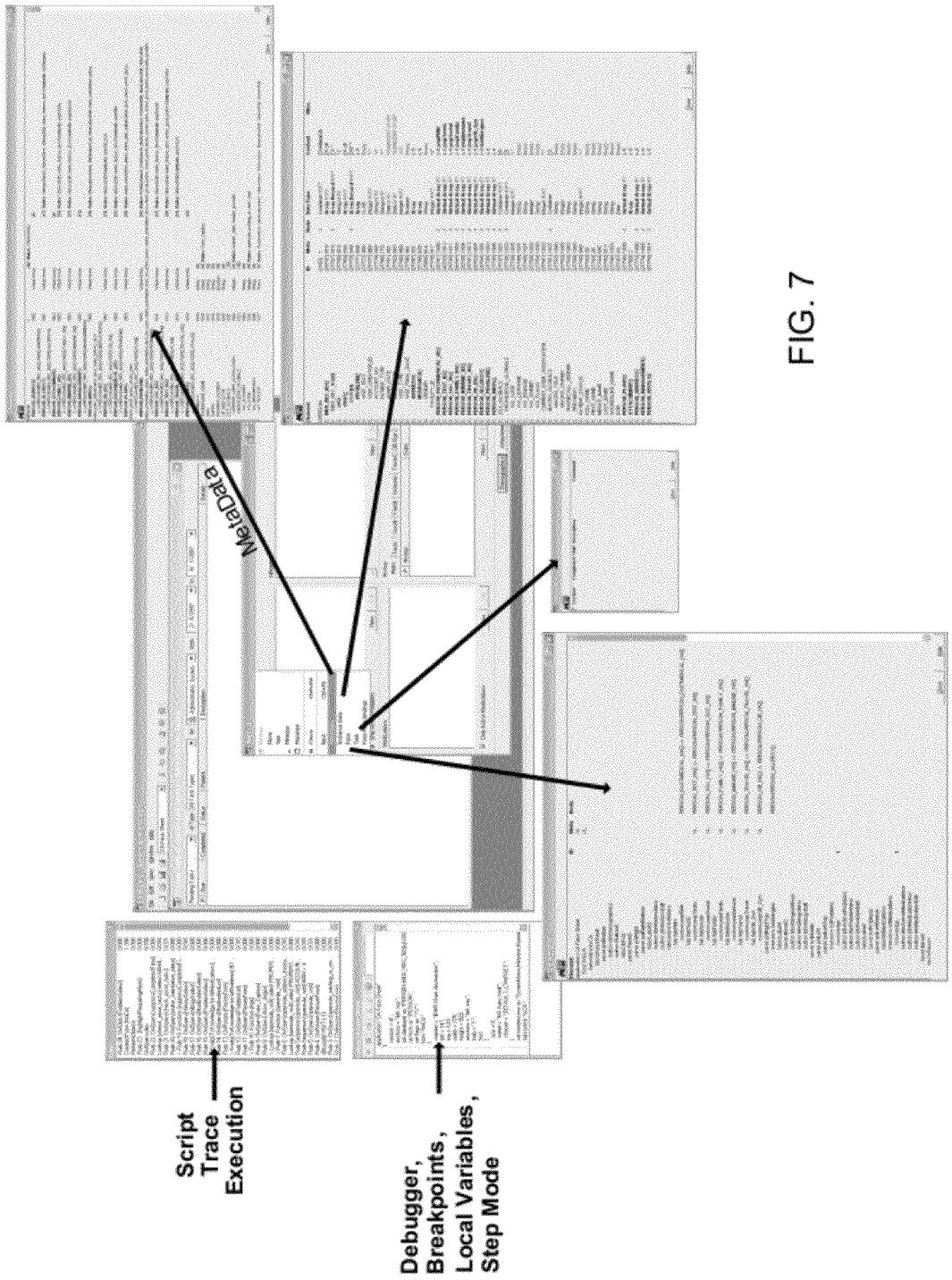
FIG. 7 is a representation of a visual output of a longitudinal patient medical record, overlaid with components of an advanced data manager.

FIG. 7 shows all facets of the iEMR implementation, from a VisualADM standpoint. According to the display of FIG. 7:

The face sheet is presented at the center of the figure.

Meta Data, Instance Data, Form internal hierarchy is detailed on right and bottom side.

The left hand side shows script execution, and script source code.

VisualADM's FormRunner, because of its integration with ADM, may provide the following features related to healthcare:

Mix of Rich Client and Thin Client Technologies.

A purely thin client interface may be slower, and more cumbersome, for real time patient interactions. VisualADM, as a rich client sharing thin client concepts, achieves speed of interactions.

Orientation Toward Healthcare.

The system and method may be capable of providing:

Support for role-driven workflow

Support for knowledge object orientation. Support for knowledge expansion.

Support for dictionary lists

A reduced amount of source code necessary for building electronic medical record-type applications.

Support for lexicon knowledge queries using IMO's LexiconHub.

Support for task-based workflow.

Rule scripting language geared toward health care.
Support for macro operations.
Support for document management functions
Support for PDF forms, PDF merge, PDF display.
Support for RTF reports.
Support for email workflow.
Support for HL7 communication services.

Example 1

A Document View Model of a Longitudinal Electronic Medical System in Action

This section presents an example of all parts of one embodiment of an LEMR working in concert. It will be appreciated that other alternative information may be captured, other process may be undertaken, and additional uses may all be possible. The premise is a new patient presenting with symptoms of asthma, receiving care through three successive care provider encounters.

Visit 1

Figure 8:
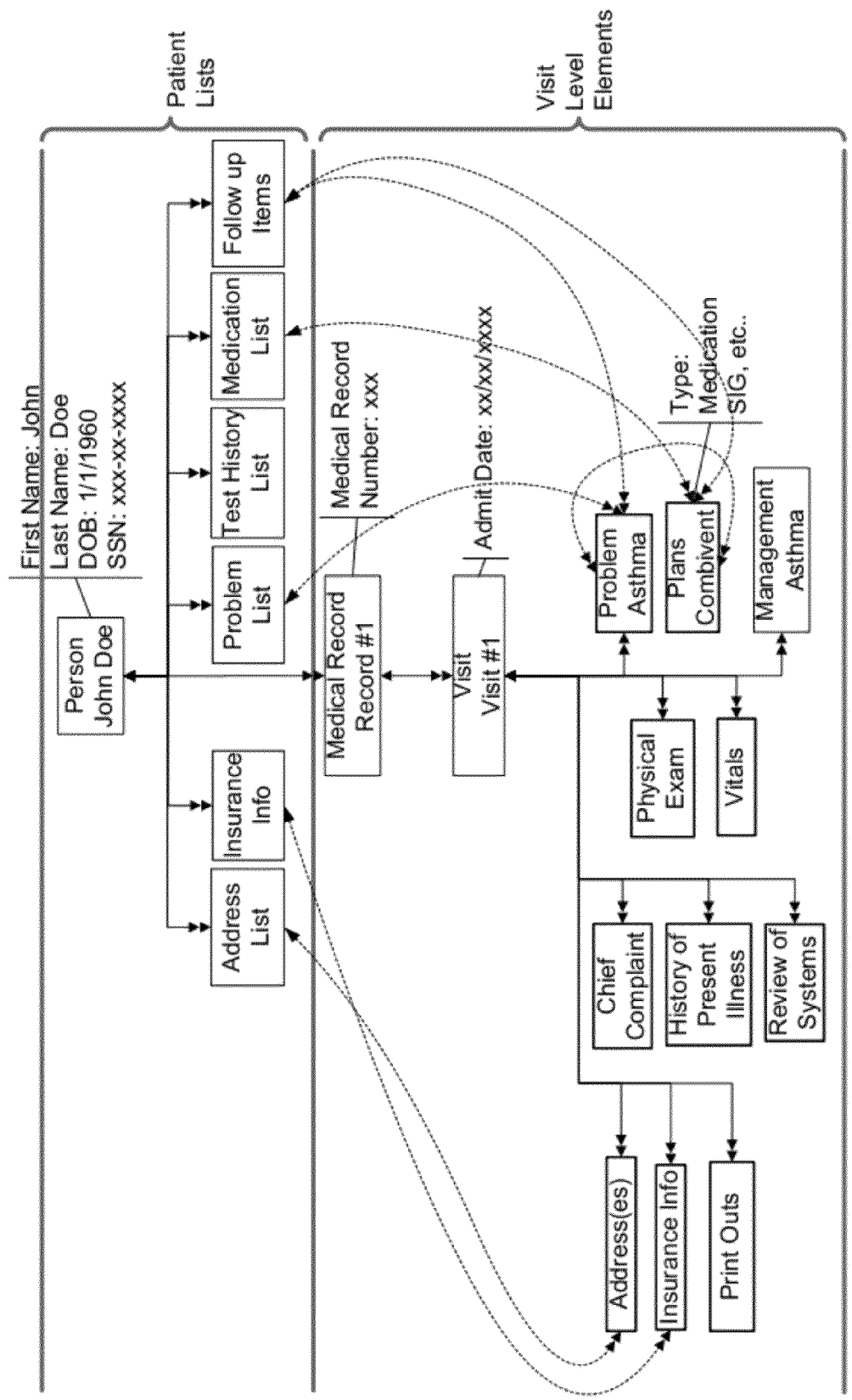
FIG. 8 is a schematic of an example of the inventive system and method in action through a first visit.

FIG. 8 describes Patient John Doe, with demographic information date of birth [Jan. 1, 1960], SSN [xxx-xx-xxxx] created as a new record. A new medical record is created by default. As for any new patient encounter, a new visit record is created as well.

The care provider—patient visit occurs. As part of the visit, the following information is captured:

Address and insurance information,
Chief Complaint, History of Present Illness and Review of Systems (subjective sections information content),
Physical exam and vitals (objective sections information content),
Problem is recorded as Asthma, with status "Under consideration"; Medication Plan includes "Combivent" (Assessment and Plan section information content).

In addition, at the highest level, current list relationships may be captured and recorded data may be linked to summarization icons or summarization references. As with other data objects generated during the visit, pointers may be used to link the recorded data to the summarization references. These relationships may include:

Current patient address list,
Current patient insurance list,
Current problem list: Asthma (version 1). Problem Asthma in this visit is also related to Medication Plan "Combivent" in this vist.
Current Medication List: Combivent (version 1).
Follow up items: Asthma (version 1), Combivent (version 1). These two items should be prominently displayed during the next visit to highlight patient follow-up.

After completion of the patient care provider encounter, the visit is closed to seal the interaction in time. In one embodiment, that part of the tree may never be touched or edited again so as to prevent entry of additional discrete data elements. However, actually entering data may also be considered a technical, not logical, question, so the system or method may allow a user to go back and edit text, eg.

As shown in FIG. 8, the connections generally have a single arrowhead at one end and a double arrowhead at the other. This represents a one-to-many combination. The solid lines indicate that this data may be represented in a tree structure. Moreover, the summarization icons of "Address List," "Insurance Info," "Problem List," "Test History List," "Medication List," and "Follow up Items" may be linked to information captured during each visit, so that the information may have multiple parents. In this case, the LEMR takes on a graph structure and increases in complexity.

A next encounter time may be established for the patient's next encounter, supported by a care provider-based task. Optionally, additional tasks may be created plan by plan, for laboratory tests for example.

Visit 2

Figure 9:
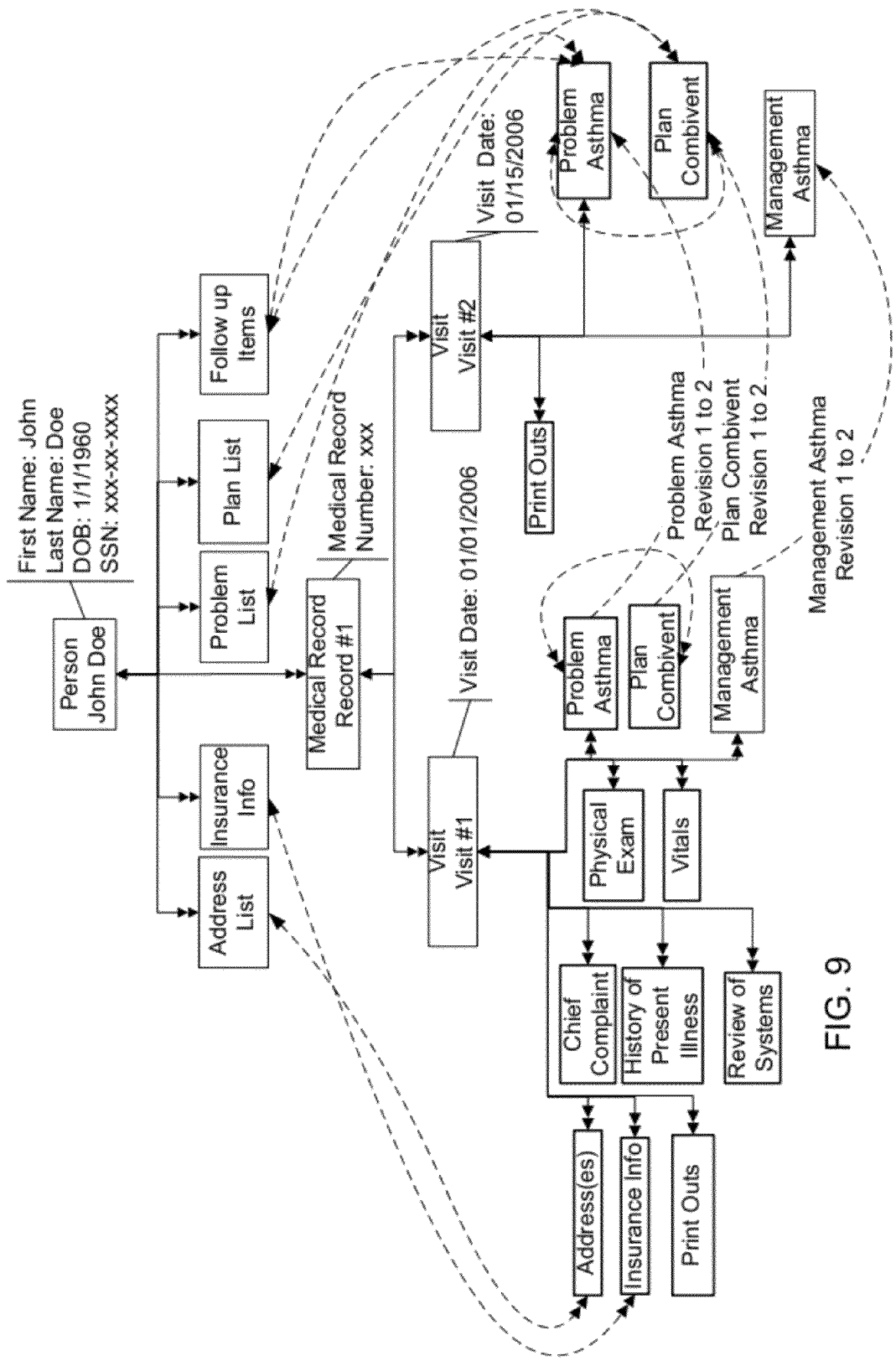
FIG. 9 is a schematic of an example of the inventive system and method in action through a second visit.

FIG. 9 shows patient, John Doe, after his second visit. As a new patient encounter, a new visit record is created, having a new temporal identifier to signify when the visit occurred, as well as a new instance identifier, detailing that the visit is a new visit in the patient's history. The care provider addresses the follow up item list, including the plan or plans created in the previous visit, and creates data entry for the following:

Problem Asthma.

Information for this problem is modified, thus creating a new revision. A problem status change was performed: status was changed from "Under Consideration" to "Doing Better." The process of creating a problem revision and providing continuity for a problem is a three-part process:

1) Problem Asthma revision 2 is created. The problem may have a new temporal identifier to describe when the creation occurred. However, it may have the same instance identifier as Visit 2.
2) Problem Asthma revision 2 is back linked to Problem Asthma revision 1.
3) The problem list link to Problem Asthma revision 1 is updated to be pointing to Problem Asthma revision 2.

Medication Combivent.

Information for this medication is modified, thus creating a new revision. A medication status change is performed: status is changed from no status to "Continue". Similarly to the problem Asthma, the process of creating a medication revision and providing continuity for the medication is a three-part process:

Medication Combivent revision 2 is created.

1) Medication Combivent revision 2 is back linked to Medication Combivent revision 1.
2) The Medication list link to Medication Combivent revision 1 is updated to be pointing to Medication Combivent revision 2.
3) In addition, Problem Asthma version 2 is related to Medication Combivent version 2.

Follow up items for visit #1 are cleared, and new follow up items for visit #2 are created. In this example, such items should be prominently displayed during the next visit to highlight patient follow-up. Again, the visit is closed to seal the interaction in time after completion of encounter.

Again, a next encounter time may be established for the patient's next encounter, supported by a care provider-based task, and additional tasks may be created plan by plan.

Visit 3

Figure 10:
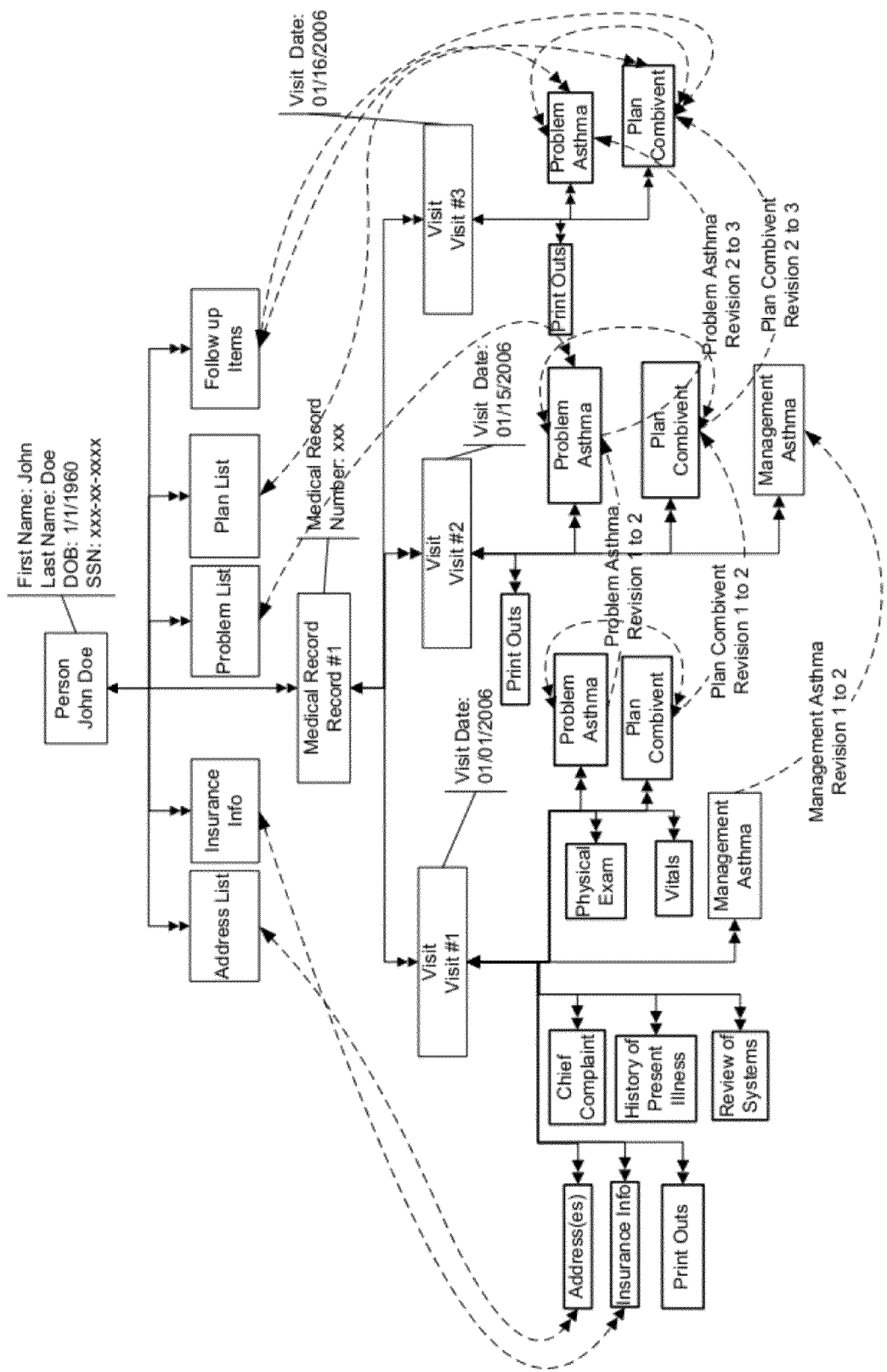
FIG. 10 is a schematic of an example of the inventive system and method in action through a third visit.

FIG. 10 represents a third visit. As a new patient encounter, a new visit record is created, again having new temporal and instance identifiers. The care provider only addresses changes for the medication Combivent, for a refill for example, using the follow up link. The following actions occur:

Medication Combivent.

Information for this medication is modified, again creating a new revision. A medication status change is performed: status is changed from "Continued" to "Refill". Similarly to visit 2, revision actions occur by creating revision 3, linking revision 3 to revision 2, and re-linking medication list link from revision 2 to revision 3.

Problem Asthma.

Element Information for Problem Asthma is not modified, but linking information to Medication Combivent is changed thus motivating a new revision. Similar steps apply as described during visit 2 for Problem Asthma.

In addition, Problem Asthma version 2 is related to Medication Combivent version 2.

Follow up items for visit #2 are updated to point toward items for visit #3.

Example 2

Implementation of a Complex Problem

Figure 11:
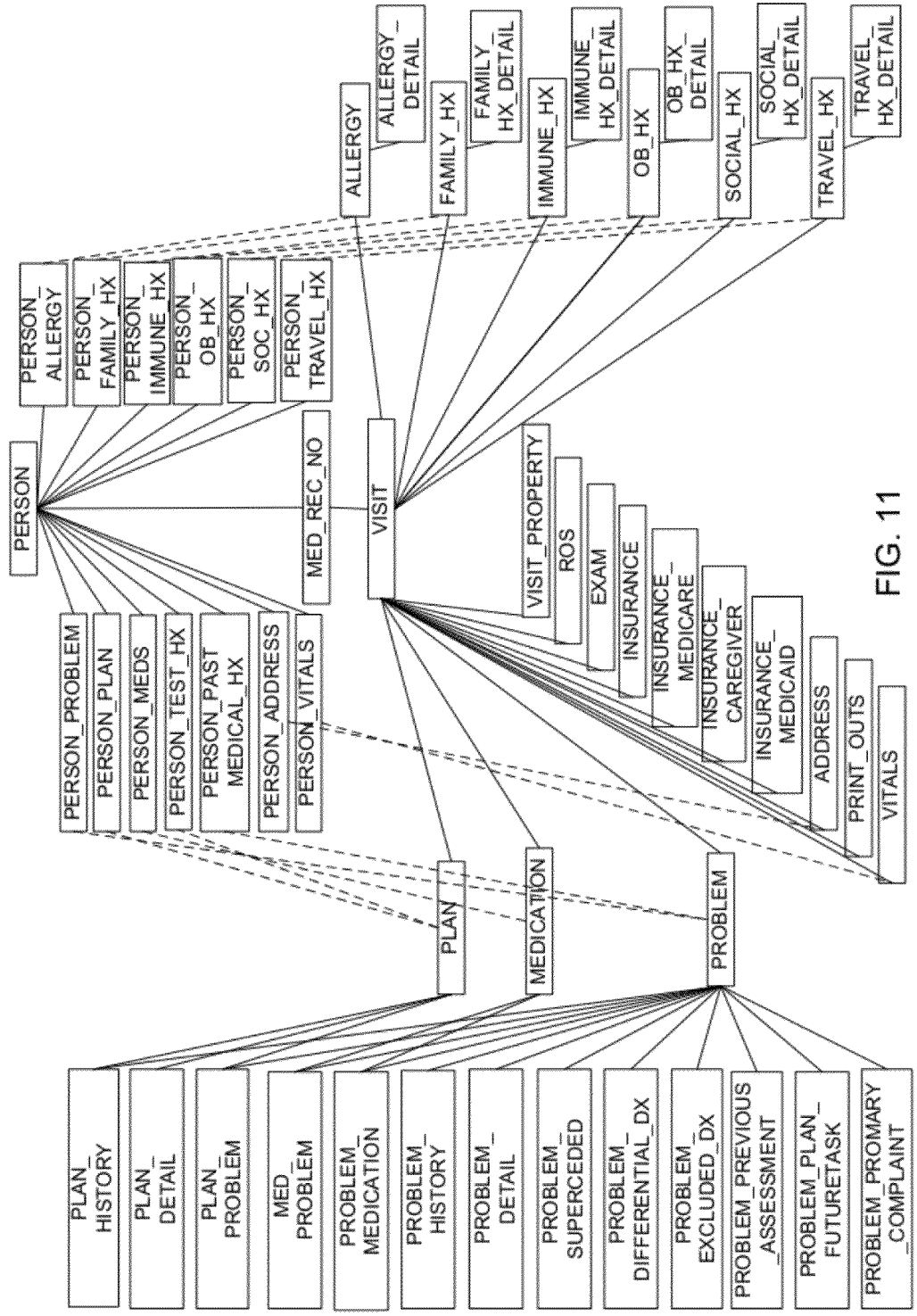
FIG. 11 is a functional entity relationship diagram of the longitudinal electronic medical record of FIG. 1.

FIG. 11 shows in detail the example of LEMR as provided in FIG. 1, this time expressed as an Entity Relationship Diagram. Note that FIG. 11 does not show any discrete elements.

In this example, most ADM administrative interactions may be handled using XML, mainly for safe keeping, transfer, and migration operations; Meta data is a prime example, and the code at the end of the specification shows a portion of the example depicted in FIG. 11 as an XML document.

Example of Longitudinal Medical Record Architecture

An XML document may be used as a source for ADM behaviors, primarily for translation to RDBMS structures; the example described above may create and maintain without external help 110 tables, 58 triggers, 249 indexes and 757 primary, foreign, unique and check constraints.

Figure 12:
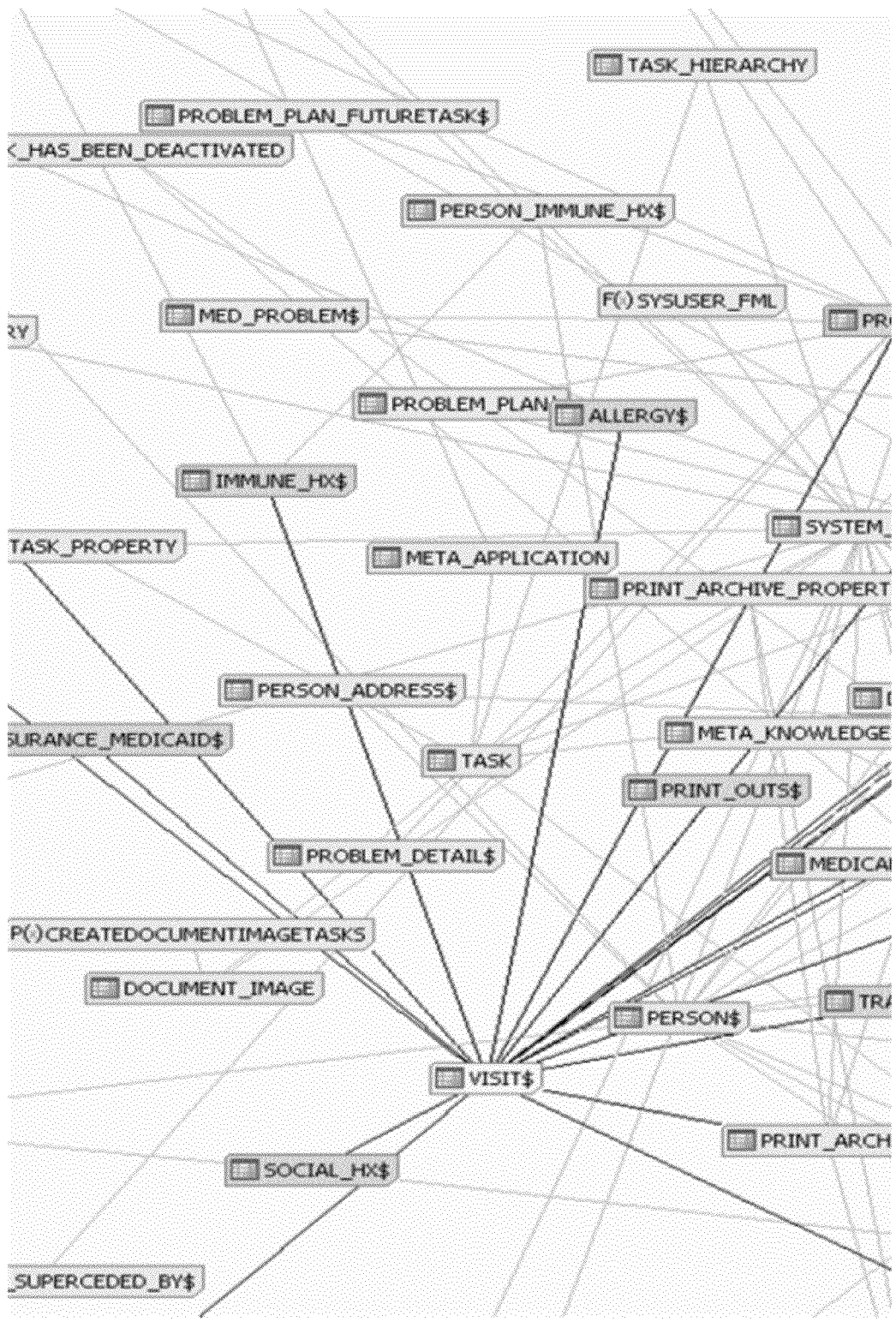
FIG. 12 is the left side of a relational database representation of the longitudinal electronic medical record of FIG. 1, from a database administrator standpoint.
Figure 12A:
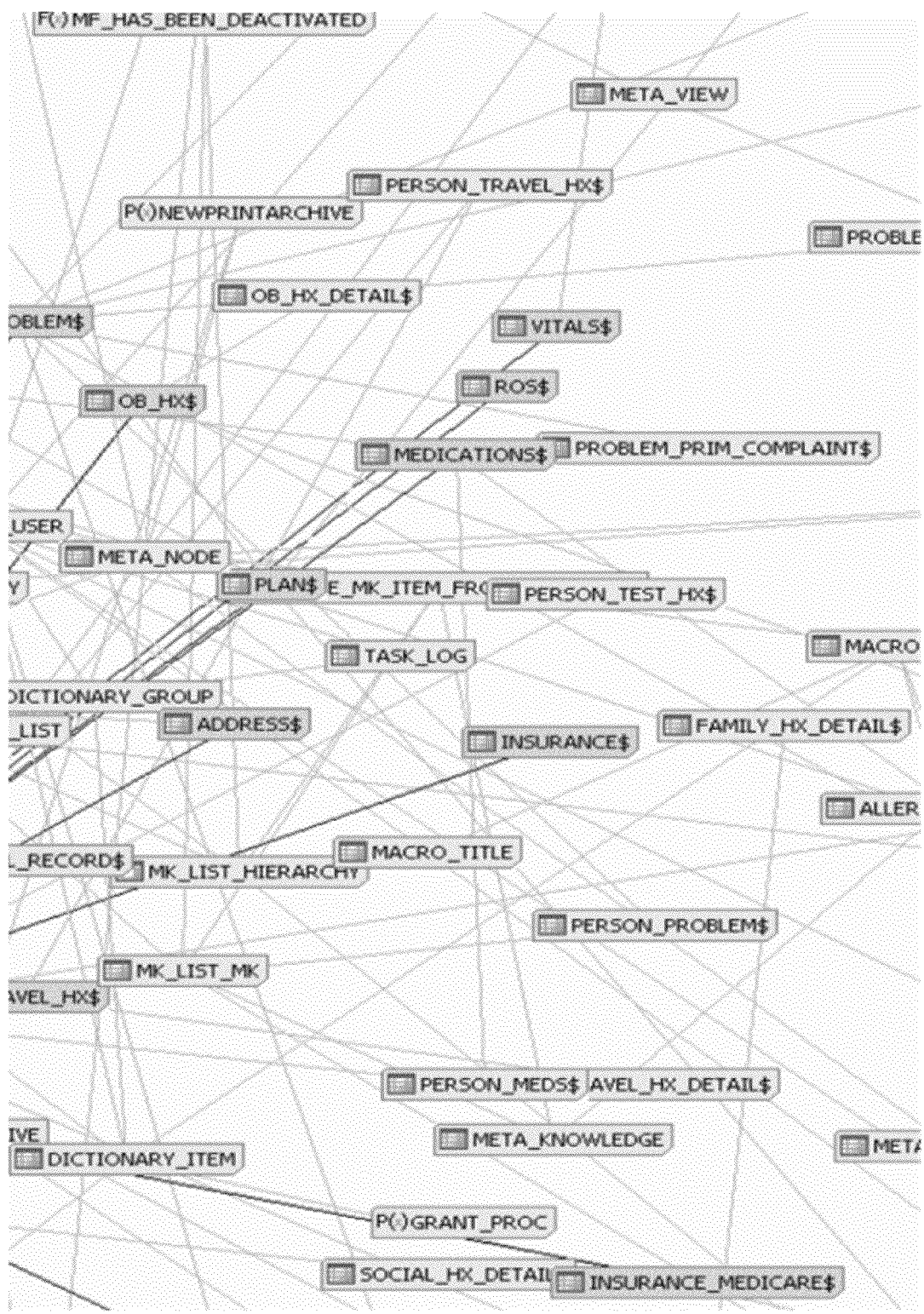
FIG. 12A is the right side of a relational database representation of the longitudinal electronic medical record of FIG. 1, from a database administrator standpoint.

FIG. 12 shows the code at the end of the specification expressed as a relational database, from a database administrator standpoint. This visualization may be rather intimidating, and may only present a portion of the database schema. It may not be advisable to maintain an ADM-generated database using traditional database management tools, but rather to use ADM-supplied management tools.

Figure 13:
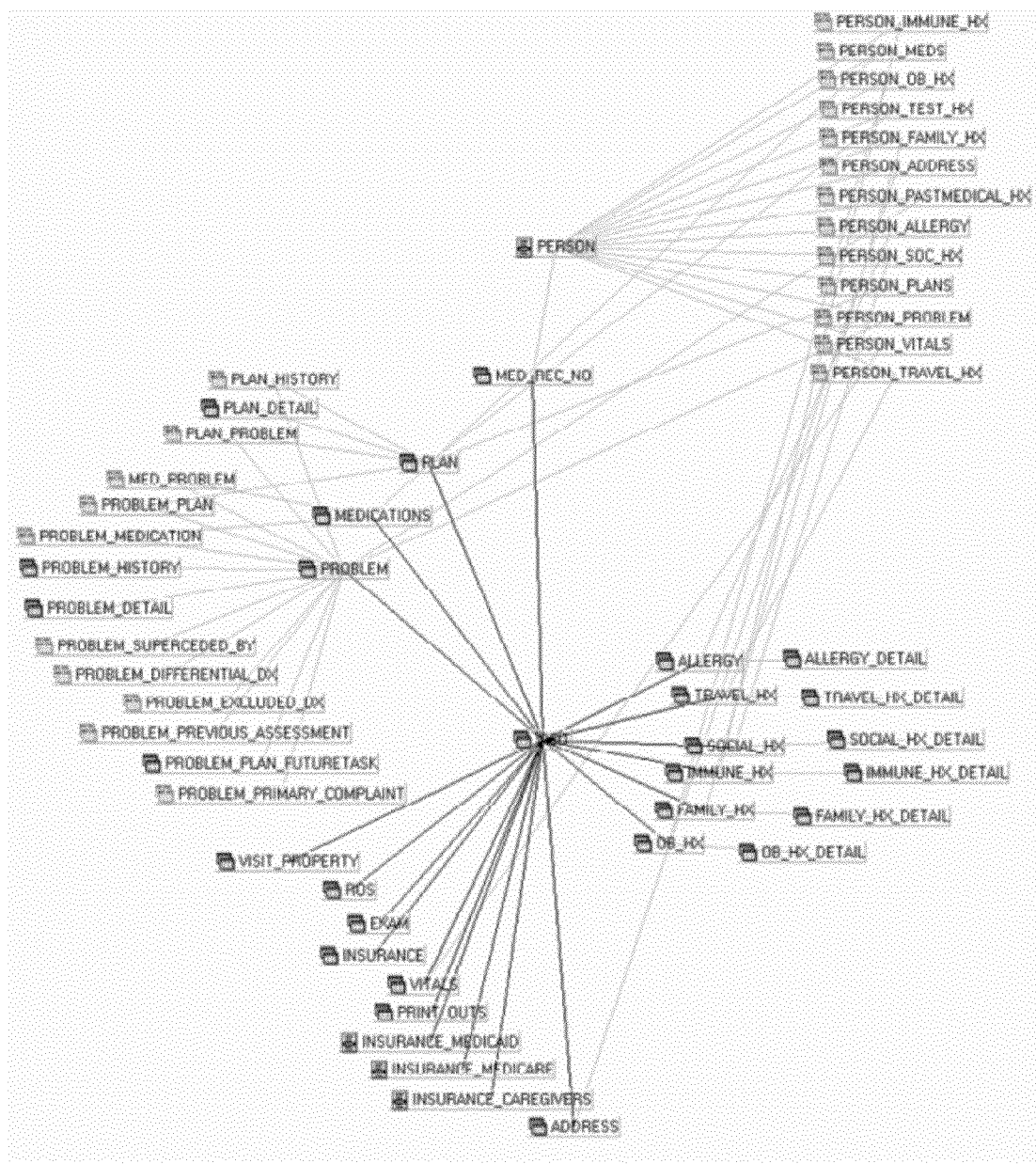
FIG. 13 is a schematic of the metadata behind the entities of FIG. 11, arranged using an advanced data manager.

FIG. 13 shows the Meta data exposed in the above-mentioned code, as managed by ADM database management tools.

Meta Data to Relational Database Deployment

The Meta data layer may be translated into tables, indexes, primary key and foreign key constraints, and/or triggers, for storage of instance data. Deployment may follow these simple rules:

A Meta data element either triggers creation of a table or addition to the payload of a table.

Meta data datatypes may be divided into 3 types:

1. Container and Array.

These data types trigger a table creation. The name of the table may be the meta data short name with '$' as a suffix. The resulting table may have:

A primary key (the table name with a '_code' suffix),

Possibly a foreign key parent relationship to the parent meta data deployed table if the meta data has a parent meta data element, A default row text (the table name with a '_text' suffix), A set of column defined as 'payload', defined from child meta data discrete elements, Tagging references, such as the row creation date (TAG_CREATEDATE), the row last update date (TAG_SYSTEMDATE), and the row user author reference (TAG_SYSTEMUSER).

Furthermore, an array meta data element may add an order index reference as a tag reference (TAG_ORDER).

2. Discrete data types, including string, number, boolean, real, text and date. Meta data elements of discrete data type participate in the parent meta data element table payload. String, number, real, boolean, date and text may respectively translate into varchar2(4000), number(10), number(10,5), number(1), date and CLOB (character large object) Oracle data types. The string data type may slightly differ: the user has the ability to set the data type length, from 1 to 4000. It is by default 4000.

3. Virtual Array.

A virtual array may indicates arrays of relationships from one table to another table, as translated into relational database design terms. In other words, the result may be a straightforward relational table: a reference column to the parent meta data table (FROM_CODE), a reference column to the child meta data table (TO_CODE), and tagging references such as the row last update date (TAG_SYSTEMDATE), and the row user author reference (TAG_SYSTEMUSER).

Figure 14:
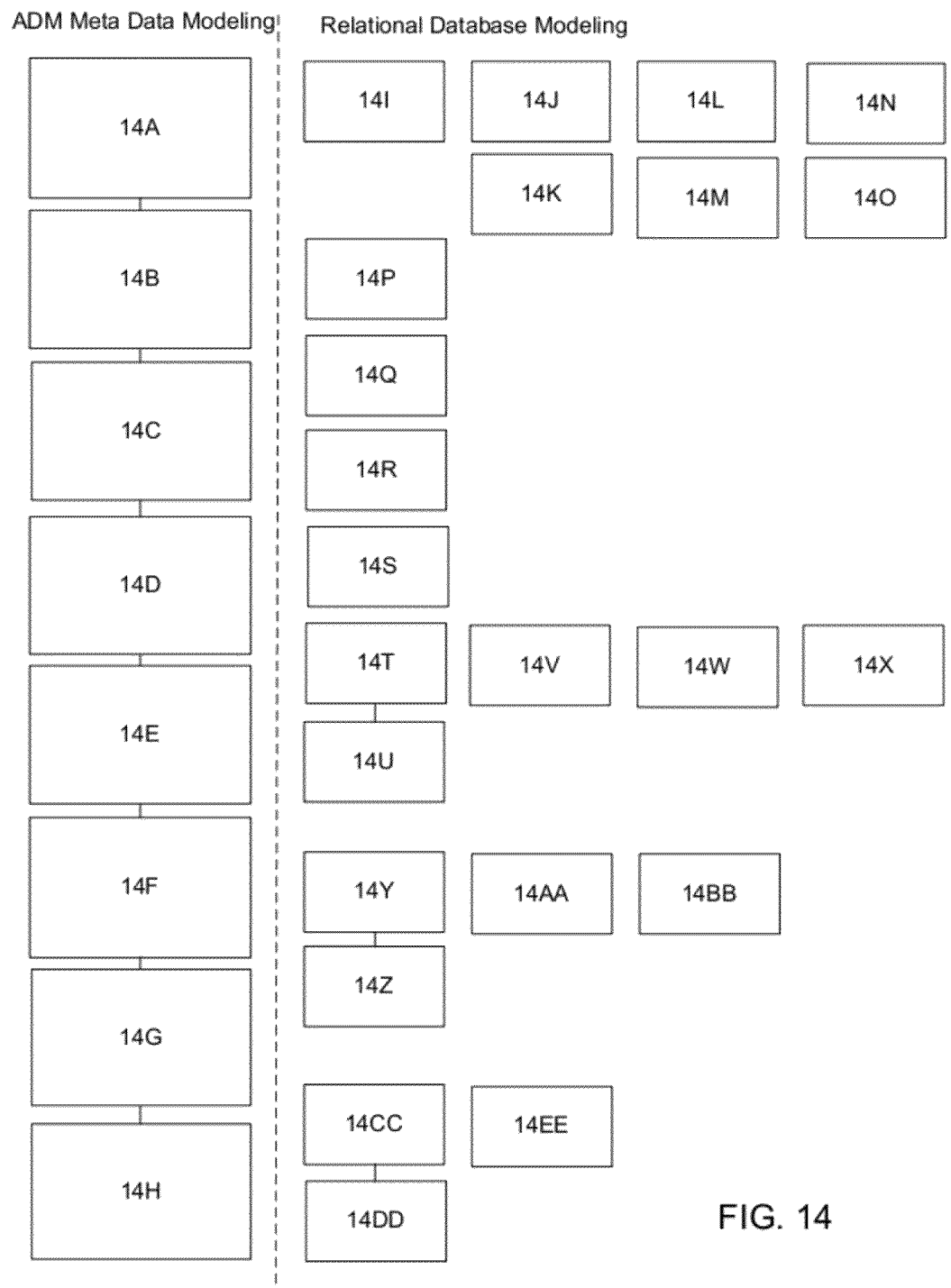
FIG. 14 is an example of the deployment of the metadata of FIG. 13.
Figure 14B:
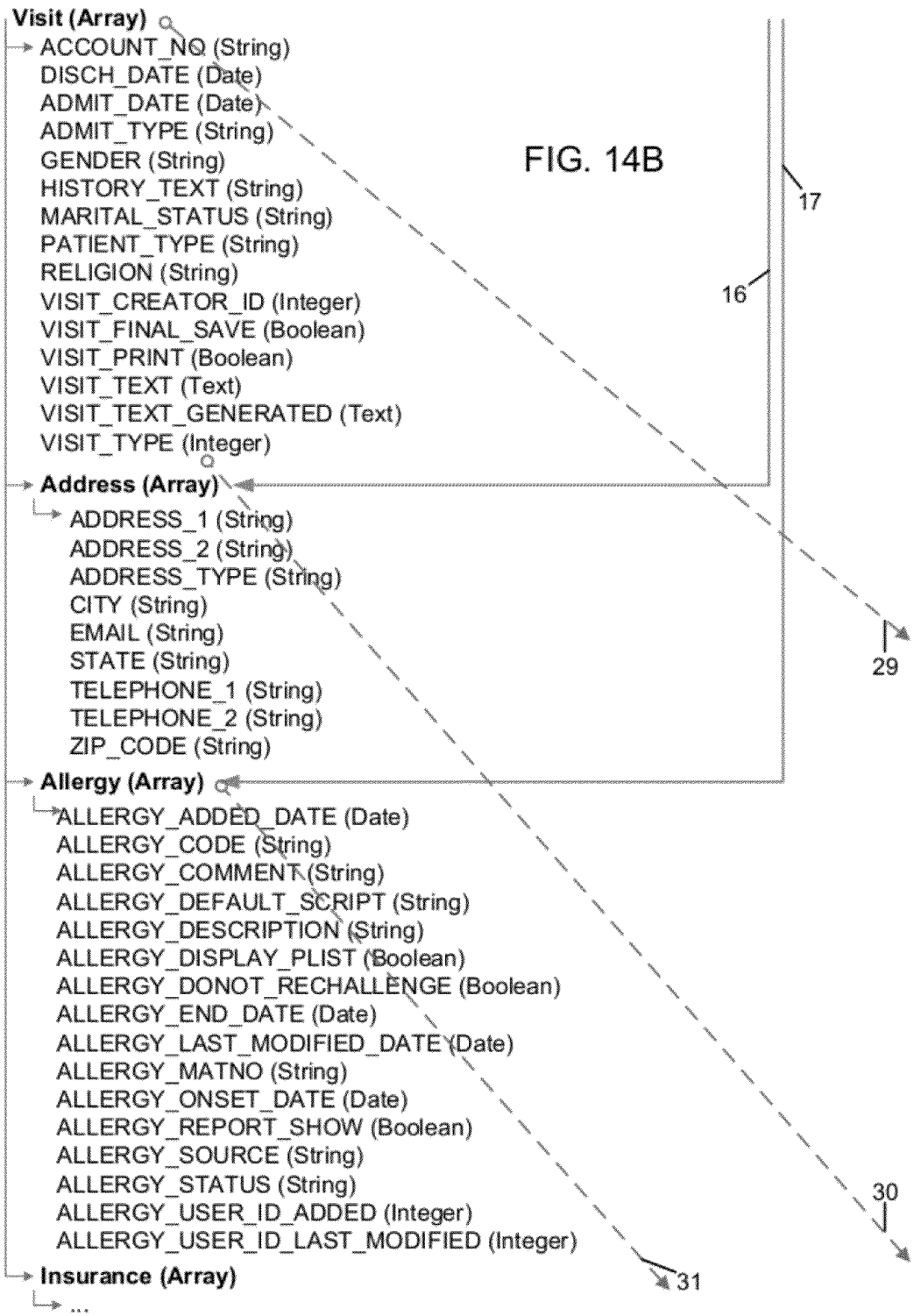
FIGS. 14A-14EE are the deployment of FIG. 14 shown in an enlarged form.
Figure 14C:
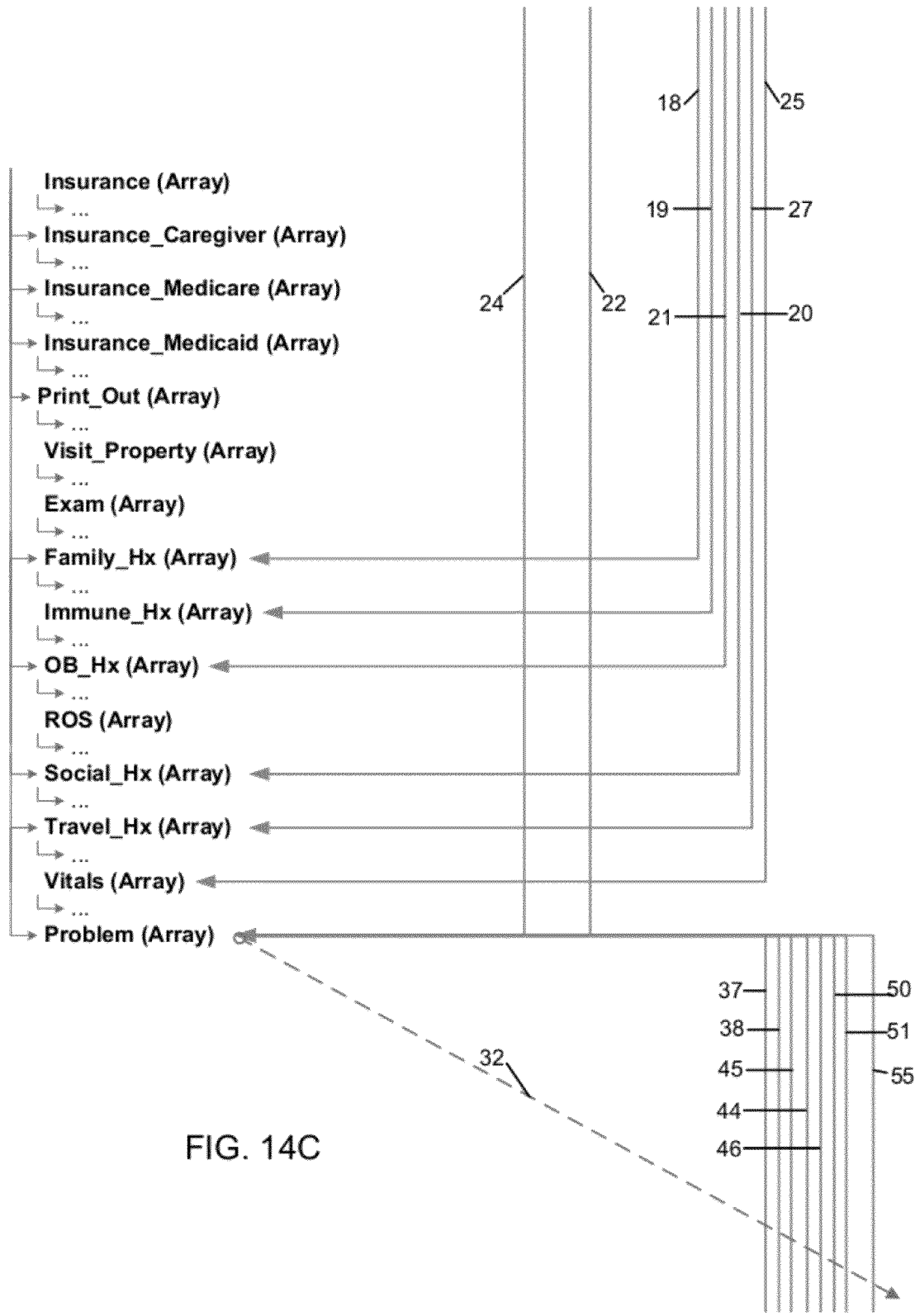
Figure 14D:
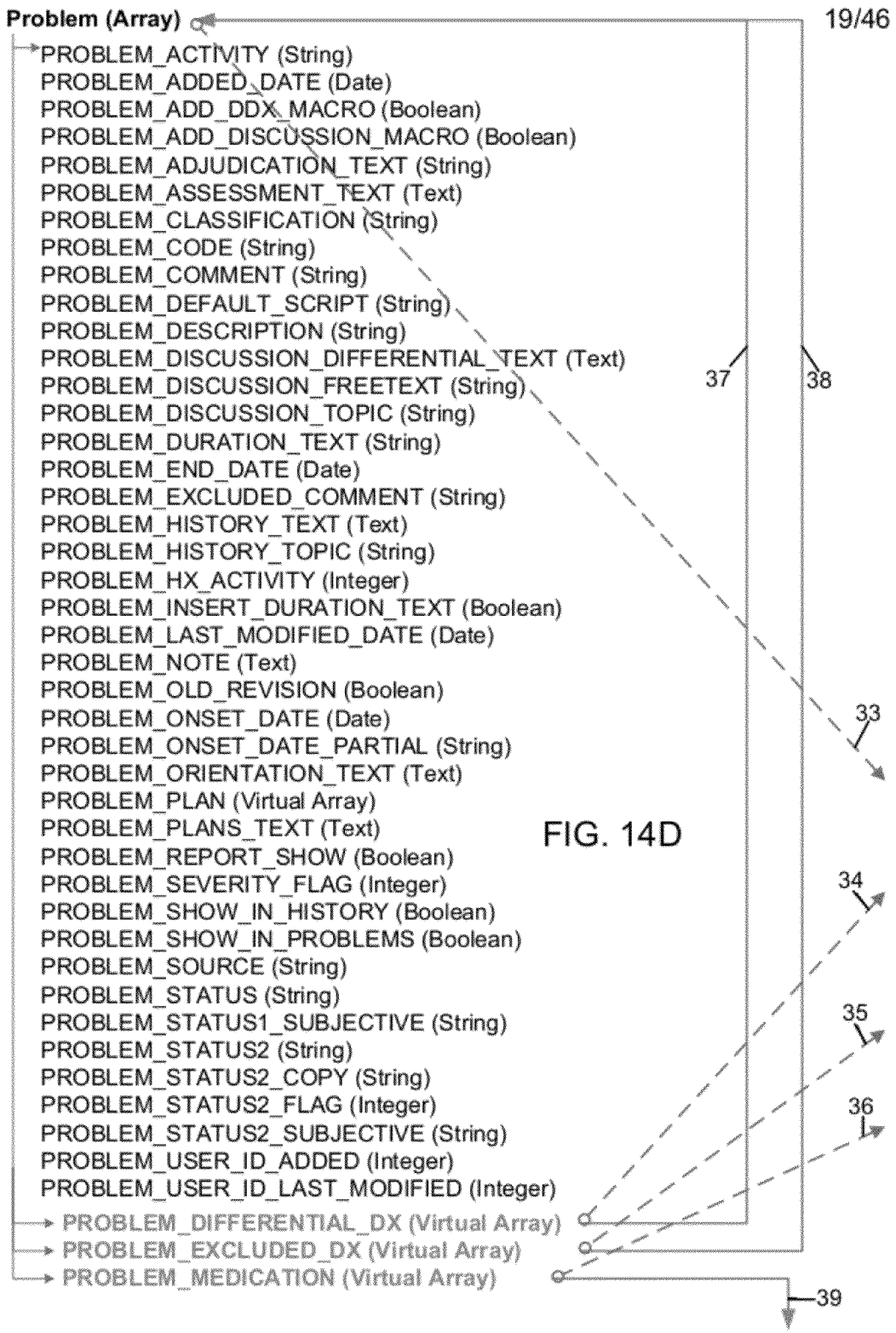

FIG. 14 illustrates these rules, using FIG. 10 Meta data as a base example. FIG. 14 shows a condensed view of FIGS. 14A-14EE, illustrating the relationship among elements on each side and between elements on each side. Matching reference numerals in the various sheets of FIGS. 14A-14EE designate identical arrows as they extend from sheet to sheet. FIGS. 14A-EE show:

The Meta data graph, modeled on the left hand side. The arrows to the left of the data elements in the Meta data model indicate parent child relationships, thereby building a tree. The solid arrows extending to the right of the grayscale data elements like "Patient_Address (Virtual Array)" and "Patient_Allergy (Virtual Array)," indicate virtual array relationships, relationships that constitute the Meta data graph attribute. In FIG. 14A, these are arrows numbered 16-28, for example.

The relational database created from the Meta data on the right hand side. Each shaded box is a table. Solid arrows, like those numbered 74, 79-84, 86, 88 and 90 in FIG. 14T, indicate a child-parent relationship (i.e., a foreign key to primary key relationship), and curved, dashed arrows, like those numbered 77-78, 85, 87, 89 and 91-93 in FIG. 14T, indicate a double foreign key relationship in the case of virtual array tables instantiated as true relational tables.

Straight-line, dashed arrows, from the left hand side to the right hand side, represent a Meta data element instantiated as a table.

Figure 14E:
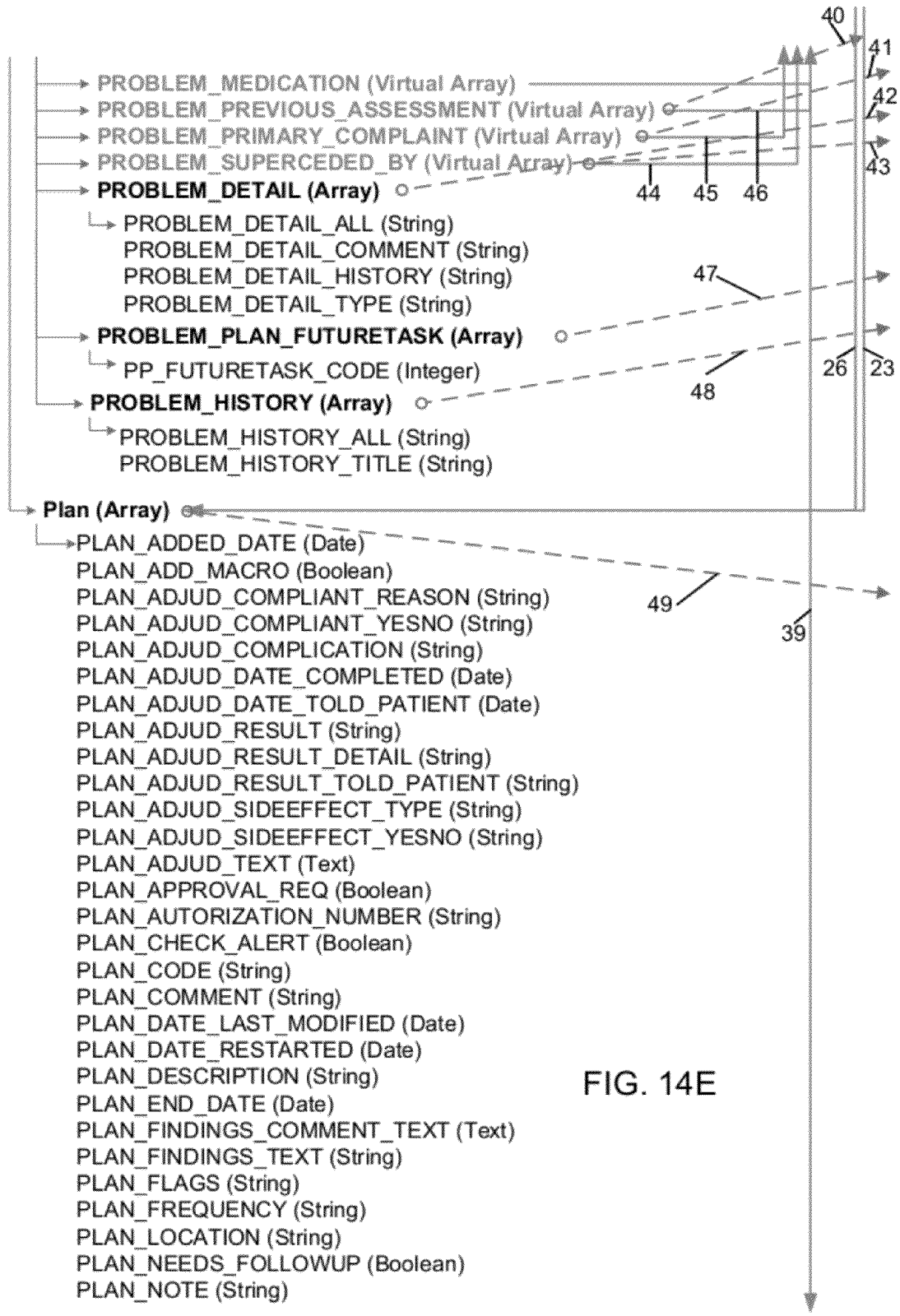
Figure 14F:
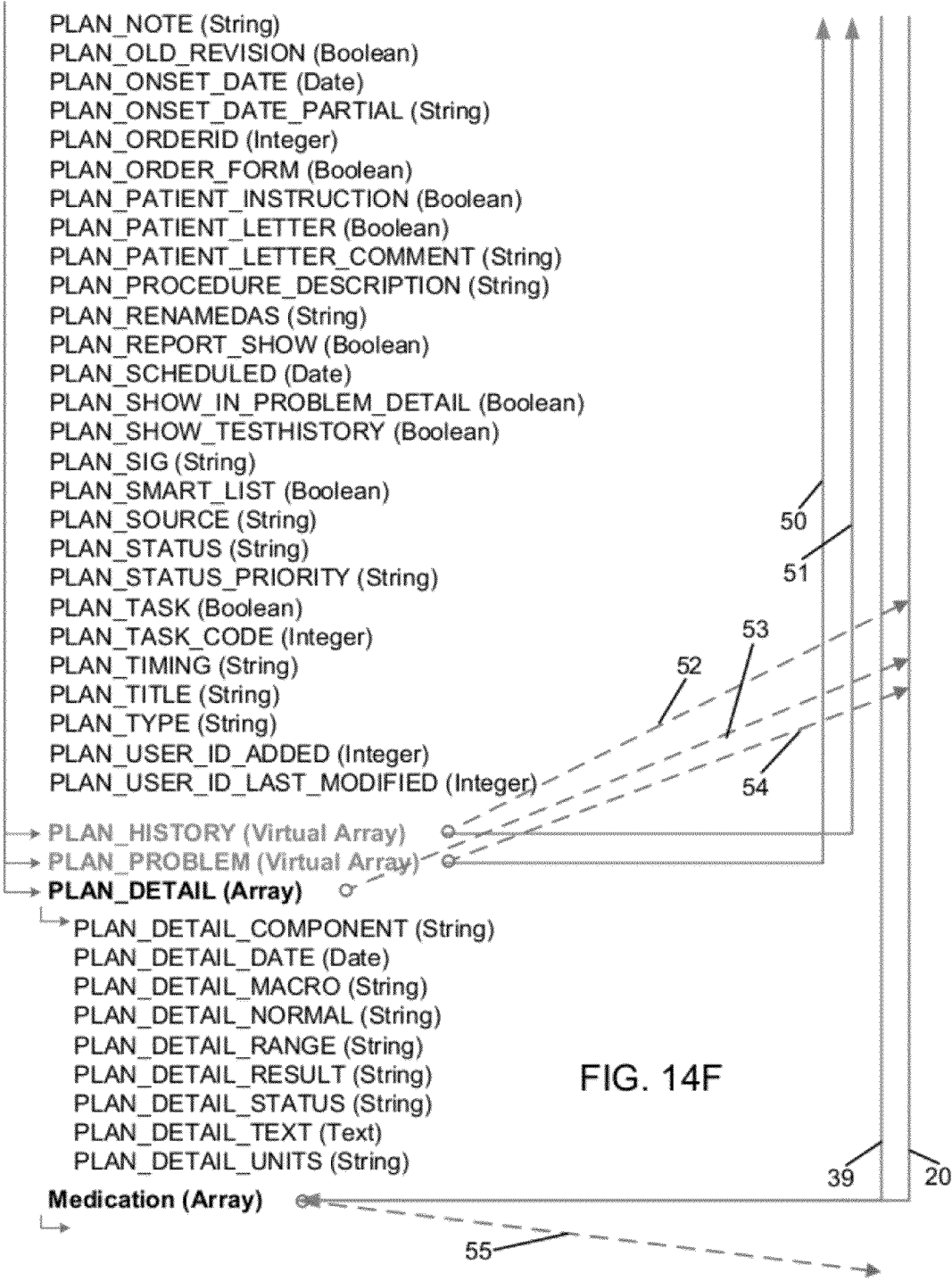
Figure 14G:
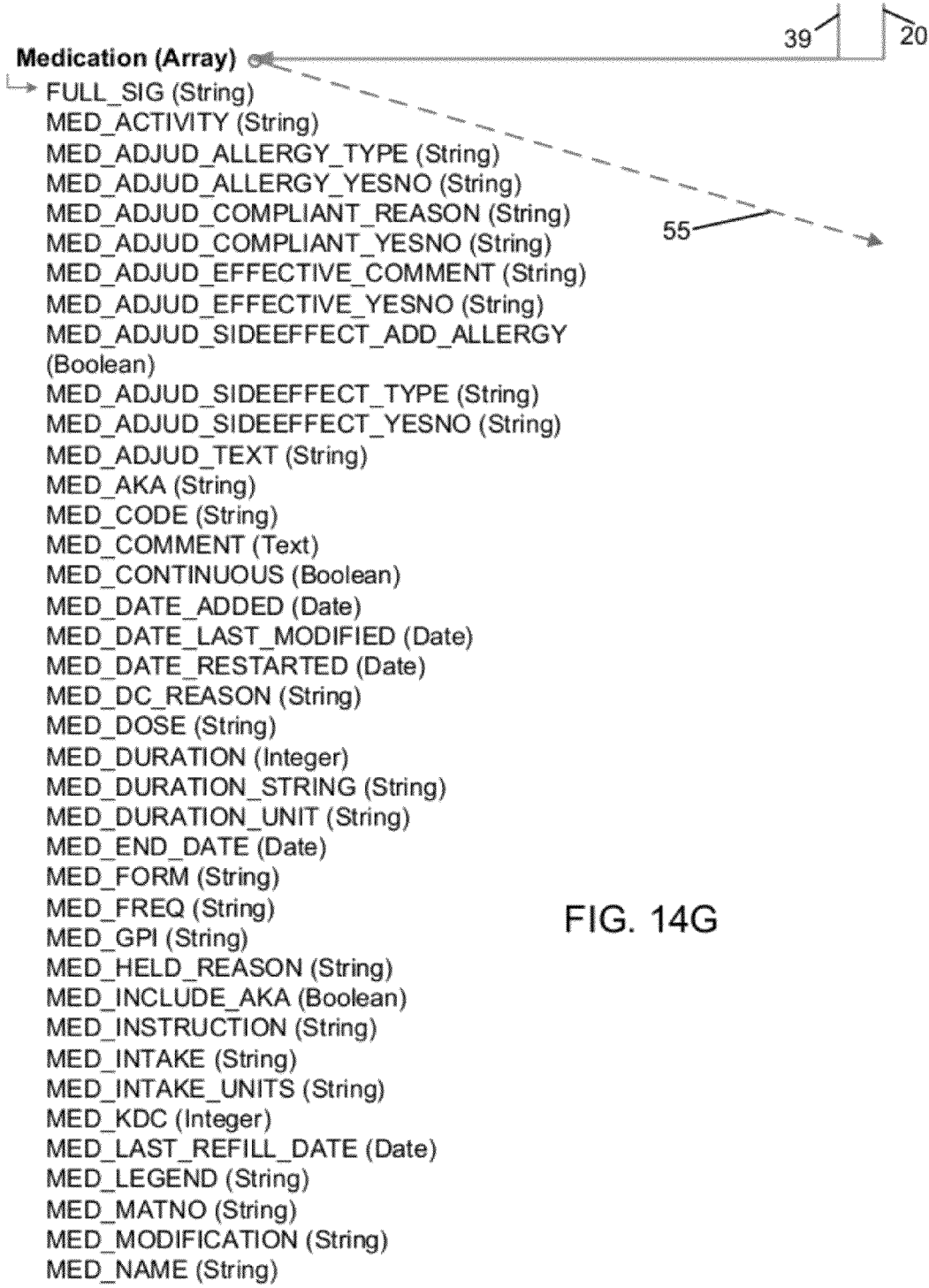
Figure 14H:
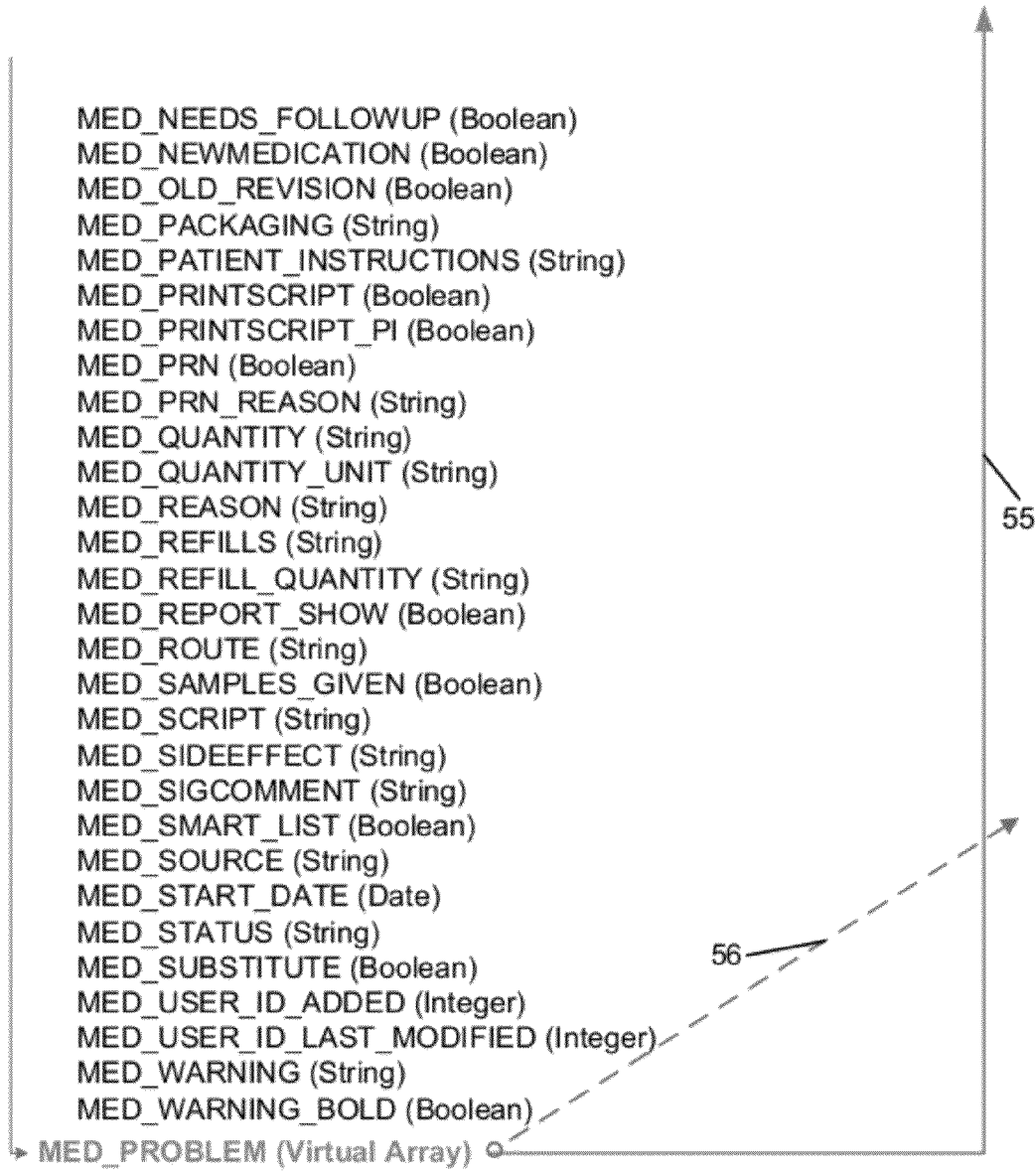
Figure 14I:
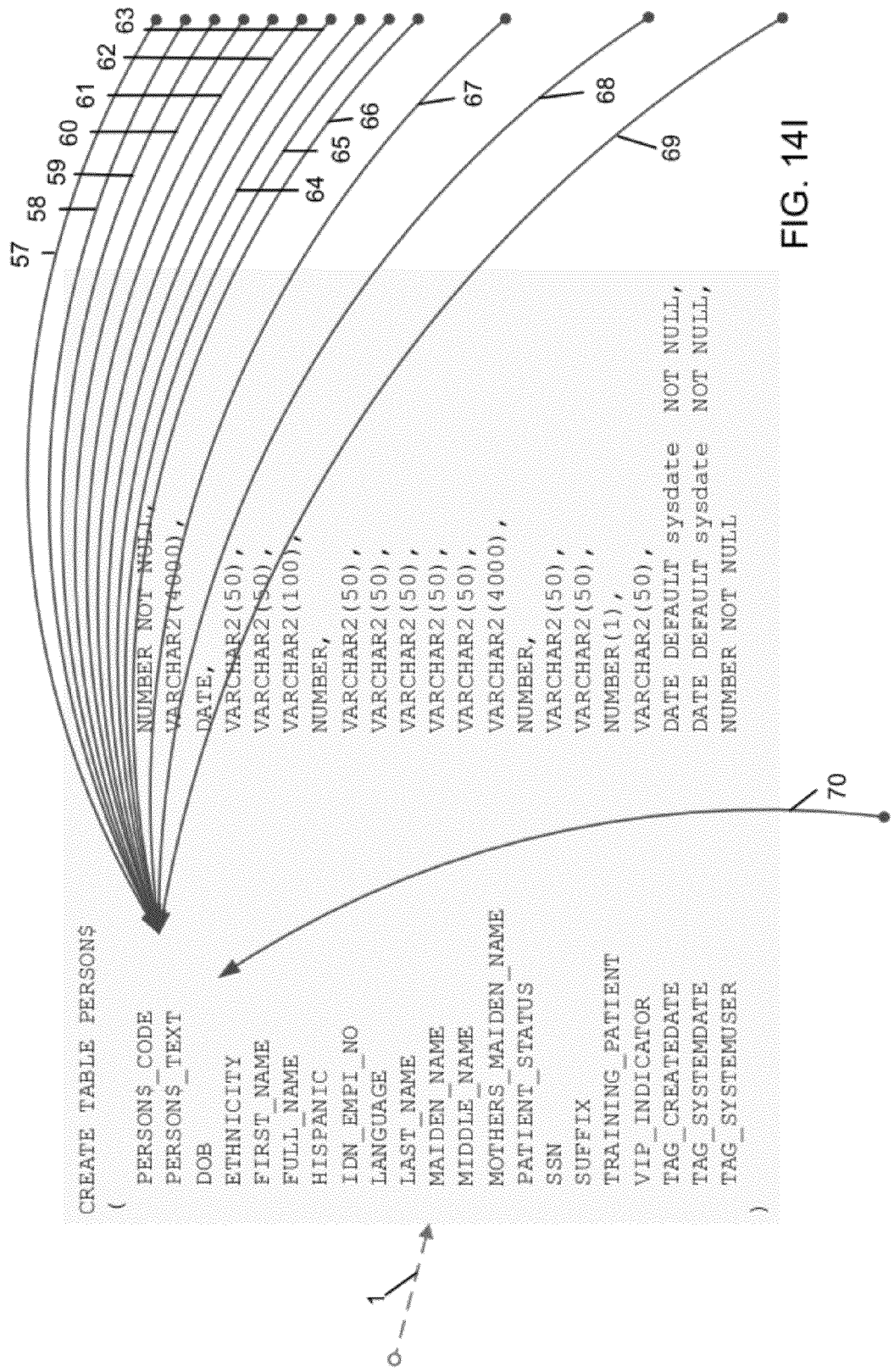
Figure 14J:
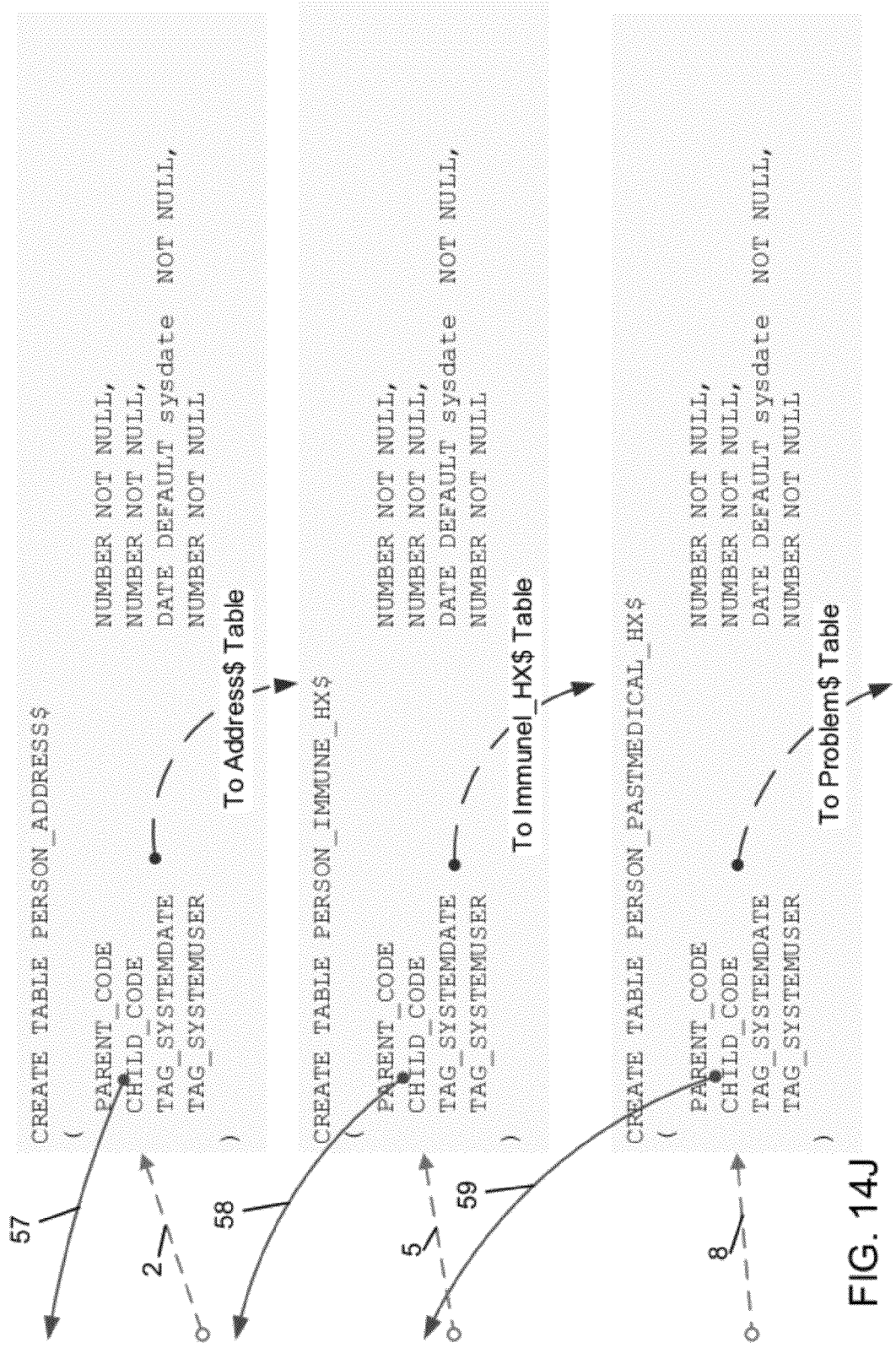
Figure 14K:
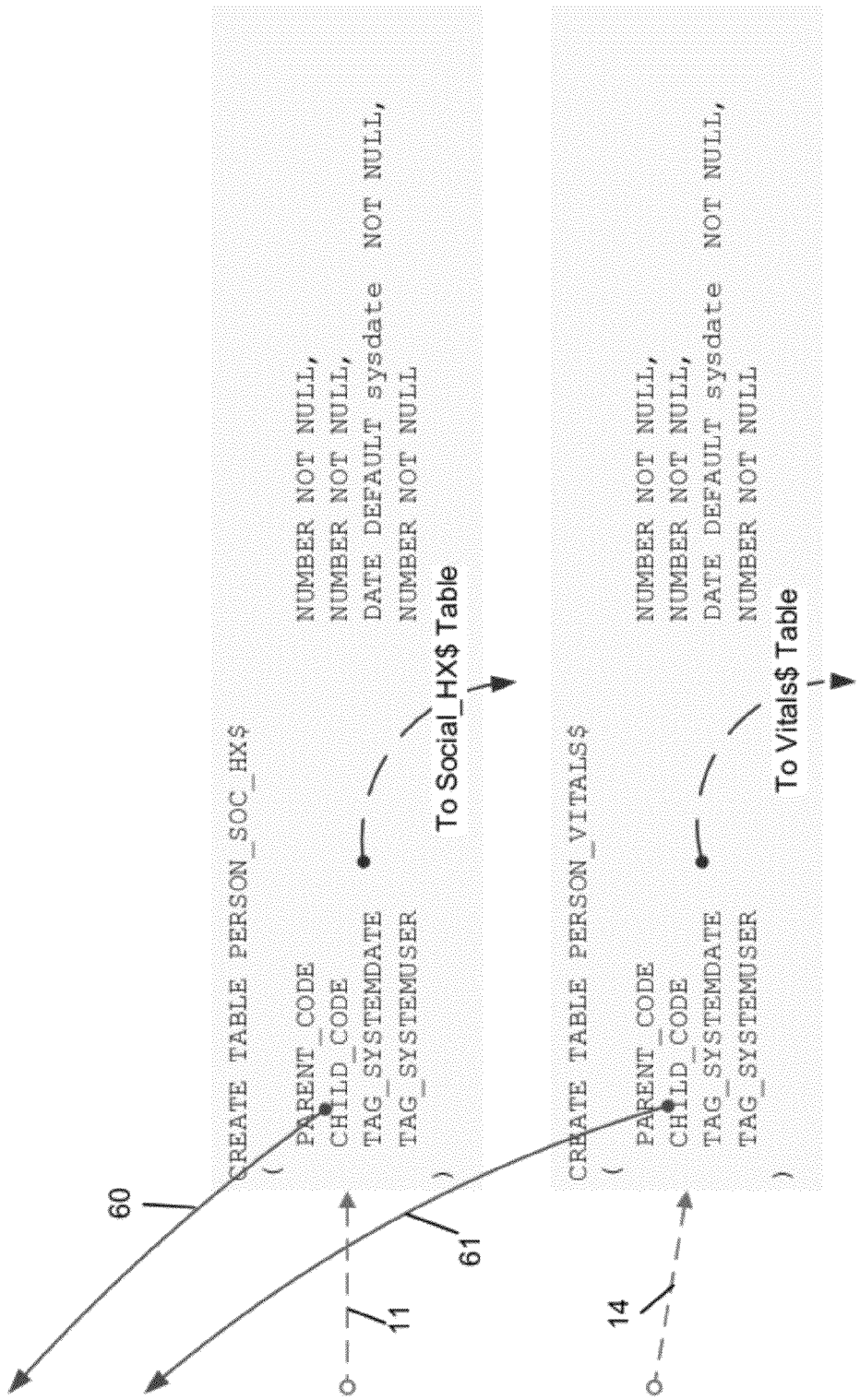
Figure 14L:
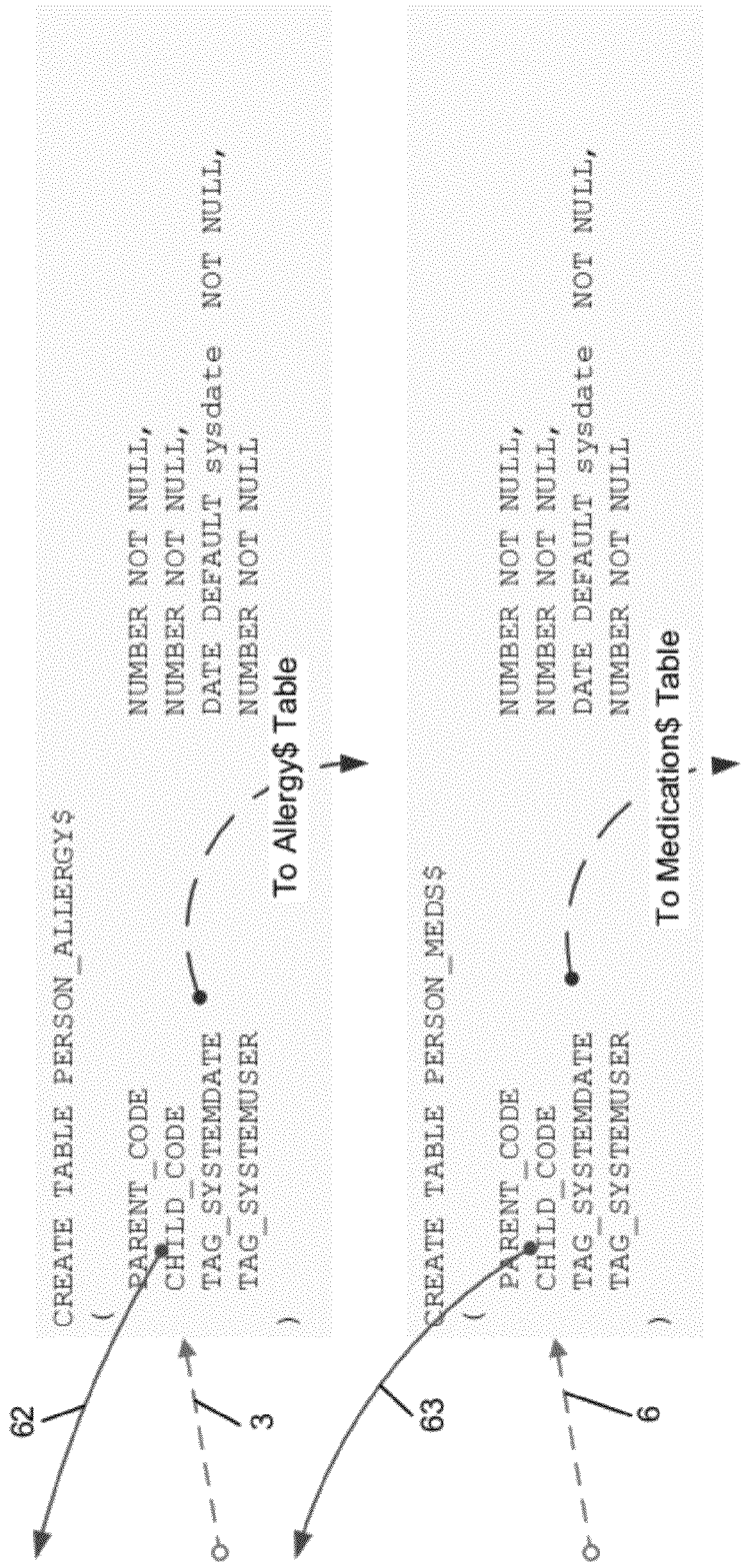
Figure 14M:
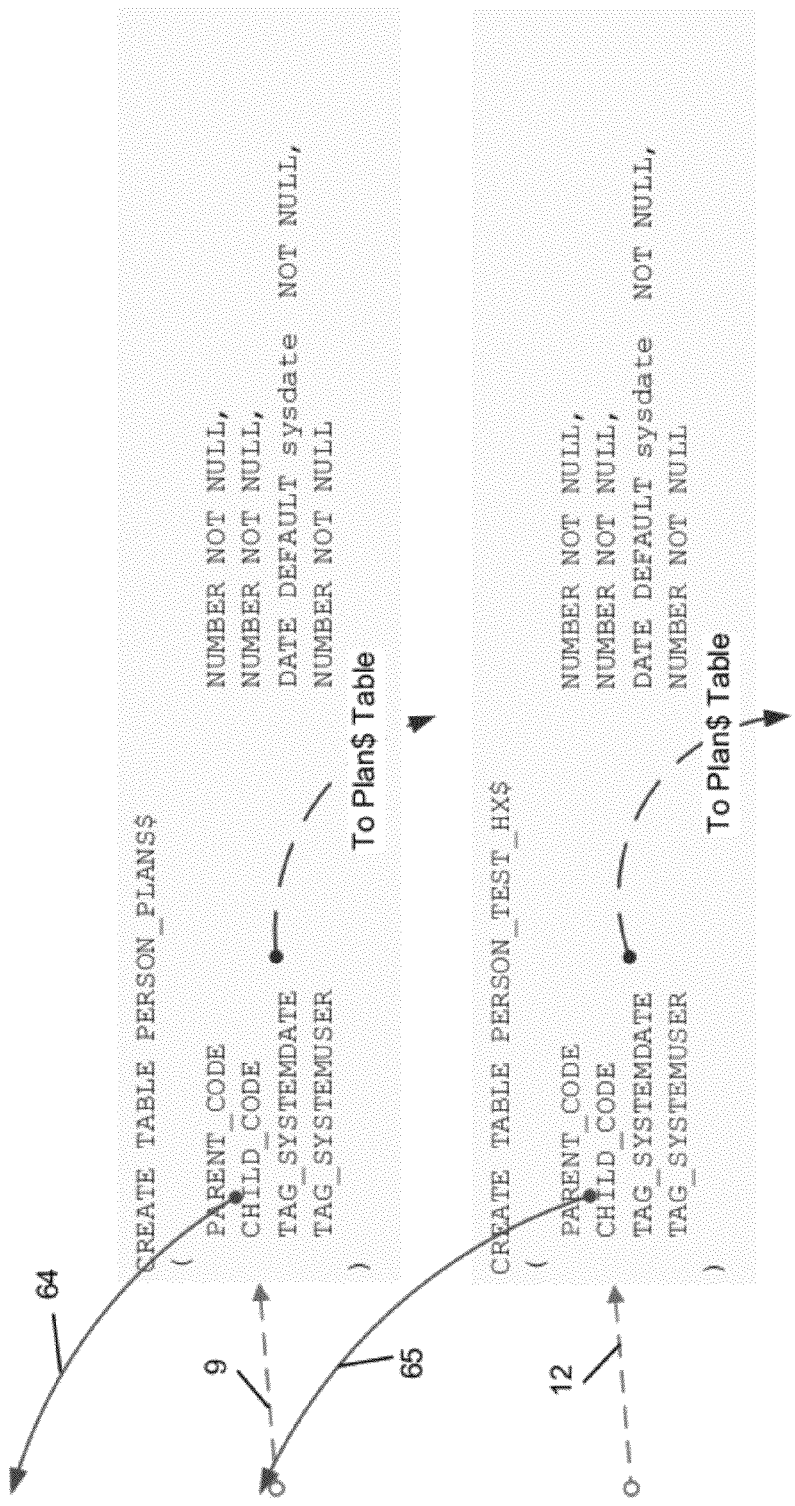
Figure 14N:
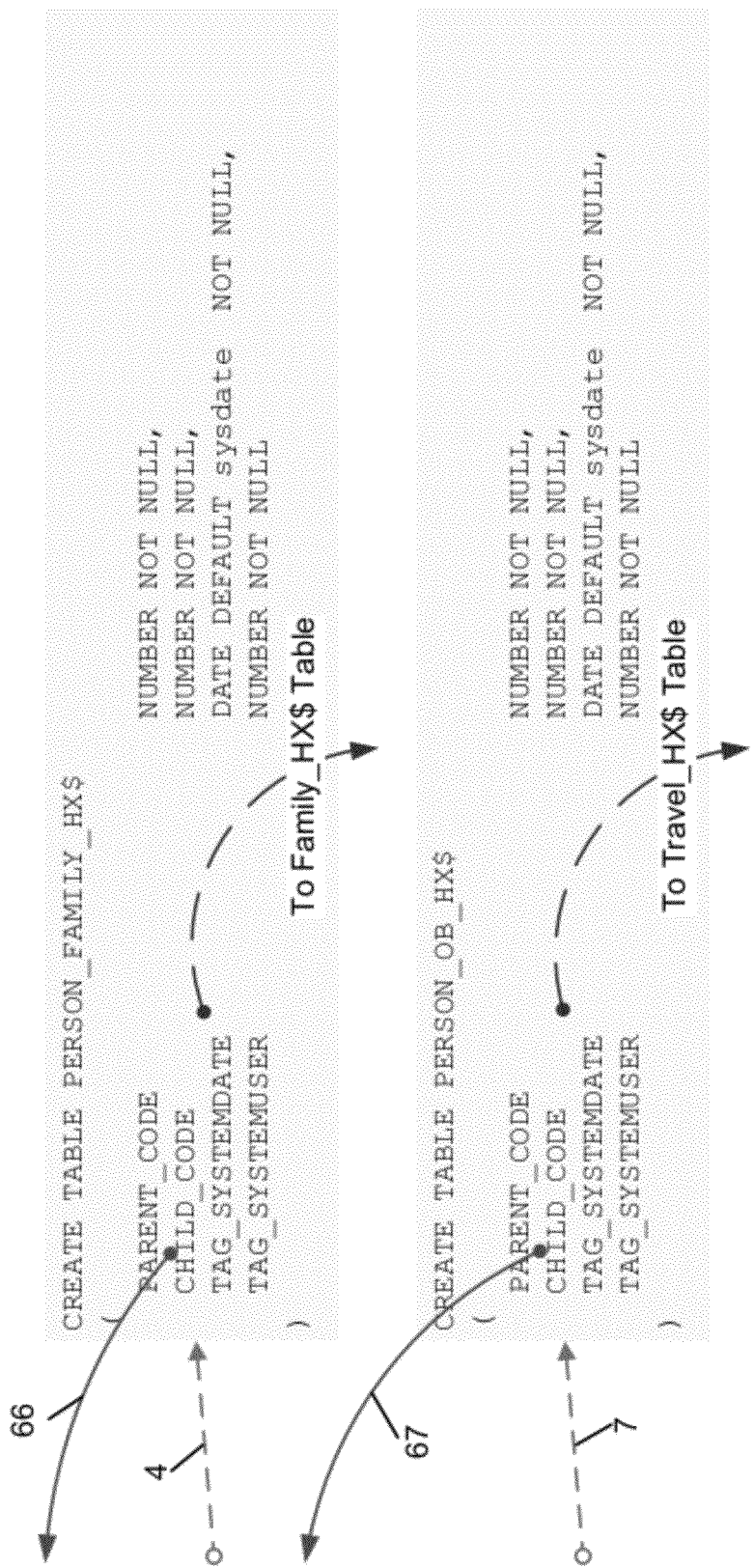
Figure 14O:
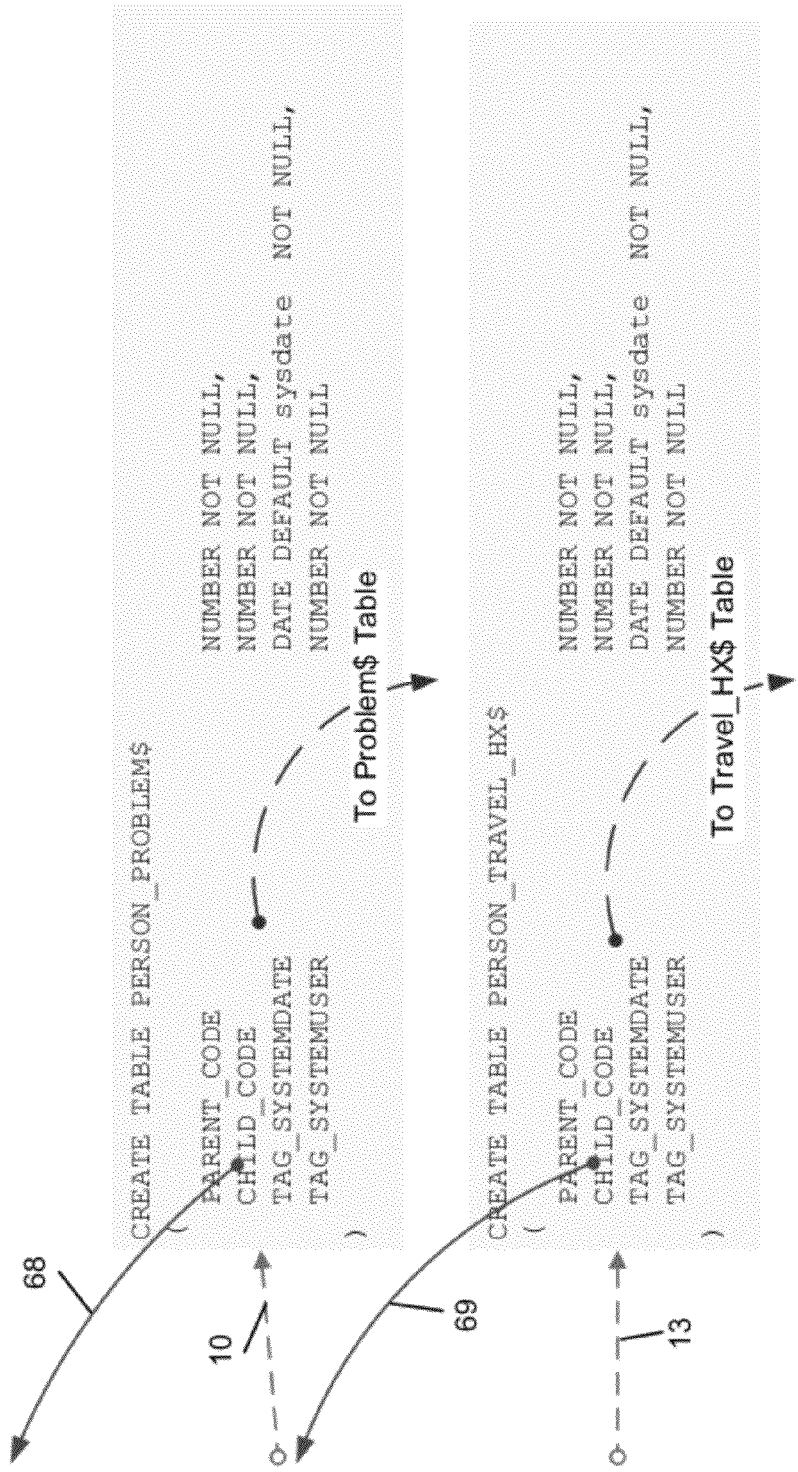
Figure 14P:
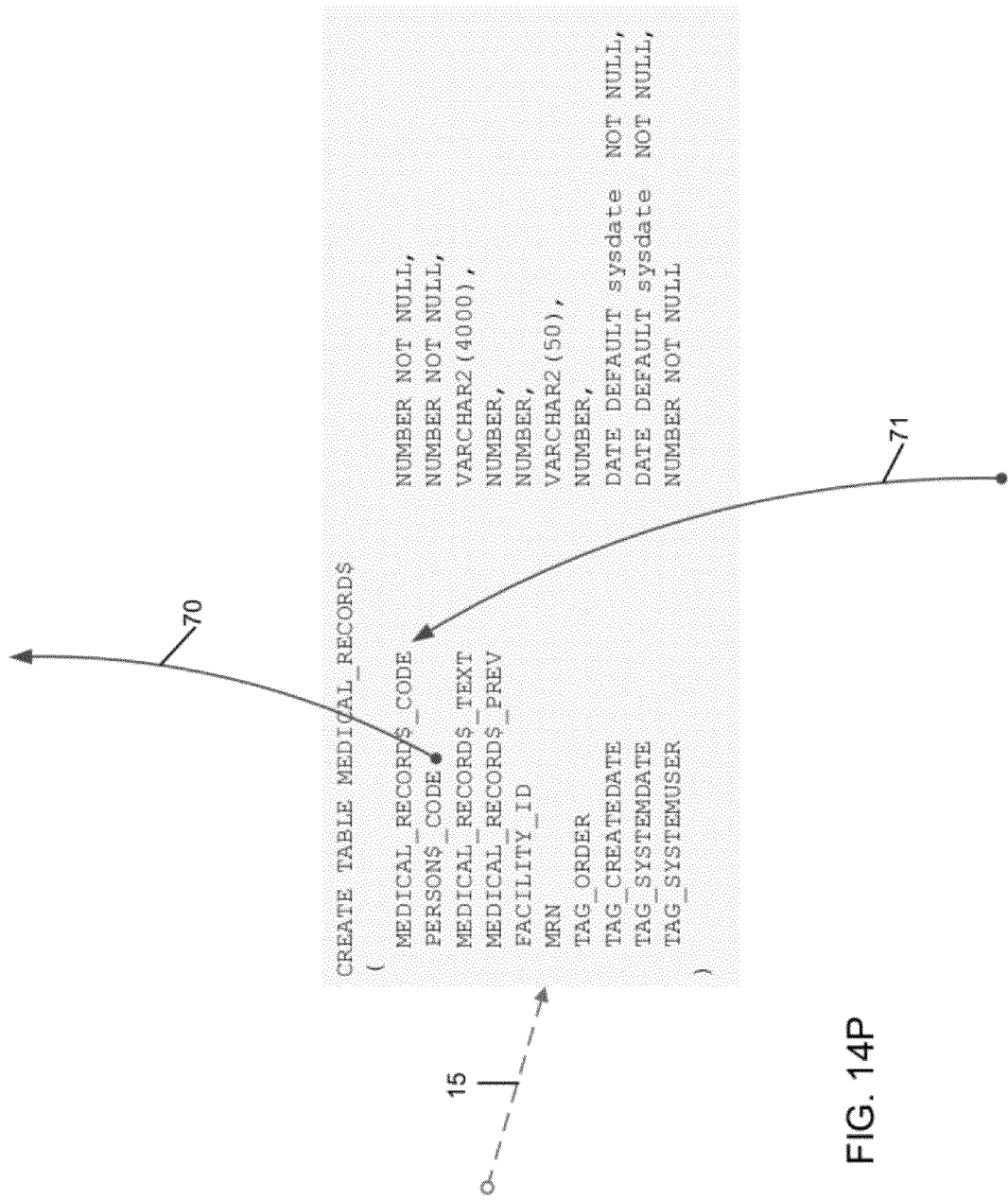
Figure 14Q:
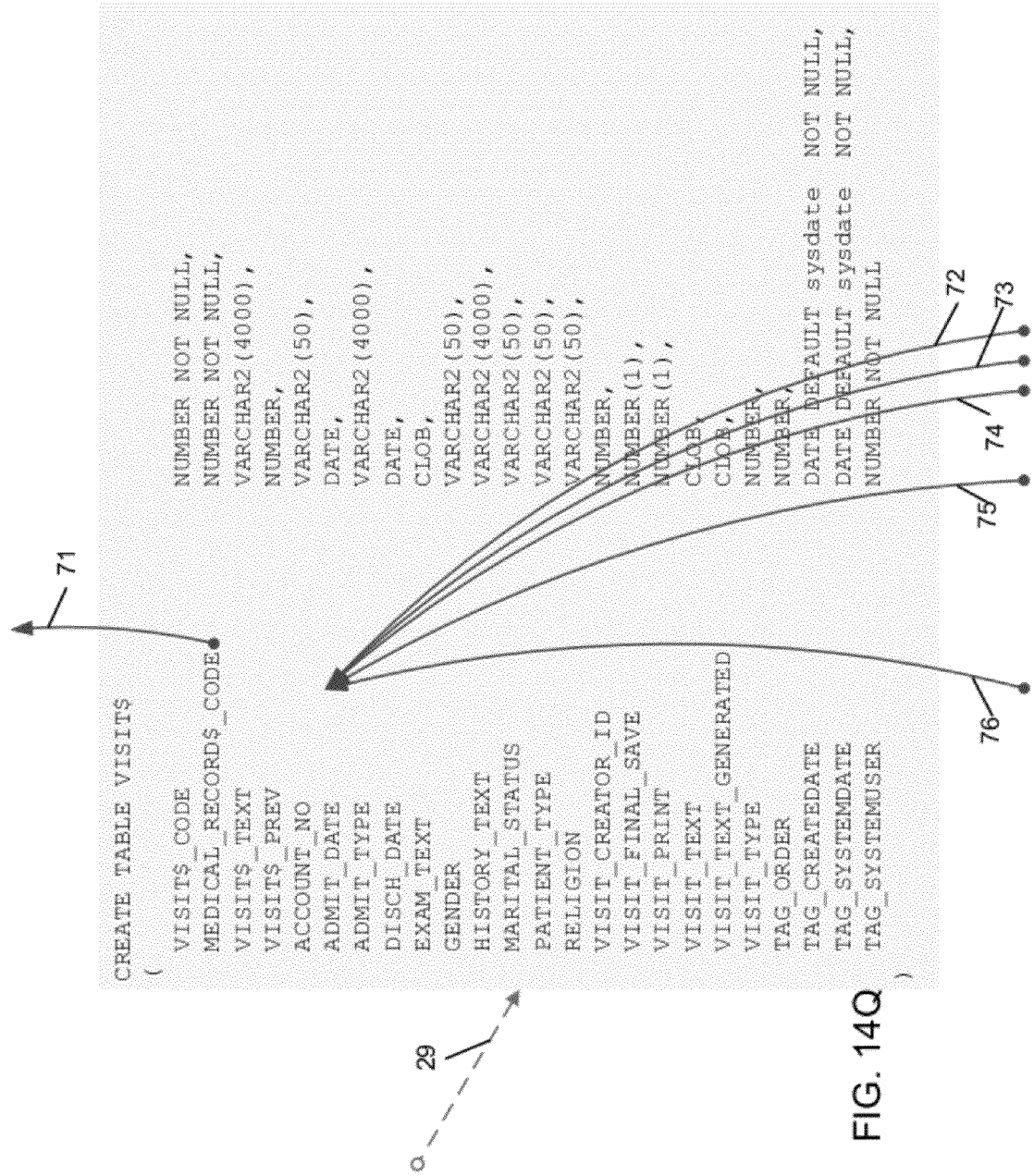
Figure 14R:
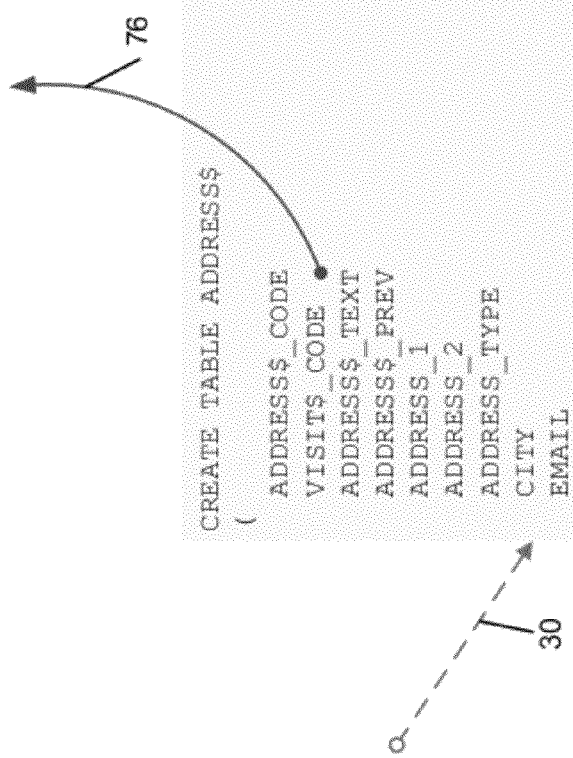
Figure 14T:
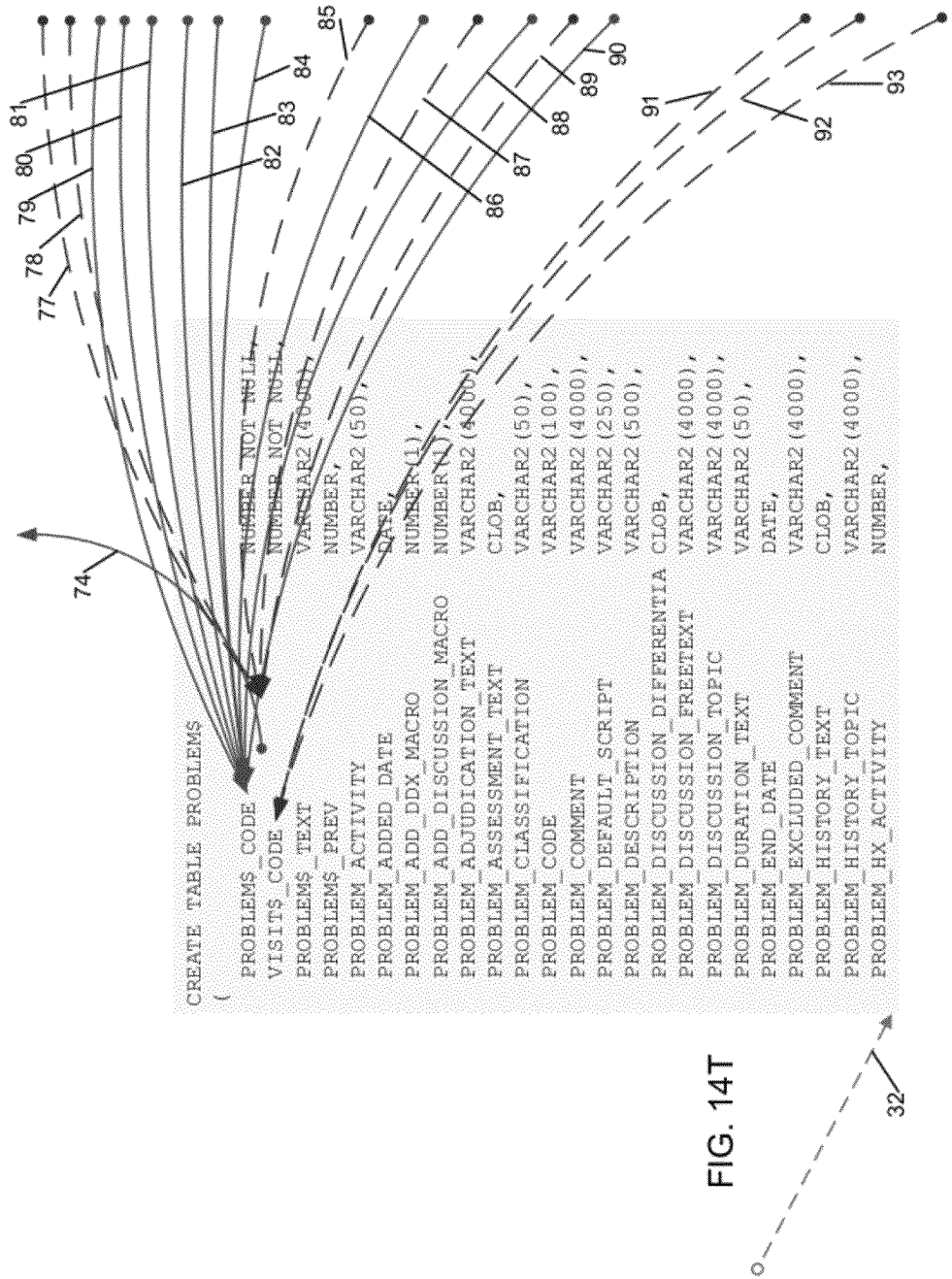
Figure 14V:
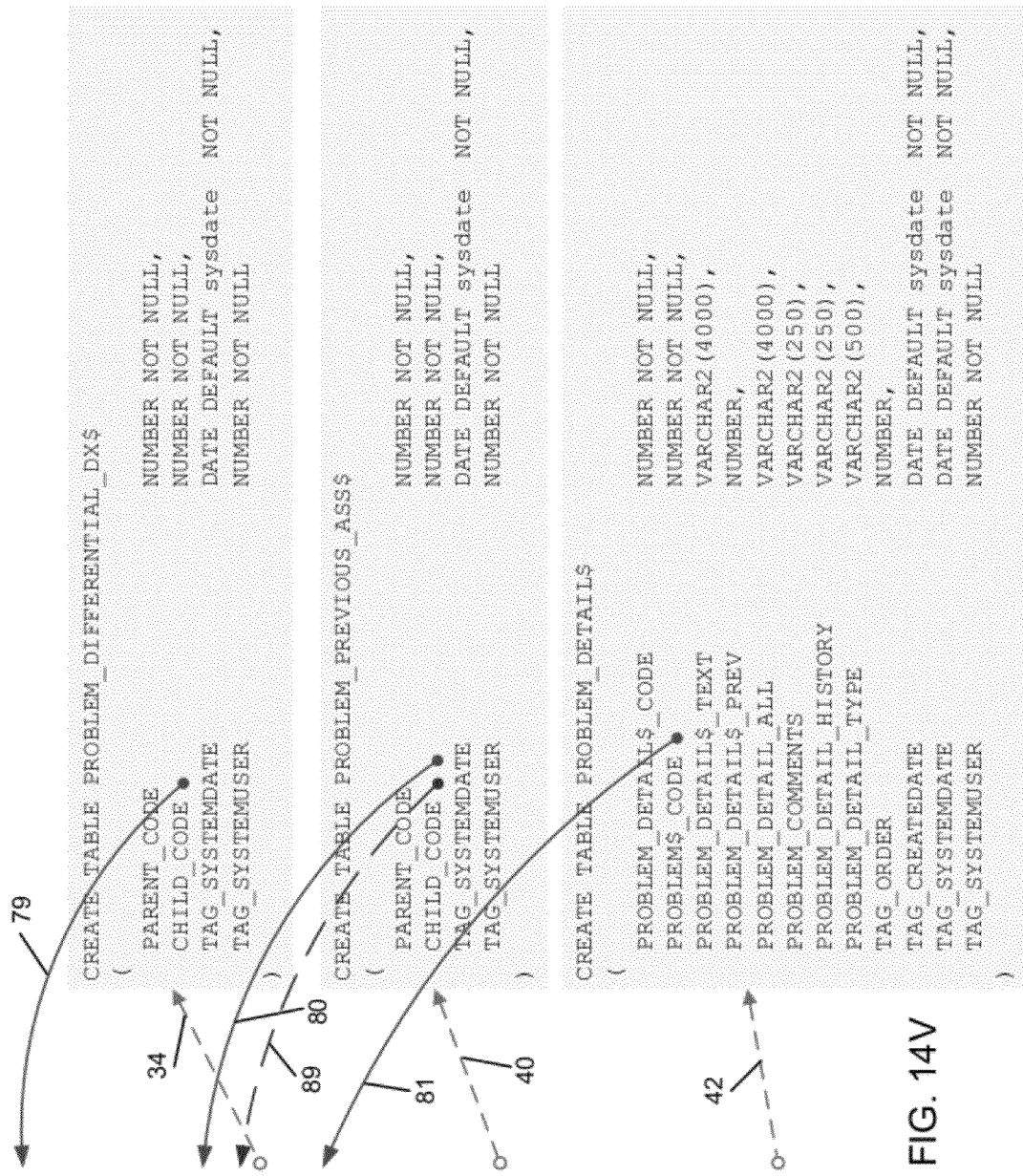
Figure 14W:
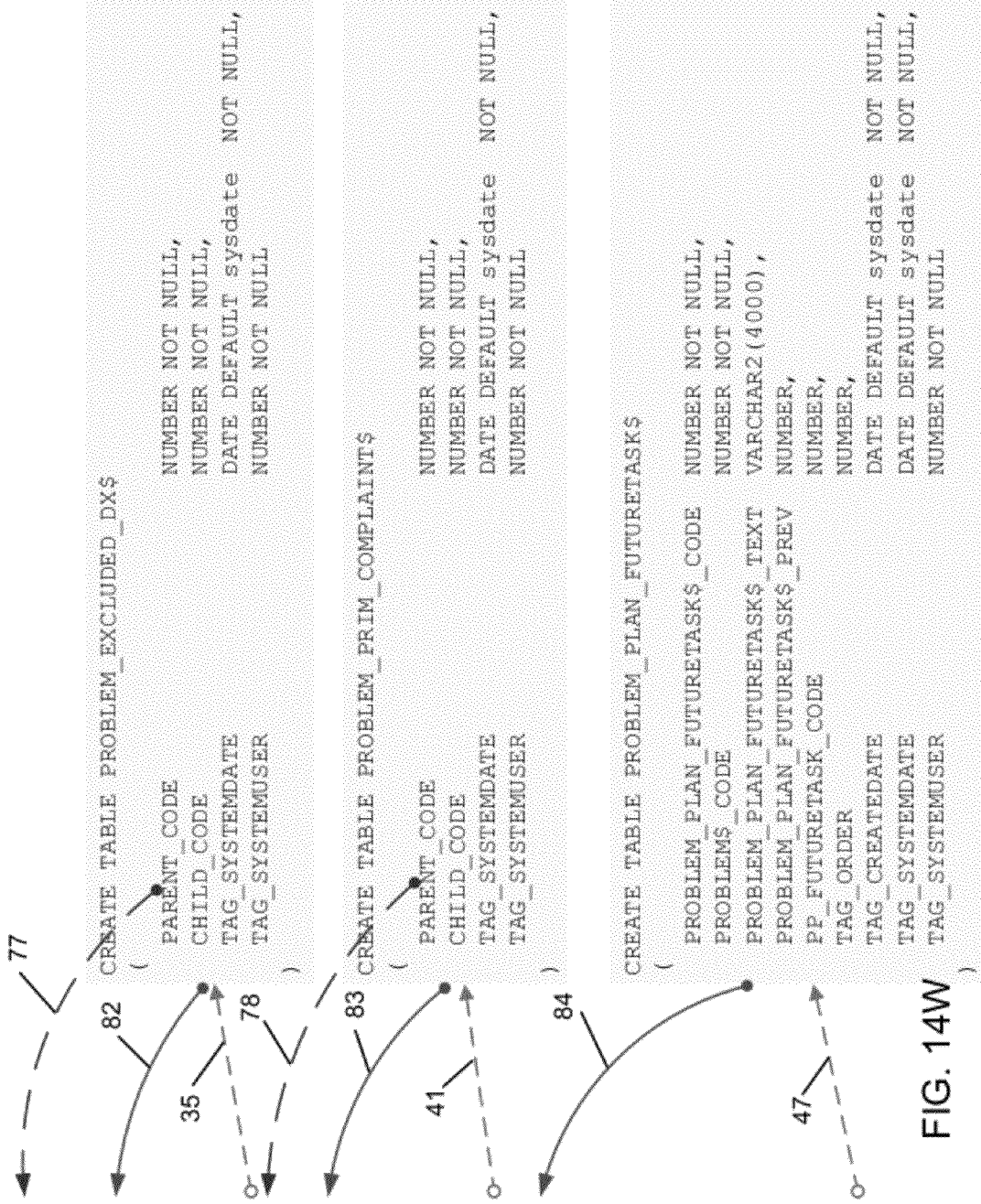
Figure 14X:
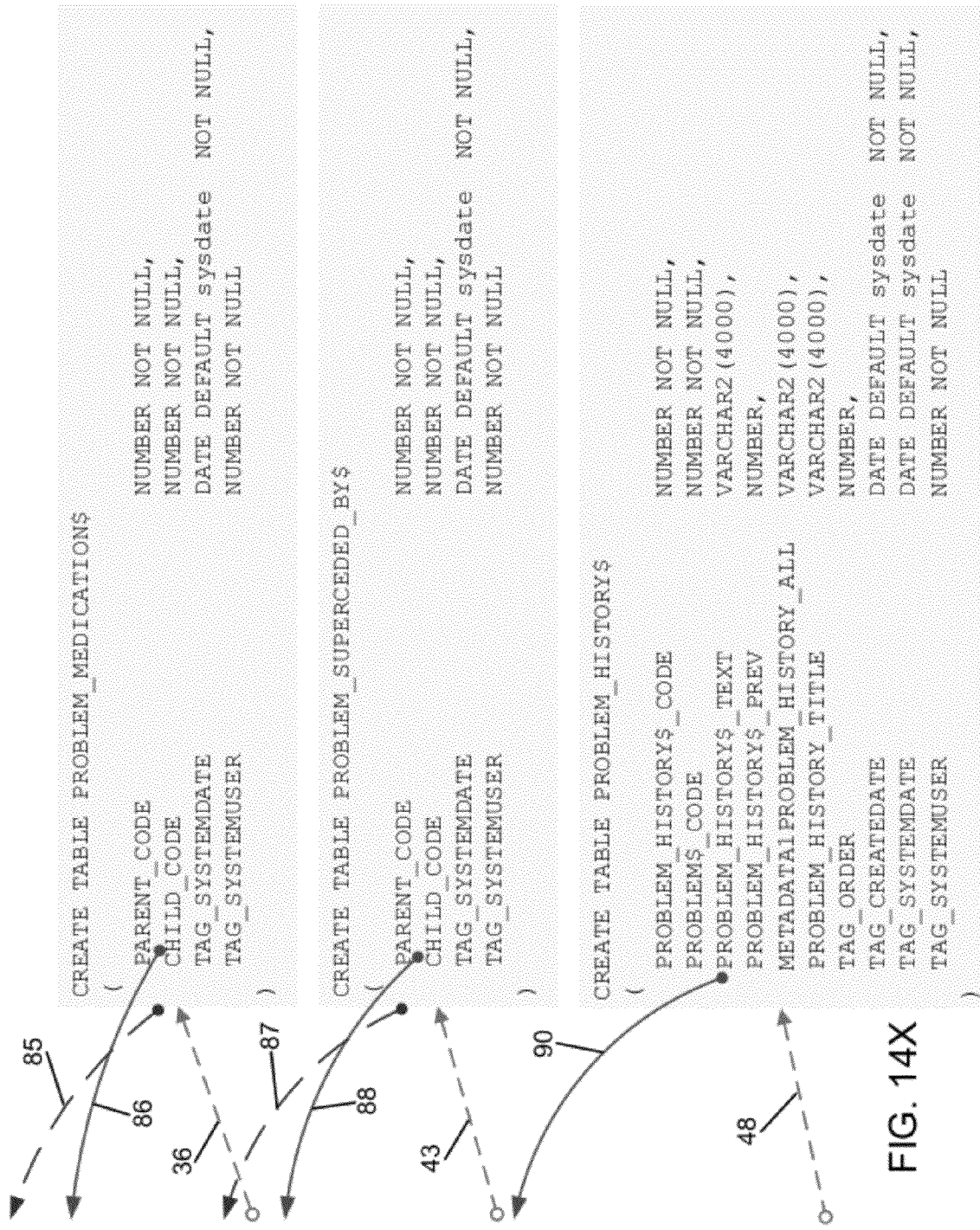
Figure 14Y:
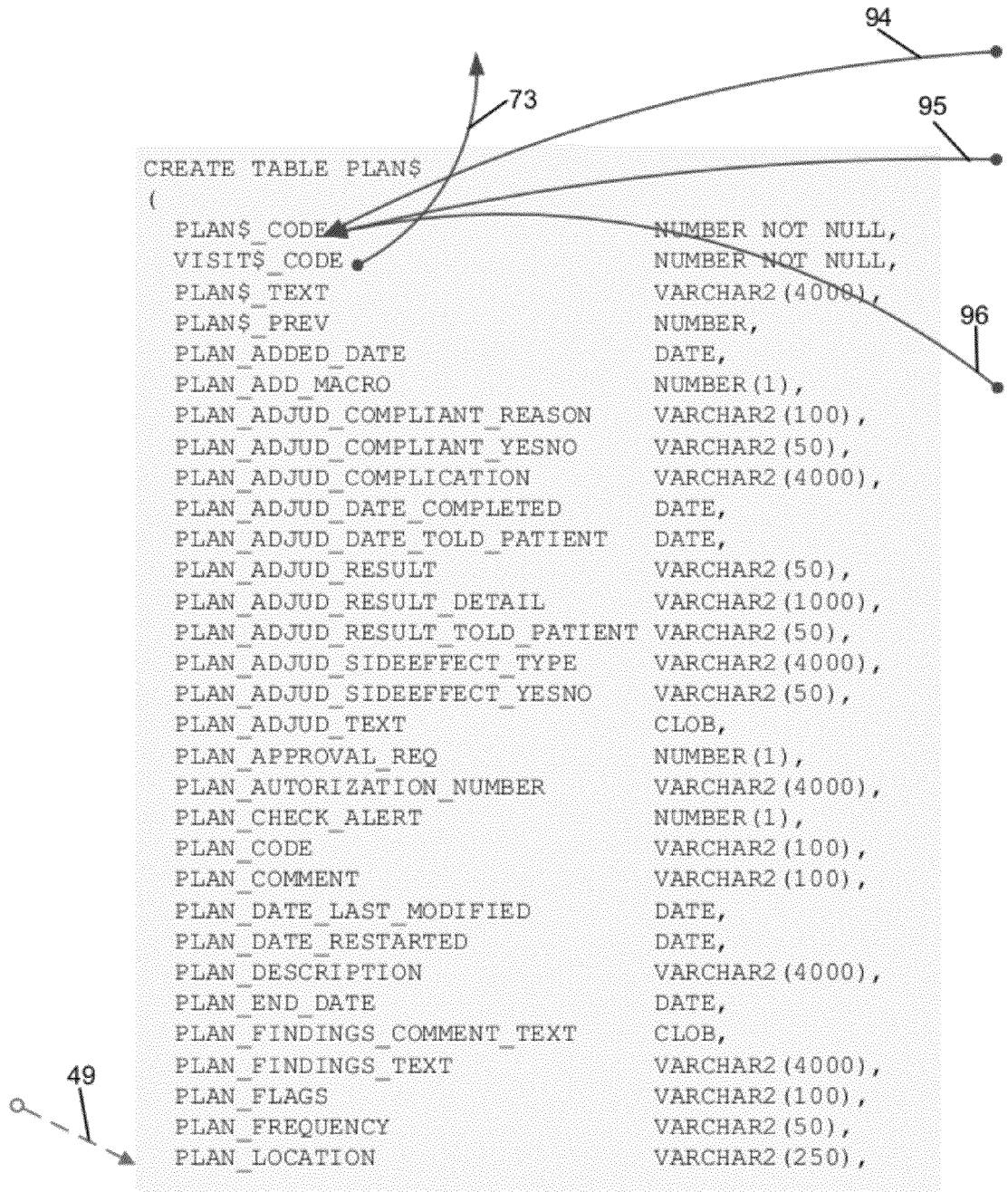
Figure 14A:
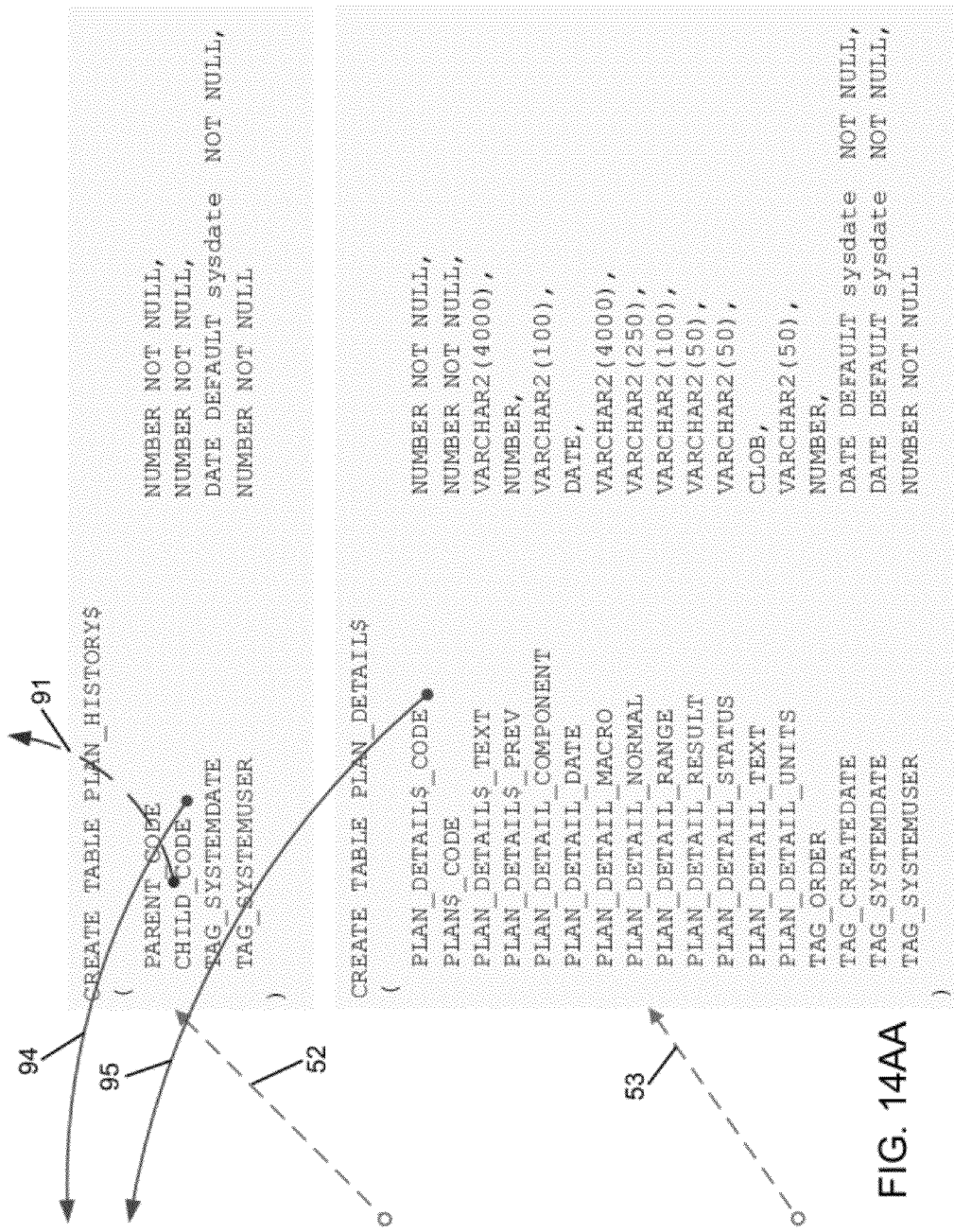
Figure 14B:
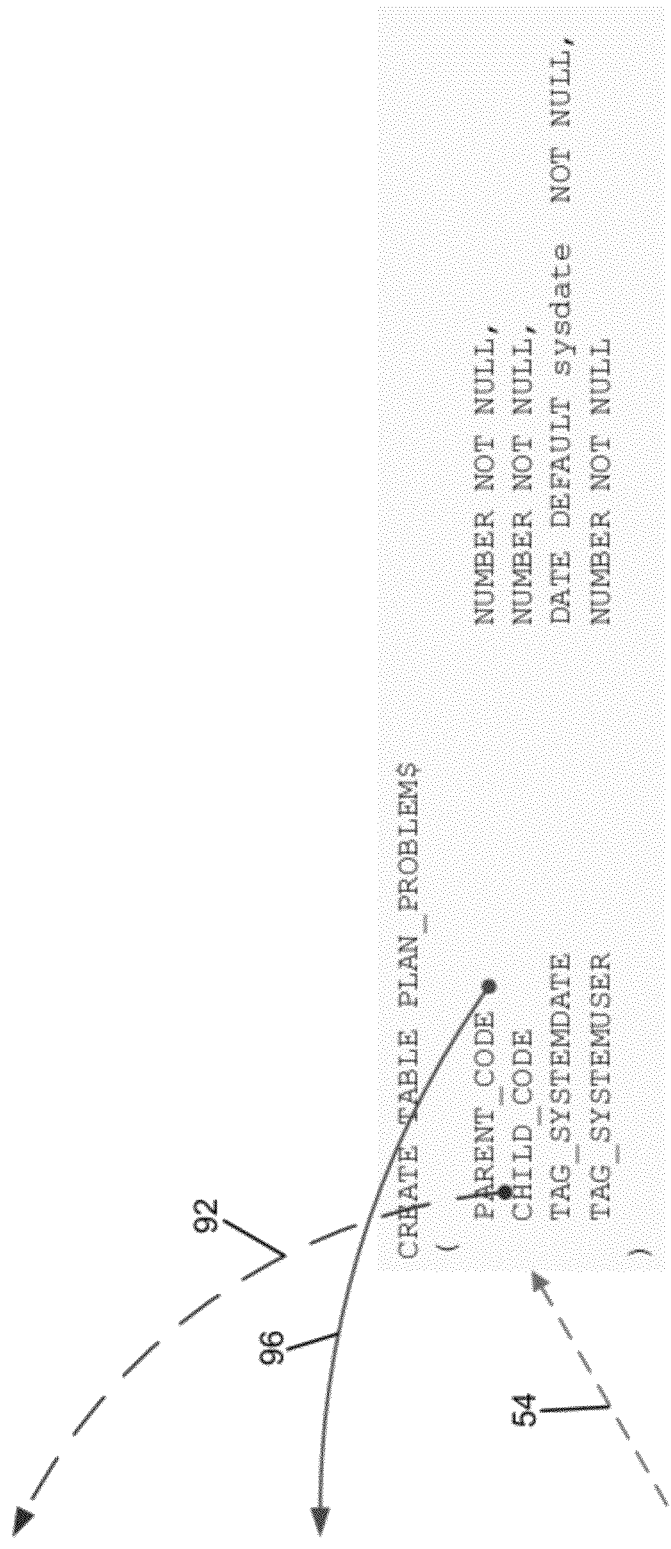
Figure 14E:
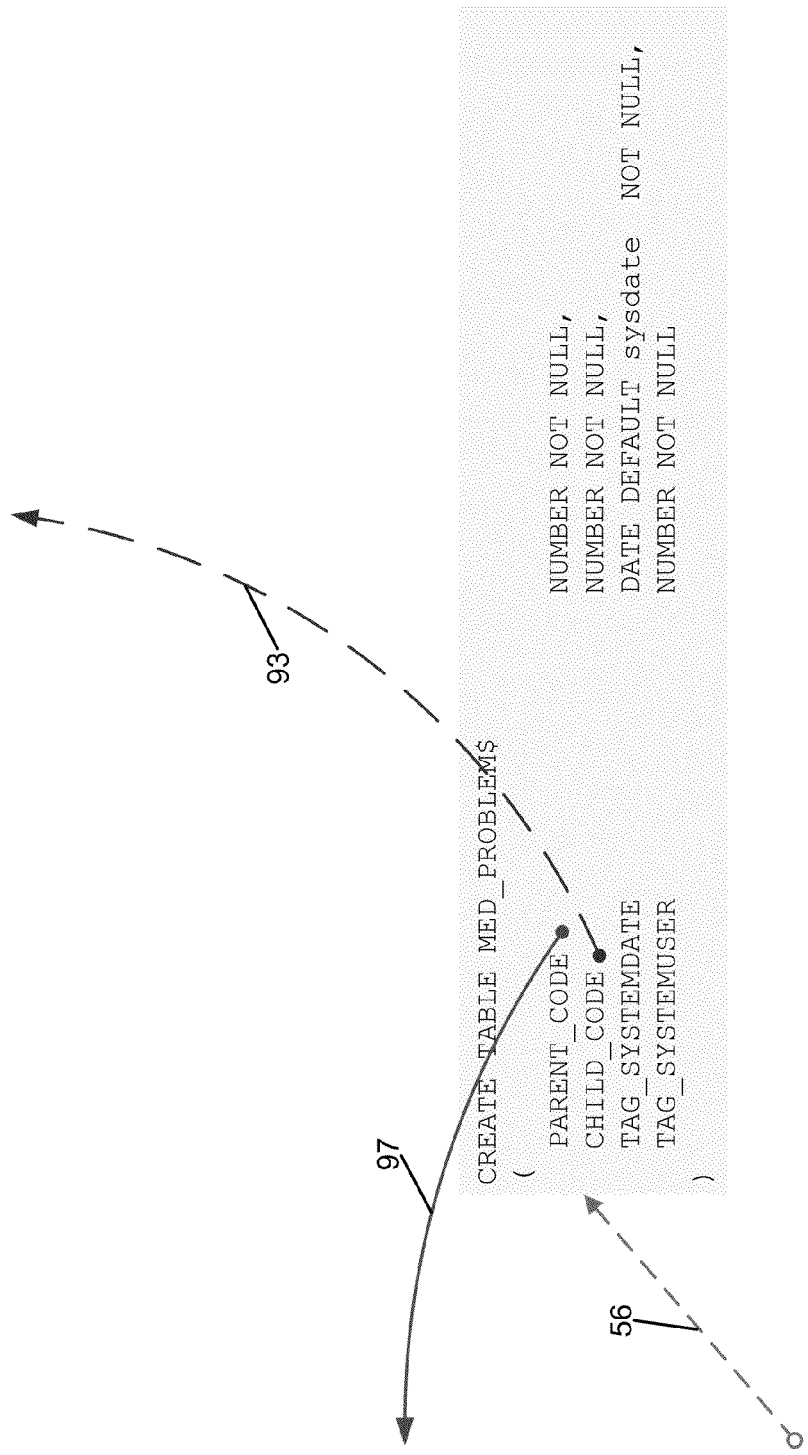

Note that FIG. 14's instance data database objects, as shown with more clarity in FIGS. 14I-14EE, do not include text for the primary key and foreign key database constraints; all instantiated elements do actually translate into primary key and foreign key constraint relationships.

Deployment similar to that of FIG. 14 deployment also includes several events that are not shown in the figure and happen concurrently with creating the main instance data objects:

Creations of the archive matching tables: all dynamically created tables may also have a matching '_arc' table, similar in structure, with the purpose to archive past column values during update and delete operations.

Creations of triggers allowing data movements from table to archive table.

Expansion of Meta data flags into particular aspects of trigger generation, notably in the case of Meta data payload indexing.

Role assignments. ADM security layer is driven by roles, and roles are automatically granted set of rights on all dynamically created objects.

As discussed above, the following code shows a portion of the example depicted in FIG. 11 as an XML document.

```
<meta name="PERSON">
<meta name="DOB" datatype="Date"/>
<meta name="ETHNICITY" datatype="String"/>
<meta name="FIRST_NAME" datatype="String"/>
<meta name="FULL_NAME" datatype="String"/>
```

```xml
<meta name="HISPANIC" datatype="Integer"/>
<meta name="IDN_EMPI_NO" datatype="String"/>
<meta name="LANGUAGE" datatype="String"/>
<meta name="LAST_NAME" datatype="String"/>
<meta name="MAIDEN_NAME" datatype="String"/>
<meta name="MIDDLE_NAME" datatype="String"/>
<meta name="MOTHERS_MAIDEN_NAME" datatype="String"/>
<meta name="PATIENT_STATUS" datatype="Integer"/>
<meta name="SSN" datatype="String"/>
<meta name="SUFFIX" datatype="String"/>
<meta name="TRAINING_PATIENT" datatype="Boolean"/>
<meta name="VIP_INDICATOR" datatype="String"/>
<meta name="PERSON_ADDRESS" link="ADDRESS[ ]"/>
<meta name="PERSON_ALLERGY" link="ALLERGY[ ]"/>
<meta name="PERSON_FAMILY_HX" link="FAMILY_HX[ ]"/>
<meta name="PERSON_IMMUNE_HX" link="IMMUNE_HX[ ]"/>
<meta name="PERSON_MEDS" link="MEDICATIONS[ ]"/>
<meta name="PERSON_OB_HX" link="OB_HX[ ]"/>
<meta name="PERSON_PASTMEDICAL_HX" link="PROBLEM[ ]"/>
<meta name="PERSON_PLANS" link="PLAN[ ]"/>
<meta name="PERSON_PROBLEM" link="PROBLEM[ ]"/>
<meta name="PERSON_SOC_HX" link="SOCIAL_HX[ ]"/>
<meta name="PERSON_TEST_HX" link="PLAN[ ]"/>
<meta name="PERSON_TRAVEL_HX" link="TRAVEL_HX[ ]"/>
<meta name="PERSON_VITALS" link="VITALS_[ ]"/>
<meta name="MED_REC_NO" datatype="Array"/>
<meta name="FACILITY_ID" datatype="Integer"/>
<meta name="MRN" datatype="String"/>
<meta name="VISIT" datatype="Array"/>
<meta name="ACCOUNT_NO" datatype="String"/>
<meta name="DISCH DATE" datatype="Date"/>
<meta name="ADMIT_DATE" datatype="Date"/>
<meta name="ADMIT_TYPE" datatype="String"/>
<meta name="GENDER" datatype="String"/>
<meta name="HISTORY_TEXT" datatype="String"/>
<meta name="MARITAL_STATUS" datatype="String"/>
<meta name="PATIENT_TYPE" datatype="String"/>
<meta name="RELIGION" datatype="String"/>
<meta name="VISIT_CREATOR_ID" datatype="Integer"/>
<meta name="VISIT_FINAL_SAVE" datatype="Boolean"/>
<meta name="VISIT_TEXT" datatype="LongString"/>
<meta name="VISIT_TYPE" datatype="Integer"/>
<meta name="ADDRESS" datatype="Array"/>
<meta name="ADDRESS_1" datatype="String"/>
<meta name="ADDRESS_2" datatype="String"/>
<meta name="ADDRESS_TYPE" datatype="String"/>
<meta name="CITY" datatype="String"/>
<meta name="EMAIL" datatype="String"/>
<meta name="STATE" datatype="String"/>
<meta name="TELEPHONE_1" datatype="String"/>
<meta name="TELEPHONE_2" datatype="String"/>
<meta name="ZIP_CODE" datatype="String"/>
</meta>
<meta name="ALLERGY" datatype="Array">
<meta name="ALLERGY_ADDED_DATE" datatype="Date"/>
<meta name="ALLERGY_CODE" datatype="String"/>
<meta name="ALLERGY_COMMENT" datatype="String"/>
<meta name="ALLERGY_DESCRIPTION" datatype="String"/>
<meta name="ALLERGY_DETAIL" datatype="Array">
<meta name="ALLERGY_DETAIL_TEXT" datatype="String"/>
<meta name="ALLERGY_REACTION" datatype="String"/>
</meta>
<meta name="ALLERGY_DONOT_RECHALLENGE" datatype="Boolean"/>
<meta name="ALLERGY_END_DATE" datatype="Date"/>
<meta name="ALLERGY_LAST_MODIFIED_DATE" datatype="Date"/>
<meta name="ALLERGY_MATNO" datatype="String"/>
<meta name="ALLERGY_ONSET_DATE" datatype="Date"/>
<meta name="ALLERGY_REPORT_SHOW" datatype="Boolean"/>
<meta name="ALLERGY_SOURCE" datatype="String"/>
<meta name="ALLERGY_STATUS" datatype="String"/>
</meta>
<meta name="EXAM" datatype="Array">
<meta name="EXAM_CODE" datatype="Rear"/>
<meta name="EXAM_COMMENT" datatype="String"/>
<meta name="EXAM_FINDINGS" datatype="String"/>
<meta name="EXAM_HIERARCHY_CODE" datatype="Rear">
<meta name="EXAM_LOCATION" datatype="String"/>
<meta name="EXAM_OVERALL" datatype="String"/>
<meta name="EXAM_SOURCE" datatype="String"/>
<meta name="EXAM_TITLE" datatype="String"/>
</meta>
<meta name="EXAM_TEXT" datatype="LongString"/>
<meta name="FAMILY_HX" datatype="Array">
<meta name="FAMILY_HX_ACTIVITY" datatype="String"/>
<meta name="FAMILY_HX_AGE" datatype="Integer"/>
<meta name="FAMILY_HX_AGE_LAST_MODIFIED_DATE" datatype="Date"/>
<meta name="FAMILY_HX_CODE" datatype="String"/>
<meta name="FAMILY_HX_COMMENT" datatype="String"/>
<meta name="FAMILY_HX_DATE" datatype="Date"/>
<meta name="FAMILY_HX_DEFAULT_SCRIPT" datatype="String"/>
<meta name="FAMILY_HX_DETAIL" datatype="Array">
<meta name="FAMILY_HX_DETAIL_ALL" datatype="String"/>
</meta>
<meta name="FAMILY_HX_DISPLAY_PLIST" datatype="Boolean"/>
```

```xml
<meta name="FAMILY_HX_NAME" datatype="String"/>
<meta name="FAMILY_HX_RELATION" datatype="String"/>
<meta name="FAMILY_HX_SOURCE" datatype="String"/>
<meta name="FAMILY_HX_STATUS" datatype="String"/>
<meta name="FAMILY_HX_TITLE" datatype="String"/>
</meta>
<meta name="IMMUNE_HX" datatype="Array">
<meta name="IMMUNE_HX_ACTIVITY" datatype="String"/>
<meta name="IMMUNE_HX_CODE" datatype="String"/>
<meta name="IMMUNE_HX_COMMENT" datatype="String"/>
<meta name="IMMUNE_HX_DATE" datatype="Date"/>
<meta name="IMMUNE_HX_DEFAULT_SCRIPT" datatype="String"/>
<meta name="IMMUNE_HX_DETAIL" datatype="Array">
<meta name="IMMUNE_HX_DETAIL_ALL" datatype="String"/>
</meta>
<meta name="IMMUNE_HX_DISPLAY_PLIST" datatype="Boolean"/>
<meta name="IMMUNE_HX_DUE" datatype="Date"/>
<meta name="IMMUNE_HX_SOURCE" datatype="String"/>
<meta name="IMMUNE_HX_TITLE" datatype="String"/>
</meta>
<meta name="INSURANCE" datatype="Array">
<meta name="EMPLOYER_NAME" datatype="String"/>
<meta name="ENROLLMENT_DATE" datatype="Date"/>
<meta name="GROUP_NUMBER" datatype="String"/>
<meta name="INSURANCE_ADDRESS_1" datatype="String"/>
<meta name="INSURANCE_ADDRESS_2" datatype="String"/>
<meta name="INSURANCE_CARRIER" datatype="String"/>
<meta name="INSURANCE_CITY" datatype="String"/>
<meta name="INSURANCE_ID" datatype="String"/>
<meta name="INSURANCE_PHONE" datatype="String"/>
<meta name="INSURANCE_STATE" datatype="String"/>
<meta name="INSURANCE_ZIP_CODE" datatype="String"/>
<meta name="INSURED_ADDRESS_1" datatype="String"/>
<meta name="INSURED_ADDRESS_2" datatype="String"/>
<meta name="INSURED_CITY" datatype="String"/>
<meta name="INSURED_DOB" datatype="Date"/>
<meta name="INSURED_FIRST_NAME" datatype="String"/>
<meta name="INSURED_LAST_NAME" datatype="String"/>
<meta name="INSURED_NAME" datatype="String"/>
<meta name="INSURED_REL_TO_PATIENT" datatype="Integer"/>
<meta name="INSURED_SSN" datatype="String"/>
<meta name="INSURED_STATE" datatype="String"/>
<meta name="INSURED_TELEPHONE" datatype="String"/>
<meta name="INSURED_ZIP_CODE" datatype="String"/>
<meta name="PLAN_NUMBER" datatype="String"/>
<meta name="POLICY_NUMBER" datatype="String"/>
<meta name="TERMINATION_DATE" datatype="Date"/>
</meta>
<meta name="INSURANCE_CAREGIVERS">
<meta name="INSURANCE_PRIMARY_CAREGIVER" datatype="String"/>
<meta name="INSURANCE_SECONDARY_CAREGIVER" datatype="String"/>
</meta>
<meta name="INSURANCE_MEDICAID">
<meta name="MEDICAID_ID" datatype="String"/>
<meta name="MEDICAID_PHYSICIANPROVIDERID" datatype="String"/>
<meta name="MEDICAID_STATE" datatype="String"/>
</meta>
<meta name="INSURANCE_MEDICARE">
<meta name="MEDICARE_ID" datatype="String"/>
<meta name="MEDICARE_SECONDARY_INSURANCE" datatype="Boolean"/>
</meta>
<meta name="MEDICATIONS" datatype="Array">
</meta>
<meta name="OB_HX" datatype="Array">
<meta name="OB_HX_CODE" datatype="String"/>
<meta name="OB_HX_COMMENT" datatype="String"/>
<meta name="OB_HX_DATE" datatype="Date"/>
<meta name="OB_HX_DETAIL" datatype="Array">
<meta name="OB_HX_DETAIL_ALL" datatype="String"/>
<meta name="OB_HX_DETAIL_GRAVITY" datatype="Integer"/>
<meta name="OB_HX_DETAIL_PARITY" datatype="Integer"/>
<meta name="OB_HX_DETAIL_TERM" datatype="Integer"/>
<meta name="OB_HX_DETAIL_TYPE" datatype="String">
</meta>
</meta>
<meta name="OB_HX_DISPLAY_PLIST" datatype="Boolean"/>
<meta name="OB_HX_END_DATE" datatype="Date"/>
<meta name="OB_HX_SOURCE" datatype="String"/>
<meta name="OB_HX_STATUS" datatype="String"/>
<meta name="OB_HX_TITLE" datatype="String"/>
</meta>
<meta name="PLAN" datatype="Array">
<meta name="PLAN_ADDED_DATE" datatype="Date"/>
<meta name="PLAN_DETAIL" datatype="Array">
<meta name="PLAN_DETAIL_DATE" datatype="Date"/>
```

```xml
<meta name="PLAN_DETAIL_NORMAL" datatype="String"/>
    <meta name="PLAN_DETAIL_RANGE" datatype="String"/>
    <meta name="PLAN_DETAIL_RESULT" datatype="String"/>
    <meta name="PLAN_DETAIL_STATUS" datatype="String"/>
    <meta name="PLAN_DETAIL_TEXT" datatype="LongString"/>
    <meta name="PLAN_DETAIL_UNITS" datatype="String"/>
  </meta>
</meta>
<meta name="PROBLEM" datatype="Array">
  <meta name="PROBLEM_ACTIVITY" datatype="String"/>
  <meta name="PROBLEM_ADDED_DATE" datatype="Date"/>
  <meta name="PROBLEM_ADJUDICATION_TEXT" datatype="String"/>
  <meta name="PROBLEM_ASSESSMENT_TEXT" datatype="LongString"/>
  <meta name="PROBLEM_CLASSIFICATION" datatype="String"/>
  <meta name="PROBLEM_CODE" datatype="String"/>
  <meta name="PROBLEM_COMMENT" datatype="String"/>
  <meta name="PROBLEM_DEFAULT_SCRIPT" datatype="String"/>
  <meta name="PROBLEM_DESCRIPTION" datatype="String"/>
  <meta name="PROBLEM_DETAIL" datatype="Array">
    <meta name="PROBLEM_DETAIL_ALL" datatype="String"/>
    <meta name="PROBLEM_DETAIL_COMMENT" datatype="String"/>
    <meta name="PROBLEM_DETAIL_TYPE" datatype="String"/>
  </meta>
  <meta name="PROBLEM_DIFFERENTIAL_DX" link="PROBLEM[ ]"/>
  <meta name="PROBLEM_DISCUSSION_DIFFERENTIAL_TEXT" datatype="LongString"/>
  <meta name="PROBLEM_DISCUSSION_FREETEXT" datatype="String"/>
  <meta name="PROBLEM_DISCUSSION_TOPIC" datatype="String"/>
  <meta name="PROBLEM_DURATION_TEXT" datatype="String"/>
  <meta name="PROBLEM_END_DATE" datatype="Date"/>
  <meta name="PROBLEM_EXCLUDED_COMMENT" datatype="String"/>
  <meta name="PROBLEM_EXCLUDED_DX" link="PROBLEM[ ]"/>
  <meta name="PROBLEM_HISTORY" datatype="Array">
    <meta name="PROBLEM_HISTORY_ALL" datatype="String"/>
    <meta name="PROBLEM_HISTORY_TITLE" datatype="String"/>
  </meta>
  <meta name="PROBLEM_HISTORY_TEXT" datatype="LongString"/>
  <meta name="PROBLEM_HISTORY_TOPIC" datatype="String"/>
  <meta name="PROBLEM_HX_ACTIVITY" datatype="Integer"/>
  <meta name="PROBLEM_INSERT_DURATION_TEXT" datatype="Boolean"/>
  <meta name="PROBLEM_LAST_MODIFIED_DATE" datatype="Date"/>
  <meta name="PROBLEM_MEDICATION" link="MEDICATIONS[ ]"/>
  <meta name="PROBLEM_NOTE" datatype="LongString"/>
  <meta name="PROBLEM_OLD_REVISION" datatype="Boolean"/>
  <meta name="PROBLEM_ONSET_DATE" datatype="Date"/>
  <meta name="PROBLEM_ONSET_DATE_PARTIAL" datatype="String"/>
  <meta name="PROBLEM_ORIENTATION_TEXT" datatype="LongString"/>
  <meta name="PROBLEM_PLAN" link="PLAN[ ]"/>
  <meta name="PROBLEM_PLANS_TEXT" datatype="LongString"/>
</meta>
<meta name="PROBLEM_PREVIOUS_ASSESSMENT" link="PROBLEM[ ]"/>
<meta name="PROBLEM_PRIMARY_COMPLAINT" link="PROBLEM[ ]"/>
<meta name="PROBLEM_SEVERITY_FLAG" datatype="Integer"/>
<meta name="PROBLEM_SHOW_IN_HISTORY" datatype="Boolean"/>
<meta name="PROBLEM_SHOW_IN_PROBLEMS" datatype="Boolean"/>
<meta name="PROBLEM_SOURCE" datatype="String"/>
<meta name="PROBLEM_STATUS" datatype="String"/>
<meta name="PROBLEM_STATUS_1_SUBJECTIVE" datatype="String"/>
<meta name="PROBLEM_STATUS_2" datatype="String"/>
<meta name="PROBLEM_STATUS_2_SUBJECTIVE" datatype="String"/>
<meta name="PROBLEM_SUPERCEDED_BY" link="PROBLEM[ ]"/>
</meta>
<meta name="ROS" datatype="Array">
  <meta name="ROS_COMMENT" datatype="String"/>
  <meta name="ROS_FINDINGS" datatype="String"/>
  <meta name="ROS_LOCATION" datatype="String"/>
  <meta name="ROS_OVERALL" datatype="String"/>
  <meta name="ROS_TITLE" datatype="String"/>
</meta>
<meta name="SOCIAL_HX" datatype="Array">
  <meta name="SOCIAL_HX_CODE" datatype="String"/>
  <meta name="SOCIAL_HX_COMMENT" datatype="String"/>
  <meta name="SOCIAL_HX_DESCRIPTION" datatype="String"/>
  <meta name="SOCIAL_HX_DETAIL" datatype="Array">
    <meta name="SOCIAL_HX_AMOUNT" datatype="String"/>
```

```xml
<meta name="SOCIAL_HX_AMOUNT_UNIT" datatype="String"/>
<meta name="SOCIAL_HX_DETAIL_AMOUNT" datatype="String"/>
<meta name="SOCIAL_HX_DETAIL_AMOUNT_UNIT" datatype="String"/>
<meta name="SOCIAL_HX_DETAIL_COMMENT" datatype="String"/>
<meta name="SOCIAL_HX_DETAIL_DURATION" datatype="String"/>
<meta name="SOCIAL_HX_DETAIL_DURATION_UNIT" datatype="String"/>
<meta name="SOCIAL_HX_DETAIL_HISTORY" datatype="String"/>
<meta name="SOCIAL_HX_DETAIL_TYPE" datatype="String"/>
<meta name="SOCIAL_HX_DURATION" datatype="String"/>
<meta name="SOCIAL_HX_DURATION_UNIT" datatype="String"/>
<meta name="SOCIAL_HX_HISTORY" datatype="String"/>
</meta>
<meta name="SOCIAL_HX_END_DATE" datatype="Date"/>
<meta name="SOCIAL_HX_ONSET_DATE" datatype="Date"/>
<meta name="SOCIAL_HX_SOURCE" datatype="String"/>
<meta name="SOCIAL_HX_STATUS" datatype="String"/>
<meta name="SOCIAL_HX_TYPE" datatype="String"/>
</meta>
<meta name="TRAVEL_HX" datatype="Array">
<meta name="TRAVEL_HX_CODE" datatype="String"/>
<meta name="TRAVEL_HX_COMMENT" datatype="String"/>
<meta name="TRAVEL_HX_DATE" datatype="Date"/>
<meta name="TRAVEL_HX_DETAIL" datatype="Array">
<meta name="TRAVEL_HX_DETAIL_ALL" datatype="String"/>
<meta name="TRAVEL_HX_DETAIL_COMMENTS" datatype="String"/>
<meta name="TRAVEL_HX_DETAIL_DETAILS" datatype="String"/>
</meta>
<meta name="TRAVEL_HX_END_DATE" datatype="Date"/>
<meta name="TRAVEL_HX_SOURCE" datatype="String"/>
<meta name="TRAVEL_HX_STATUS" datatype="String"/>
<meta name="TRAVEL_HX_TITLE" datatype="String"/>
</meta>
<meta name="VISIT_PROPERTY" datatype="Array">
<meta name="VISIT_PROPERTY_NAME" datatype="String"/>
<meta name="VISIT_PROPERTY_VALUE" datatype="String"/>
</meta>
<meta name="VITALS" datatype="Array">
</meta>
</meta>
</meta>
</meta>
```

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method for longitudinal electronic record-keeping, comprising:
    storing discrete data elements for an individual in a directed graph data structure;
    creating a new record for a visit, wherein said new record is a wrapper for said discrete data elements captured during said visit;
    collecting a group of records for said individual, said group of records comprising additional discrete data elements and at least one identifier reference;
    determining a problem based on said additional discrete data elements in said group of records and said visit;
    ordering a plan motivated by said problem;
    repeating said creating, determining and ordering steps for a subsequent visit to document additional problems and plans;
    following up on said problems and plans during said subsequent visit;
    generating historical linkages within the directed graph data structure of said problems and said plans; and
    maintaining a current list of said problems and said plans that are relevant to said individual;
    wherein the step of generating historical linkages includes linking at least one problem to a problem summarization reference and at least one plan to a plan summarization reference, wherein each summarization reference is a collection of pointers to data elements.

2. A method according to claim 1, further comprising the steps of:
    closing each record of said group of records at the end of each visit;
    preventing entry of further discrete data elements to each record after said closing.

3. A method according to claim 1, further comprising the step of:
    creating a task at the completion of said visit.

4. A method according to claim 1, wherein said method is based on a task-driven workflow.

5. A method according to claim 4, wherein said task-driven workflow comprises producing a task calendar of events, functional data review and task production.

6. A method according to claim 5, further comprising the step of:
    using a new or existing task list to trigger a task or reminder.

7. A method according to claim 1, wherein said method allows for transporting said data elements from one system to another generally without incurring data loss.

8. A method according to claim 1, wherein said discrete data elements captured during a visit may be elevated to a problem or plan following said subsequent visit.

9. A method for longitudinal electronic record-keeping, comprising:

storing discrete data elements for an individual in a directed graph data structure, said storing step comprising;
- creating a new record for a visit, said new record comprising additional discrete data elements and at least one identifier reference;
- coding at least one of said additional discrete data elements in an array to reflect a problem;
- coding at least another of said additional discrete data elements in an array to reflect a plan motivated by said problem;
- repeating said creating and said coding steps for a subsequent visit to update said problem and said plan or to document additional problems and plans;

generating historical linkages within the directed graph data structure of said problems and said plans; and maintaining a current list of said problems and said plans that are relevant to said individual, said maintaining step comprising back-linking a pointer from a data object reflecting said update to said problem or at least one of said additional problems to point to said at least one of said additional discrete data elements.

10. A method according to claim 9, further comprising:
linking at least one problem to a problem summarization reference and at least one plan to a plan summarization reference, wherein each summarization reference is a collection of pointers to data elements in at least one of said arrays.

11. A method according to claim 9, further comprising:
linking at least one data element reflecting a problem to at least one data element reflecting a plan.

12. A method according to claim 9, wherein at least one data element is linked to a problem summarization reference at a first time and re-linked to a plan summarization reference at a second, later time.

13. A method according to claim 9, wherein at least one data element is polymorphic.

14. A method according to claim 9, wherein a data element reflecting a problem is linked to a plurality of data elements reflecting multiple plans.

15. A method according to claim 9, wherein a data element reflecting a plan is linked to a plurality of data elements reflecting multiple problems.

16. A method according to claim 9, wherein said plan reflected in said at least another of said additional discrete data elements is one of an order, a referral, a medication, or a discharge instruction.

17. A method according to claim 9, said generating step comprising:
- repointing a pointer from a problem summarization reference and said at least one of said additional discrete data elements to point to a data object reflecting said update to said problem or at least one of said additional problems; and
- repointing a pointer from a plan summarization reference and said at least another of said additional discrete data elements to point to a data object reflecting said update to said plan or at least one of said additional plans.

18. A method according to claim 9, further comprising:
importing data elements reflecting a current status of at least one problem and at least one plan into a face sheet; and displaying said face sheet.

19. A method for longitudinal electronic record-keeping, comprising:
storing discrete data elements for an individual in a directed graph data structure, said storing step comprising;
- creating a new record for a visit, said new record comprising additional discrete data elements and at least one identifier reference;
- coding at least one of said additional discrete data elements in an array to reflect a problem;
- coding at least another of said additional discrete data elements in an array to reflect a plan motivated by said problem;
- repeating said creating and said coding steps for a subsequent visit to update said problem and said plan or to document additional problems and plans;
- generating historical linkages within the directed graph data structure of said problems and said plans;

linking at least one problem to a problem summarization reference and at least one plan to a plan summarization reference, wherein each summarization reference is a collection of pointers to data elements in at least one of said arrays; and maintaining a current list of said problems and said plans that are relevant to said individual.

* * * * *